(12) United States Patent
Thompson et al.

(10) Patent No.: US 8,163,750 B2
(45) Date of Patent: Apr. 24, 2012

(54) FLUORENE DERIVATIVES, COMPOSITIONS CONTAINING THE SAME AND USE THEREOF AS INHIBITORS OF THE PROTEIN CHAPERONE HSP 90

(75) Inventors: Fabienne Thompson, Paris (FR); Patrick Mailliet, Paris (FR); Jean-Marie Ruxer, Paris (FR); Helene Goulaouic, Paris (FR); Francois Vallee, Paris (FR); Herve Minoux, Paris (FR); Fabienne Pilorge, Paris (FR); Luc Bertin, Paris (FR); Stephane Hourcade, Paris (FR); Maria Mendez-Perez, Frankfurt am Main (DE); Peter Hamley, Frankfurt am Main (DE)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/625,005

(22) Filed: Nov. 24, 2009

(65) Prior Publication Data

US 2010/0130503 A1   May 27, 2010

Related U.S. Application Data

(63) Continuation of application No. 12/424,777, filed on Apr. 16, 2009, now abandoned, which is a continuation of application No. PCT/FR2007/001703, filed on Oct. 17, 2007.

(30) Foreign Application Priority Data

Oct. 24, 2006  (FR) ...................................... 06 09331

(51) Int. Cl.
*C07D 471/04* (2006.01)
*A61K 31/437* (2006.01)

(52) U.S. Cl. ...... 514/249; 514/300; 514/311; 514/265.1; 514/352; 546/113; 544/295; 544/310; 544/333; 544/362

(58) Field of Classification Search .................. 514/249, 514/300, 311, 265.1, 303, 352; 546/113; 544/310, 362, 333, 295
See application file for complete search history.

(56) References Cited

U.S. PATENT DOCUMENTS

| | | | |
|---|---|---|---|
| 6,855,705 B1 | 2/2005 | Tian et al. | |
| 7,674,795 B2 * | 3/2010 | Mailliet et al. | 514/252.04 |
| 2005/0026894 A1 | 2/2005 | Tian et al. | |
| 2006/0019941 A1 | 1/2006 | Adams et al. | |
| 2006/0089495 A1 | 4/2006 | Blagg et al. | |
| 2006/0205705 A1 | 9/2006 | Ross et al. | |
| 2008/0070960 A1 | 3/2008 | Bertin et al. | |
| 2008/0108612 A1 | 5/2008 | Carrez et al. | |
| 2009/0054452 A1 | 2/2009 | Eggenweiler et al. | |

FOREIGN PATENT DOCUMENTS

| | | |
|---|---|---|
| JP | 2005/225787 | 8/2005 |
| WO | WO 02/36075 | 5/2002 |
| WO | WO 03/041643 | 5/2003 |
| WO | WO 2004/007051 | 1/2004 |
| WO | WO 2004/050067 | 6/2004 |
| WO | WO 2004/056782 | 7/2004 |
| WO | WO 2004/072080 | 8/2004 |
| WO | WO 2004/096212 | 11/2004 |
| WO | WO 2005/000300 | 1/2005 |
| WO | WO 2005/000778 | 1/2005 |
| WO | WO 2005/006322 | 1/2005 |
| WO | WO 2005/021552 | 3/2005 |
| WO | WO 2005/028434 | 3/2005 |
| WO | WO 2005/034950 | 4/2005 |
| WO | WO 2005/051808 | 6/2005 |
| WO | WO 2005/063714 | 7/2005 |
| WO | WO 2005/072766 | 8/2005 |
| WO | WO 2006/008503 | 1/2006 |
| WO | WO 2006/010594 | 2/2006 |
| WO | WO 2006/010595 | 2/2006 |
| WO | WO 2006/014744 | 2/2006 |
| WO | WO 2006/016773 | 2/2006 |
| WO | WO 2006/018082 | 2/2006 |
| WO | WO 2006/050477 | 5/2006 |
| WO | WO 2006/050501 | 5/2006 |
| WO | WO 2006/055760 | 5/2006 |
| WO | WO 2006/079789 | 8/2006 |
| WO | WO 2006/084030 | 8/2006 |
| WO | WO 2006/087077 | 8/2006 |
| WO | WO 2006/090094 | 8/2006 |
| WO | WO 2006/091963 | 8/2006 |
| WO | WO 2006/095783 | 9/2006 |
| WO | WO 2006/101052 | 9/2006 |
| WO | WO 2006/105372 | 10/2006 |
| WO | WO 2006/123061 | 11/2006 |

OTHER PUBLICATIONS

Ali, A., et. al., Hsp90 Interacts With and Regulates the Activity of Heat Shock Factor 1 in Xenopus Occytes, Molecular and Cellular Biology, (1998), pp. 4949-4960, vol. 18, No. 9.

(Continued)

*Primary Examiner* — Kahsay T Habte
(74) *Attorney, Agent, or Firm* — Scully, Scott, Murphy & Presser PC

(57) ABSTRACT

The present invention relates to compounds of formula (I):

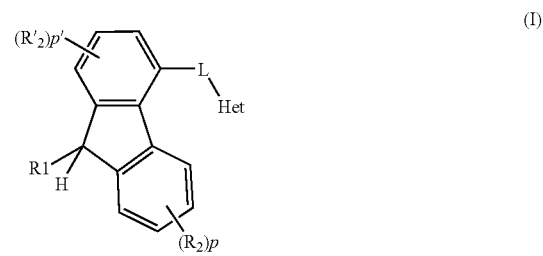

wherein R1, $R_2$, $R_2'$, L, Het, p and p' are as defined herein, compositions containing them, and their use as medicinal products.

12 Claims, No Drawings

OTHER PUBLICATIONS

Banumathyl, G., et. al., Heat Shock Protein 90 Function is Essential for Plasmodium Faiciparum Growth in Human Erythrocytes, The Journal of Biological Chemistry, vol. 278, No. 20, (2003), pp. 18336-18345.

Bharadwaj, S., et al., Multiple Components of the Hsp90 Chaperone Complex Function in Regulation of Heat Shock Factor 1 in Vivo, Molecular and Cellular Biology, (1999), pp. 8033-8041, vol. 19, No. 12.

Chiosis, G., et. al., A Small Molecule Designed to Bind to the Adenine Nucleotide Pocket of Hsp90 Causes Her2 Degradation and the Growth Arrest and Differentiation of Breast Cancer Cells, Chemistry & Biology, vol. 8, (2001), pp. 289-299.

Chiosis, G., et. al., Development of Purine-Scaffold Small Molecule Inhibitors of Hsp90, Current Cancer Drug Targets, (2003), vol. 3, pp. 371-376.

Chiosis, G., et al., HSP90: The Vulnerable Chaperone, DDT, vol. 9, No. 20, (2004) pp. 881-888.

Cowen, L. E., et al., Hsp90 Potentiates the Rapid Evolution of New Traits: Drug Resistance in Diverse Fungi, Science, vol. 309, pp. 2185-2189, (2005).

Devaney, E., et al., Hsp90 is Essential in the Filarial Nematode Brugla Pahangi, International Journal for Parasitology, vol. 35, (2005), pp. 627-636.

Echeverria, P. C., et al., Toxoplasma Gondii Hsp90 is a Potential Drug Target Whose Expression and Subcellular Localization are Developmentally Regulated, J. Mol. biol. (2005), vol. 350, pp. 723-734.

Eustace, B. K., et al., Functional Proteomic Screens Reveal an Essential Extracellular Role for HSP90a in Cancer Cell Invasiveness, Nature Cell Biology, vol. 6, pp. 507-514, (2004).

Fujiwara, H., et al., IC101 Induces Apoptosis by Akt Dephosphorylation Via An Inhibition of Heat Shock Protein 90-ATP Binding Activity Accompanied by Preventing the Interaction with Akt in L1210 Cells, J. Pharmacol. Exp. Ther., (2004), vol. 310, pp. 1288-1295.

Hanahan, D., et al., The Hallmarks of Cancer, Cell, vol. 100, pp. 57-70, (2000).

Hu, J., et. al., Hsp90 is Required for the Activity of a Hepatitis B Virus Reverse Transcriptase, Proc. Natl. Acad. Sci. USA, vol. 93, pp. 1060-1064, (1996).

Itoh, H., et. al., A Novel Chaperone-Activity-Reducing Mechanism of the 90-kDa Molecular Chaperone Hsp90, Biochem. J., (1999), vol. 343, pp. 697-703.

Janin, Y.L., et al., Heat Shock Protein 90 Inhibitors. A Text Book Example of Medicinal Chemistry?, J. Med. Chem. (2005) 48(24) 7503-7512.

Jolly, C., et. al., Role of the Heat Shock Response and Molecular Chaperones in Oncogenesis and Cell Death, Journal of the National Cancer Instituted, vol. 92, No. 19, (2000), pp. 1564-1572.

Kieran, D., et al., Treatment with Arimoclomol, A Coinducer of Heat Shock Proteins, Delays Disease Progression in ALS Mice, Nature Medicine, vol. 10, pp. 402-405, (2004).

Kloet, E. R. D., et al., Stress and The Brain: From Adaptation to Disease, Nature Reviews Neuroscience, vol. 6, (2005), pp. 463-475.

Kumar, R, et al., The Heat Shock Protein 90 of Plasmodium Falciparum and Antimalarial Activity of its Inhibitor, Geldanamycin, Malaria Journal, vol. 2, pp. 30-41, (2003).

Li, Y-H., et. al., Geldanamycin, a Ligand of Heat Shock Protein 90, inhibits the Replication of Herpes Simplex Virus Type 1 In Vitro, Antimocrobial Agents and Chemotherapy, (2004), pp. 867-872, vol. 48, No. 3.

Maloney, A., et. al., HSP90 as a New Therapeutic Target for Cancer Thereapy: The Story Unfolds, Expert Opinion Biol. Ther., (2002), vol. 2, No. 1, pp. 3-24.

Matthews, R. C, et. al., Human Recombinant Antibody to HSP90: A Natural Partner in Combination Therapy, Current Molecular Medicine, (2005), vol. 5, pp. 403-411.

Murphy, P., et. al., Suppresive Effects of Ansamycins or inducible Nitric Oxide Synthase Expression and the Development of Experimental Autoimmune Encephalomyelitis, Journal of Neuroscience Research, vol. 67, pp. 461-470, (2002).

Neckers, L., et. al., Development of Small Molecule Hsp90 Inhibitors: Utilizing Both Forward and Reverse Chemical Genomics for Drug Identification, Current Medicinal Chemistry, (2003), vol. 10, pp. 733-739.

Neckers, L., et. al., Heat-Shock Protein 90 Inhibitors as Novel Cancer Chemotherapeutic Agents, Expert Opin. Emerging Drugs, (2002), vol. 7, pp. 277-288.

Pavithra, S. R., et. al., Recurrent Fever Promotes Plasmodium Faiciparum Development in Human Erythrocytes, The Journal of Biological Chemistry, vol. 279, No. 45, (2004), pp. 46692-46699.

Piper, P. W., et. al., The Hsp90 Chaperone as a Promising Drug Target, Current Opin. Invest. New Drugs. (2001), vol. 2, pp. 1606-1610.

Prodromou, C., et. al., Identification and Structural Characterization of the ATP/ADP-Binding Site in the Hsp90 Molecular Chaperone, Cell, vol. 90, pp. 65-75, (1997).

Roe, S. M., et. al., Structural Basis for Inhibition of the Hsp90 Molecular Chaperone by the Antitumor Antibiotics Radicicol and Geldanamycin, J. Med. Chem., (1999), vol. 42, pp. 260-266.

Sittler, A., et. al., Geldanamycin Activates a Heat Shock Response and Inhibits Huntingtin Aggregation in a Cell Culture Model of Huntington's Disease, Human Molecular Genetics. (2001), vol. 10, No. 12, pp. 1307-1315.

Smith, D. F., et. al., Chaperones in Signal Transduction, Molecular Chaperones in the Cell, pp. 165-178, Oxford University Press (2001).

Smith, D. F., et al., Molecular Chaperones: Biology and Prospects for Pharmacological Intervention, Pharmacological Reviews, vol. 50, No. 4, pp. 493-513 (1998).

Soga, S., et. al., Kf25706, A Novel Oxime Derivative of Redicicol, Exhibits in Vivo Antitumor Activity Via Selective Depletion of Hsp90 Binding Signaling Molecules, Cancer Research, vol. 59, pp. 2931-2938, (1999).

Tytell, M., et. al., Heat Shook Proteins: New Keys to the Development of Cytoprotective Therapies, Emerging Ther. Targets, (2001), vol. 5, pp. 267-287.

Valle, J. R-D., et. al., Heat Shock Protein 90 and Heat Shock Protein 70 Are Components of Dengue Virus Receptor Complex in Human Cells, Journal of Virology, (2005), pp. 4557-4567, vol. 79, No. 8.

Waxman, L., et. al., Host Cell Factor Requirement for Hepatitis C Virus Enzyme Maturation, Proc. Natl. Acad. Sci. USA, vol. 98, pp. 13931-13935, (2001).

Waza, M., et. al., 17-AAG, an Hsp90 Inhibitor, Ameliorates Polyglutamine-Mediated Motor Neuron Degeneration, Nature Medicine, vol. 11, No. 10, (2005), pp. 1088-1095.

Yu, X. M., et. al., Hsp90 Inhibitors Identified From a Library of Novobiocin Analogues, J. Amer. Chem. Soc., (2005), vol. 127, No. 37, pp. 12778-12779.

* cited by examiner

FLUORENE DERIVATIVES, COMPOSITIONS CONTAINING THE SAME AND USE THEREOF AS INHIBITORS OF THE PROTEIN CHAPERONE HSP 90

This application is a Continuation of application Ser. No. 12/424,777, filed Apr. 16, 2009, now abandoned which is a Continuation of International Application No. PCT/FR2007/001703, filed Oct. 17, 2007, which is incorporated herein by reference in its entirety.

FIELD OF THE INVENTION

The present invention relates to novel chemical compounds, tricyclic derivatives and more particularly to novel heterocyclic derivatives of carbazole, of azacarbazole, of phenanthridine, of phenothiazine, of phenoxazine and of dibenzazepine, compositions containing them, and their use as medicinal products.

More particularly, the invention relates, according to a first aspect, to novel heterocyclic derivatives of carbazole, of phenanthridine, of phenothazine, of phenoxazine and of dibenzazepine displaying anticancer activity, and in particular inhibitory activity against the Hsp90 chaperone protein, and more particularly via inhibition of the ATPase-type catalytic activity of the Hsp90 chaperone protein.

BACKGROUND OF THE INVENTION

Chaperone Proteins

The molecular chaperones of the Heat Shock Proteins class (HSPs), which are classified according to their molecular weight (Hsp27, Hsp70, Hsp90 etc.), are key elements in the balance between the synthesis and degradation of cellular proteins that are responsible for correct protein folding. They play a vital role in the response to cellular stress. The HSPs, and in particular Hsp90, are also involved in the regulation of various important cellular functions, via their association with various client proteins involved in cellular proliferation or in apoptosis (Jolly C. and Morimoto R. I., J. N. Cancer Inst., (2000), 92, 1564-72; Smith D. F. et al., Pharmacological Rev. (1998), 50, 493-513; Smith D. F., Molecular Chaperones in the Cell, 165-178, Oxford University Press 2001).

Hsp90 Chaperone and Hsp90 Inhibitors in the Treatment of Cancers:

The Hsp90 chaperone, which represents 1 to 2% of the protein content of the cell, has recently been shown to be a particularly promising target in anticancer therapy (cf. for a review: Moloney A. and Workman P., Expert Opin. Biol. Ther. (2002), 2(1), 3-24; Chiosis et al., Drug Discovery Today (2004), 9, 881-888). There is interest in particular in the cytoplasmic interactions of Hsp90 with the main client proteins of Hsp90—proteins which are involved in the six mechanisms of tumour progression, as defined by Hanahan D. and Weinberg R. A. (Cell (2002), 100, 57-70), namely:
  ability to proliferate in the absence of growth factors: EGFR-R/HER2, Src, Akt, Raf, MEK, Bcr-Abl, Flt-3 etc.
  ability to evade apoptosis: mutated form of p53, Akt, surviving etc.
  insensitivity to proliferation stop signals: Cdk4, Plk, Wee1 etc.
  ability to activate angiogenesis: VEGF-R, FAK, HIF-1, Akt etc.
  ability to proliferate without replicative limit: hTert etc.
  ability to invade new tissues and to metastasize: c-Met Among the other client proteins of Hsp90, steroid hormone receptors, such as the oestrogen receptor or the androgen receptor, are also of considerable interest in connection with anticancer therapies.

It was shown recently that the alpha form of Hsp90 also has an extracellular role via its interaction with the metalloprotease MMP-2, which is itself implicated in tumoral invasion (Eustace B. K. et al., Nature Cell Biology (2004), 6, 507-514).

Hsp90 is composed of two N- and C-terminal domains separated by a highly charged region. Dynamic interaction between these two domains, coordinated by the fixation of nucleotides and of co-chaperones, determines the conformation of the chaperone and its state of activation. Association of the client proteins depends mainly on the nature of the co-chaperones Hsp70/Hsp40, Hop60 etc., and on the nature of the ADP or ATP nucleotide joined to the N-terminal domain of Hsp90. Thus, hydrolysis of ATP to ADP and the ADP/ATP exchange factor control all of the chaperone "machinery", and it has been shown that it is sufficient to prevent the hydrolysis of ATP to ADP—ATPase activity of Hsp90—in order to release client proteins in the cytoplasm, which will then be degraded to the proteasome (Neckers L and Neckers K, Expert Opin. Emerging Drugs (2002), 7, 277-288; Neckers L, Current Medicinal Chemistry, (2003), 10, 733-739; Piper P. W., Current Opin. Invest. New Drugs (2001), 2, 1606-1610).

Role of Hsp90 and its Inhibitors in Pathologies Other than Cancer:

Various human pathologies are the consequence of incorrect folding of key proteins, notably leading to neurodegenerative diseases following aggregation of certain proteins such as in Alzheimer's disease and Huntington's disease or diseases associated with prions (Tytell M. and Hooper P. L., Emerging Ther. Targets (2001), 5, 267-287). In these pathologies, approaches aiming to inhibit Hsp90 in order to activate the stress pathways (Hsp70 for example) might be beneficial (Nature Reviews Neuroscience 6: 11, 2005). Some examples are given below:

i) Huntington's disease: This neurodegenerative disease is due to extension of CAG triplets in exon 1 of the gene encoding the protein huntingtin. It has been shown that geldanamycin inhibits the aggregation of this protein owing to overexpression of the Hsp70 and Hsp40 chaperones (Human Molecular Genetic 10: 1307, 2001).
  ii) Parkinson's disease: This disease is due to the progressive loss of dopaminergic neurons and is characterized by the aggregation of the protein alpha-synuclein. It has been shown that geldanamycin is able to protect *drosophila* against the toxicity of alpha-synuclein on the dopaminergic neurons.
  iii) Focal cerebral ischaemia: It was shown in a rat animal model that geldanamycin protects the brain against cerebral ischaemia, through the effect of stimulation of transcription of the genes encoding the "heat-shock proteins" by an Hsp90 inhibitor.
  iv) Alzheimer's disease and multiple sclerosis: These diseases are partly due to the expression of proinflammatory cytokines and of the inducible form of NOS (nitric-oxide synthase) in the brain, and this deleterious expression is suppressed by the response to stress. In particular, Hsp90 inhibitors are able to store up this response to stress, and it has been shown in vitro that geldanamycin and 17-AAG display anti-inflammatory activity in the brain's glial cells (J. Neuroscience Res. 67: 461, 2002).
  v) Amyotrophic lateral sclerosis: This neurodegenerative disease is due to the progressive loss of motor neurons.

It has been shown that arimoclomol, a heat-shock protein inducer, slows down the evolution of the disease in an animal model (Nature Medicine 10: 402, 2004). Since an Hsp90 inhibitor is also an inducer of heat-shock proteins (Mol. Cell. Biol. 19: 8033, 1999; Mol. Cell. Biol. 18: 4949, 1998), it is probable that a beneficial effect might also be obtained in this pathology for inhibitors of this type.

Moreover, an inhibitor of the Hsp90 protein might potentially be useful in various diseases, other than cancer as already mentioned, such as parasitic, viral or fungal infections, or neurodegenerative diseases—by direct action on Hsp90 and particular client proteins. Some examples are presented below:

vi) Malaria: the Hsp90 protein of *Plasmodium falciparum* displays 59% identity and 69% similarity with the Human Hsp90 protein, and it has been shown that geldanamycin inhibits the growth of the parasite in vitro (Malaria Journal 2: 30, 2003; J. Biol. Chem. 278: 18336, 2003; J. Biol. Chem. 279: 46692, 2004).

vii) Brugian and bancroftian filariodes: these filarial lymphatic parasites possess an Hsp90 protein that can potentially be inhibited by inhibitors of the human protein. In fact, it has been shown for another similar parasite, *Brugia pahangi*, that the latter is susceptible to inhibition by geldanamycin. The *B. pahangi* sequences and human sequences are 80% identical and 87% similar. (Int. J. for Parasitology 35: 627, 2005)

viii) Toxoplasmosis: *Toxoplasma gondii*, the parasite responsible for toxoplasmosis, possesses an Hsp90 chaperone protein, for which induction has been demonstrated in the course of tachyzoite-bradyzoite conversion, corresponding to transition of the chronic infection to active toxoplasmosis. Moreover, geldanamycin blocks this tachyzoite-bradyzoite conversion in vitro (J. Mol. Biol. 350: 723, 2005)

ix) Mycoses that are resistant to treatment: It is possible that the Hsp90 protein potentiates the development of drug resistance, by allowing new mutations to develop. Consequently, an Hsp90 inhibitor, alone or in combination with another antifungal treatment, might prove to be useful in the treatment of some resistant strains (Science 309: 2185, 2005). Moreover, the anti-Hsp90 antibody developed by Neu Tec Pharma displays activity against *C. albicans* which is fluconazole-sensitive and fluconazole-resistant, *C. krusei*, *C. tropicalis*, *C. glabrata*, *C. lusitaniae* and *C. parapsilosis* in vivo (Current Molecular Medicine 5: 403, 2005).

x) Hepatitis B: Hsp90 is one of the host proteins interacting with the reverse transcriptase of the hepatitis B virus during the viral replication cycle. It has been shown that geldanamycin inhibits the replication of viral DNA and the encapsulation of viral RNA (Proc. Natl. Acad. Sci. USA 93: 1060, 1996)

xi) Hepatitis C: The human Hsp90 protein takes part in the cleavage stage between the NS2 and NS3 proteins by the viral protease. Geldanamycin and radicicol are able to inhibit this NS2/3 cleavage in vitro (Proc. Natl. Acad. Sci. USA 98: 13931, 2001)

xii) Herpes virus: Geldanamycin has demonstrated activity in inhibition of replication of the HSV-1 virus in vitro, with a good therapeutic index (Antimicrobial Agents and Chemotherapy 48: 867, 2004). The authors also found geldanamycin to be active against other viruses HSV-2, VSV, Cox B3, HIV-1 and the SARS coronavirus (data not shown).

xiii) Dengue (or breakbone fever): It has been shown that the human Hsp90 protein takes part in the viral entry stage, forming a complex that also contains Hsp70 which serves as a virus receptor. An anti-Hsp90 antibody reduces the infectiousness of the virus in vitro (J. of Virology 79: 4557, 2005)

xiv) Spinal and bulbar muscular atrophy (SBMA): a hereditary neurodegenerative disease characterized by an extension of CAG triplets in the gene of the androgen receptor. It has been shown that 17-AAG, a derivative of geldanamycin, displays activity in vivo on transgenic animals serving as experimental models of this disease (Nature Medicine 11: 1088, 2005).

Hsp90 inhibitors:

The first known inhibitors of Hsp90 are compounds of the amsamycin family, in particular geldanamycin (1) and herbimycin A. X-ray studies have shown that geldanamycin binds to the ATP site of the N-terminal domain of Hsp90, where it inhibits the ATPase activity of the chaperone (Prodromou C. et al., Cell (1997), 90, 65-75).

The NIH and Kosan BioSciences are currently funding the clinical development of 17-AAG (2), an Hsp90 inhibitor derived from geldanamycin (1), which blocks the ATPase activity of Hsp90 by binding to the N-terminal ATP recognition site. Based on the results of phase I clinical trials of 17-AAG (1), phase II trials are now beginning, but research is also being directed towards derivatives that are more soluble such as analogue 3 (17-DMAG from Kosan BioSciences), which bears a dimethylamine chain instead of the methoxy residue, and towards optimized formulations of 17AAG (CNF1010 from Conforma Therapeutics):

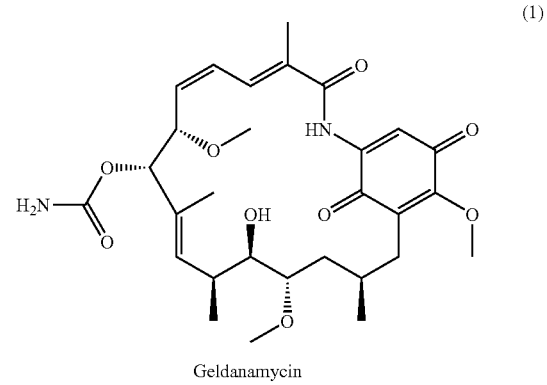

Geldanamycin (1)

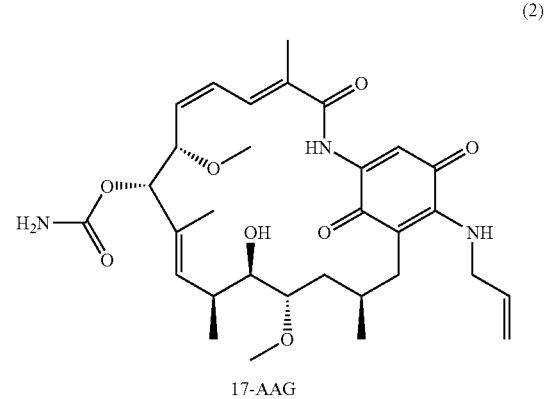

17-AAG (2)

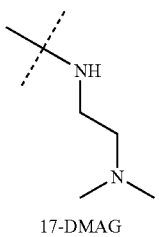

17-DMAG

The reduced analogue of 17-AAG (WO 2005063714/US 2006019941) has also recently entered phase I clinical studies by the company Infinity Pharmaceuticals. Novel derivatives of geldanamycin have been described recently (WO2006016773/U.S. Pat. No. 6,855,705/US 2005026894/WO2006/050477/US 2006205705).

Radicicol (4) is also an Hsp90 inhibitor of natural origin (Roe S. M. et al., J. Med. Chem. (1999), 42, 260-66). However, although it is by far the best inhibitor of Hsp90 in vitro, its metabolic instability with respect to sulphur-containing nucleophiles makes it difficult to use in vivo. Oxime derivatives that are much more stable such as KF 55823 (5) or KF 25706 have been developed by the company Kyowa Hakko Kogyo (Soga et al., Cancer Research (1999), 59, 2931-2938)

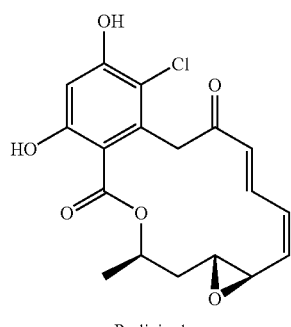

Radicicol

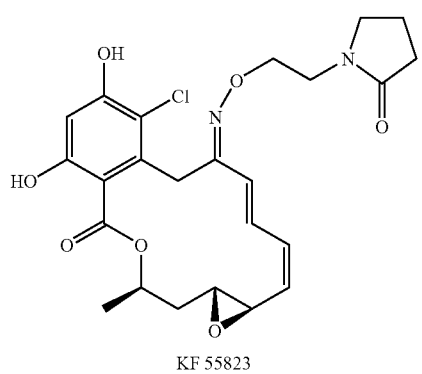

KF 55823

Structures of natural origin related to radicicol have also been described recently, such as zearalenone (6) by the company Conforma Therapeutics (WO 03041643) or compounds (7-9).

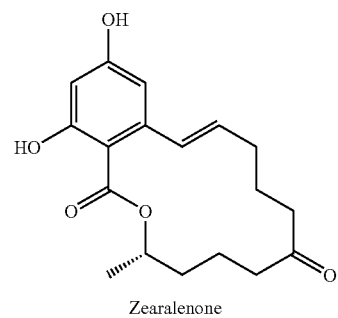

Zearalenone

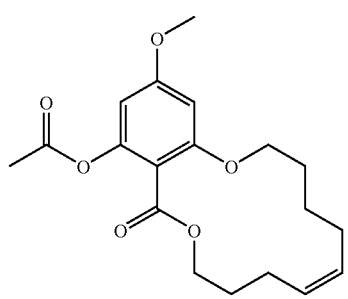

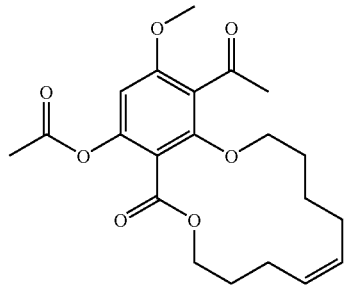

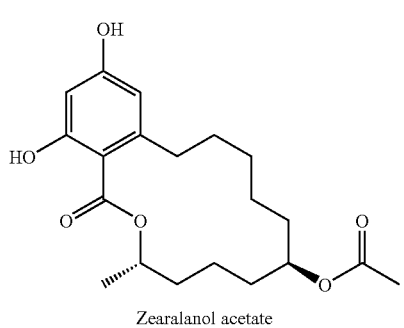

Zearalanol acetate

Patent application US2006089495 describes mixed compounds comprising a quinone nucleus, such as amsamycin derivatives, and a resorcinol nucleus such as the analogues of radicicol, as Hsp90 inhibitors.

An Hsp90 inhibitor of natural origin, novobiocin (10), binds to a different ATP site located in the C-terminal domain of the protein (Itoh H. et al., Biochem J. (1999), 343, 697-703. Recently, simplified analogues of novobiocin have been identified as more potent Hsp90 inhibitors than novobiocin itself (J. Amer. Chem. Soc. (2005), 127(37), 12778-12779).

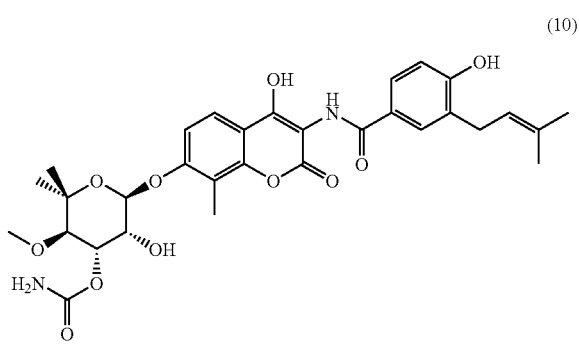

(10)

Patent application WO 2006/050501 claims analogues of novobiocin as Hsp90 inhibitors.

A depsipeptide, called Pipalamycin or ICI101 has also been described as a non-competitive inhibitor of the ATP site of Hsp90 (J. Pharmacol. Exp. Ther. (2004), 310, 1288-1295).

Sherperdine, nonapeptide KHSSGCAFL, mimics a portion of the K79-K90 sequence (KHSSGCAFLSVK) of survivin and blocks the interaction of proteins of the IAP family with Hsp90 in vitro (WO 2006014744).

Small peptides, comprising a sequence of the Otoferline type (YSLPGYMVKKLLGA), have recently been described as Hsp90 inhibitors (WO 2005072766).

Purines, such as the compounds PU3 (11) (Chiosis et al., Chem. Biol. (2001), 8, 289-299) and PU24FCI (12) (Chiosis et al., Curr. Canc. Drug

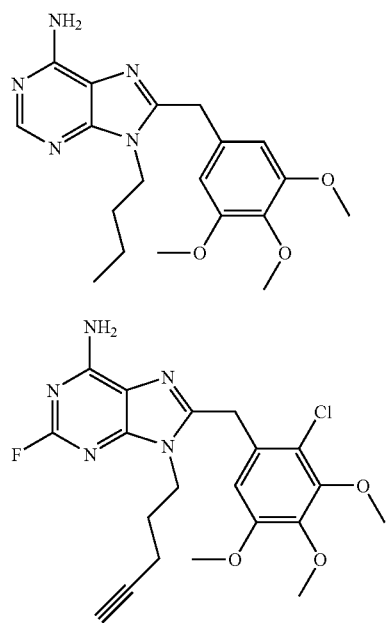

Targets (2003), 3, 371-376; WO 2002/036075) have also been described as Hsp90 inhibitors:

A purine derivative CNF2024 (13) was recently introduced into clinical practice by the company Conforma Therapeutics, in collaboration with the Sloan Kettering Memorial Institute for Cancer Research (WO 2006/084030).

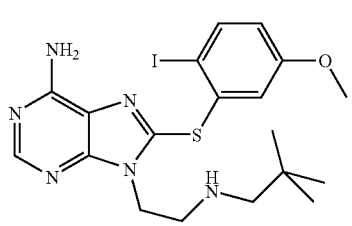

(13)

Patent application FR2880540 (Aventis) claims another family of purines as Hsp90 inhibitors.

Patent application WO2004/072080 (Cellular Genomics) claims a family of 8-heteroaryl-6-phenyl-imidazo[1,2-a]pyrazines as modulators of Hsp90 activity.

Patent application WO2005/028434 (Conforma Therapeutics) claims aminopurines, aminopyrrolopyrimidines, aminopyrazolopyrimidines and aminotriazolopyrimidines as Hsp90 inhibitors.

Patent application WO2004/050087 (Ribotarget/Vernalis) claims a family of pyrazoles that can be used for treating pathologies associated with inhibition of the heat-shock proteins such as the Hsp90 chaperone.

Patent application WO2004/056782 (Vernalis) claims a novel family of pyrazoles that can be used for treating pathologies associated with inhibition of the heat-shock proteins such as the Hsp90 chaperone.

Patent application WO2004/07051 (Vernalis) claims aryl-isoxazole derivatives that can be used for treating pathologies associated with inhibition of the heat-shock proteins such as the Hsp90 chaperone.

Patent application WO2004/096212 (Vernalis) claims a third family of pyrazoles that can be used for treating pathologies associated with inhibition of the heat-shock proteins such as the Hsp90 chaperone.

Patent application WO2005/00300 (Vernalis) claims, more generally, 5-membered heterocycles, substituted with aryl radicals, that can be used for treating pathologies associated with inhibition of the heat-shock proteins such as the Hsp90 chaperone.

Patent application JP2005/225787 (Nippon Kayaku) claims another family of pyrazoles as Hsp90 inhibitors.

Application WO2006/018082 (Merck) claims another family of pyrazoles as Hsp90 inhibitors.

Patent application WO2005/00778 (Kyowa Hakko Kogyo) claims a family of benzophenone derivatives as Hsp90 inhibitors, useful for the treatment of tumours.

Patent application WO2005/06322 (Kyowa Hakko Kogyo) claims a family of resorcinol derivatives as Hsp90 inhibitors.

Patent application WO2005/051808 (Kyowa Hakko Kogyo) claims a family of derivatives of resorcinyl-benzoic acids as Hsp90 inhibitors. Patent applications WO2005/021552, WO2005/0034950, WO2006/08503, WO2006/079789 and WO2006/090094 (Vernalis) claim families of pyrimidothiophenes or pyridothiophenes that can be used for treating pathologies associated with inhibition of the heat-shock proteins such as the Hsp90 chaperone.

Application WO2006/010595 (Novartis) claims a family of indazoles as Hsp90 inhibitors.

Application WO2006/010594 (Novartis) claims a family of dihydrobenzimidazolones as Hsp90 inhibitors.

Patent application WO2006/055760 (Synta Pharma) claims a family of diaryl-triazoles as Hsp90 inhibitors.

Patent application WO2006/087077 (Merck) claims a family of (s-triazol-3-yl)phenols as Hsp90 inhibitors.

Patent application FR2882361 (Aventis) claims a family of 3-aryl-1,2-benzisoxazoles as Hsp90 inhibitors.

Patent application WO2006/091963 (Serenex) claims families of tetrahydroindolones and tetrahydroindazolone as Hsp90 inhibitors.

Patent application DE10200509440 (Merck) claims a family of thienopyridines as Hsp90 inhibitors.

Patent application WO2006/095783 (Nippon Kayaku) claims a family of triazoles as Hsp90 inhibitors.

Patent application WO2006101052 (Nippon Kayaku) claims a family of acetylenic derivatives as Hsp90 inhibitors.

Patent application WO2006105372 (Conforma Therapeutics) claims a family of alkynyl pyrrolo[2,3-d]pyrimidines as Hsp90 inhibitors.

Patent application WO2006101052 (Nippon Kayaku) claims a family of acetylenic derivatives as Hsp90 inhibitors.

Patent application WO2006105372 (Conforma Therapeutics) claims a family of alkynyl pyrrolo[2,3-d]pyrimidines as Hsp90 inhibitors.

SUMMARY OF THE INVENTION

The present invention relates to products of formula (I):

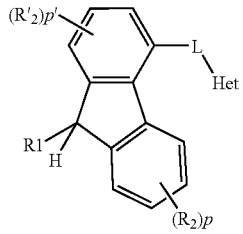

(I)

in which:
Het represents an aromatic or partially unsaturated heterocycle—of the dihydro or tetrahydro type—mono or bicyclic, with 5 to 11 ring members, containing from 1 to 4 heteroatoms, selected from N, O or S, optionally substituted with one or more radicals R, which may be identical or different, as described below, R is from the group comprising H, halogen, CF3, nitro, cyano, alkyl, hydroxy, mercapto, amino, alkylamino, dialkylamino, alkoxy, alkylthio, carboxy free or esterified by an alkyl, carboxamide, CO—NH(alkyl) and CON(alkyl)2, NH—CO-alkyl, NH—SO2-alkyl and heterocycloalkyl radical, all the alkyl, alkoxy, alkylthio and heterocycloalkyl radicals being optionally substituted, R1 is selected from the group comprising X-(A-B)n-CONH2, X-(A-B)n-O—CONH2, X-(A-B)n-NH—CONH2, X—(CH2)m-heterocycloalkyl, X—(CH2)m-aryl and X—(CH2)m-heteroaryl with X representing —O—C(O), —NH—C(O), NH—CS, —NH—CO—CH2—O—; —NH—CO—CH2—S—CH2—CO—NH—; —NH—CO—(CH2)2—SO2—; —NH—CO—CH2—N(CH3)—CO—; A and B, which may be identical or different, represent independently a single bond, CH2, CH-alkyl, CH-aralkyl, n=1, 2 and m=0, 1, R2 and R'2, which may be identical or different, are selected independently from the group comprising H, halogen, CF3, nitro, cyano, alkyl, hydroxy, mercapto, amino, alkylamino, dialkylamino, alkoxy, alkylthio (methylthio), carboxy free or esterified by an alkyl radical, carboxamide, CO—NH(alkyl) and NH—CO-alkyl, all the alkyl, alkoxy and alkylthio radicals being optionally substituted, p and p', which may be identical or different, represent respectively the integers 1 to 4 and 1 to 3;

L is selected from a single bond, CH2, C(O), O, S or NH, said products of formula (I) being in all possible tautomeric and isomeric forms: racemates, enantiomers and diastereoisomers, as well as salts of addition of said products of formula (I) with inorganic and organic acids or with inorganic and organic bases.

DETAILED DESCRIPTION OF THE INVENTION

The present invention relates notably to the products of formula (I) as defined above in which:

Het represents a mono or bicyclic heterocycle with 5 to 10 ring members containing from 1 to 3 heteroatoms, selected from N, O or S, optionally substituted with one or more radicals R, which may be identical or different, as described below, R is from the group comprising H, halogen, CF3, nitro, cyano, alkyl, hydroxy, mercapto, amino, alkylamino, dialkylamino, alkoxy, methylthio, carboxy free or esterified by an alkyl, carboxamide, CO—NH(alkyl) and CON(alkyl)2, NH—CO-alkyl, NH—SO2-alkyl and heterocycloalkyl radical, all the alkyl, alkoxy, alkylthio and heterocycloalkyl radicals being optionally substituted;

R1 represents NH—(CH2)2-O—CONH2; NH—(CH2)3-O—CONH2; NH—(CH2)3CONH2; NH—(CH2)4-CONH2; or R1 represents the radical —X—(CH2)m-heteroaryl with X representing —O—C(O), —NH—C(O), NH—CS, —NH—CO—CH2-O—; —NH—CO—CH2-S—CH2-CO—NH—; —NH—CO—(CH2)$_2$—SO2- or —NH—CO—CH2-N(CH3)-CO— and m=0, 1, these heteroaryl radicals being optionally substituted with one or more radicals, which may be identical or different, selected from halogen atoms, hydroxyl, alkyl radicals containing from 1 to 4 carbon atoms, and the NH2, NHalk and CONH2 radicals;

R2 and R'2, which may be identical or different, are selected independently from the group comprising H, halogen atoms and the amino radical;

p and p', which may be identical or different, represent respectively the integers 1;

L represents a single bond and C(O), said products of formula (I) being in all possible tautomeric and isomeric forms: racemates, enantiomers and diastereoisomers, as well as salts of addition of said products of formula (I) with inorganic and organic acids or with inorganic and organic bases.

In the products of formula (I) as defined above and below, all the alkyl, alkoxy, alkylthio, cycloalkyl, heterocycloalkyl, aryl, phenyl and heteroaryl radicals are optionally substituted with one or more radicals, which may be identical or different, selected from halogen atoms; the radicals hydroxyl; cyano; mercapto; nitro; carboxy free, salified or esterified; tetrazolyl; —NH2, —NH(alk), —N(alk)(alk); —SO2-NH—CO—NH-alkyl; —SO2-NH—CO—NH-phenyl; COalkyl, CONH2, O—C(O)—NH2, O—C(O)-alk, —C(O)—NH (alk); —C(O)—N(alk)(alk), CO—NH-alk-O-alk, —NH—C(O)-(alk), —N(alk)-C(O)-(alk); —NH—COOalkyl, NH—CO—NH2, alkyl, acyl; alkylthio, cycloalkyl, heterocycloalkyl, aryl, heteroaryl, alkoxy and phenoxy themselves optionally substituted with one or more radicals selected from halogen atoms and the hydroxyl, alkoxy, alkyl, —NH2, —NH(alk) and —N(alk)(alk) radicals.

In the products of formula (I) and hereinafter, the terms used have the following meanings:

the term halogen denotes the atoms of fluorine, of chlorine, of bromine or of iodine and preferably of fluorine, chlorine or bromine.

the term alkyl radical denotes a linear or branched radical containing at most 12 carbon atoms selected from the methyl, ethyl, propyl, isopropyl, butyl, isobutyl, sec-butyl, tert-butyl, pentyl, isopentyl, sec-pentyl, tert-pentyl, neo-pentyl, hexyl, isohexyl, sec-hexyl, tert-hexyl and also heptyl, octyl, nonyl, decyl, undecyl and dodecyl radicals, as well as their linear or branched positional isomers. We may mention more particularly the alkyl radicals having at most 6 carbon atoms and notably the radicals methyl, ethyl, propyl, isopropyl, n-butyl, isobutyl, tert-butyl, pentyl linear or branched, hexyl linear or branched.

the term alkoxy radical denotes a linear or branched radical containing at most 12 carbon atoms and preferably 6 carbon atoms selected for example from the methoxy, ethoxy, propoxy, isopropoxy; linear, secondary or tertiary butoxy; pentoxy, hexoxy and heptoxy radicals as well as their linear or branched positional isomers.

the term alkylthio or alkyl-S— denotes a linear or branched radical containing at most 12 carbon atoms and notably represents the methylthio, ethylthio, isopropylthio and heptylthio radicals. In the radicals bearing a sulphur atom, the sulphur atom can be oxidized to the SO or S(O)2 radical.

the term acyl or r-CO— radical denotes a linear or branched radical containing at most 12 carbon atoms in which the radical r represents a hydrogen atom, an alkyl, cycloalkyl, cycloalkenyl, cycloalkyl, heterocycloalkyl or aryl radical, these radicals having the values stated above and being optionally substituted as indicated: we may mention for example the formyl, acetyl, propionyl, butyryl or benzoyl radicals, or the valeryl, hexanoyl, acryloyl, crotonoyl or carbamoyl radicals, the term cycloalkyl radical denotes a monocyclic or bicyclic carbocyclic radical containing from 3 to 10 ring members and notably denotes the cyclopropyl, cyclobutyl, cyclopentyl and cyclohexyl radicals, the term cycloalkylalkyl radical denotes a radical in which cycloalkyl and alkyl are selected from the values stated above: this radical thus denotes for example the cyclopropylmethyl, cyclopentylmethyl, cyclohexylmethyl and cycloheptylmethyl radicals, by acyloxy radical, we mean the acyl-O— radicals in which acyl has the meaning stated above: we may mention for example the acetoxy or propionyloxy radicals, by acylamino radical, we mean the acyl-N— radicals in which acyl has the meaning stated above, the term aryl radical denotes the unsaturated radicals, monocyclic or comprising condensed rings, carbocyclic. We may mention, as examples of said aryl radical, the phenyl or naphthyl radicals, by arylalkyl we mean the radicals resulting from combination of the alkyl radicals mentioned previously, optionally substituted, and the aryl radicals also mentioned above, optionally substituted: we may mention for example the benzyl, phenylethyl, 2-phenethyl, triphenylmethyl or naphthalenemethyl radicals, the term heterocyclic radical denotes a carbocyclic radical, saturated (heterocycloalkyl) or partially or totally unsaturated (heteroaryl), comprising 4 to 10 ring members interrupted by one or more heteroatoms, which may be identical or different, selected from the oxygen, nitrogen or sulphur atoms.

As heterocycloalkyl radicals, we may mention notably the dioxolane, dioxane, dithiolane, thiooxolane, thiooxane, oxiranyl, oxolanyl, dioxolanyl, piperazinyl, piperidyl, pyrrolidinyl, imidazolidinyl, imidazolidine-2,4-dione, pyrazolidinyl, morpholinyl radicals or the tetrahydrofuryl, hexahydropyran, tetrahydrothienyl, chromanyl, dihydrobenzofuranyl, indolinyl, perhydropyranyl, pyrindolinyl, tetrahydroquinolinyl, tetrahydroisoquinolinyl or thioazolidinyl radicals, all said radicals being optionally substituted.

Among the heterocycloalkyl radicals, we may mention notably the radicals piperazinyl optionally substituted, N-methylpiperazinyl, piperidyl, optionally substituted, pyrrolidinyl optionally substituted, imidazolidinyl, pyrazolidinyl, morpholinyl, hexahydropyran or thioazolidinyl.

By heterocycloalkylalkyl radical, we mean the radicals in which the heterocycloalkyl and alkyl residues have the meanings stated previously;

among the heteroaryl radicals with 5 ring members we may mention the furyl, pyrrolyl, tetrazolyl, thiazolyl, isothiazolyl, diazolyl, thiadiazolyl, thiatriazolyl, oxazolyl, oxadiazolyl, isoxazolyl, imidazolyl, pyrazolyl, thienyl, triazolyl radicals.

Among the heteroaryl radicals with 6 ring members we may mention notably the pyridyl radicals such as 2-pyridyl, 3-pyridyl and 4-pyridyl, pyrimidyl, pyridazinyl, pyrazinyl.

As condensed heteroaryl radicals containing at least one heteroatom selected from sulphur, nitrogen and oxygen, we may mention for example benzothienyl, benzofuryl, benzopyrrolyl, benzothiazolyl, benzimidazolyl, imidazopyridyl, purinyl, pyrrolopyrimidinyl, pyrrolopyridinyl, benzoxazolyl, benzisoxazolyl, benzisothiazolyl, thionaphthyl, chromenyl, indolizinyl, quinazolinyl, quinoxalinyl, indolyl, indazolyl, purinyl, quinolyl, isoquinolyl and naphthyridinyl.

By alkylamino radical, we mean the radicals in which the alkyl radical is selected from the alkyl radicals mentioned above. The alkyl radicals having at most 4 carbon atoms are preferred, and we may mention for example the radicals methylamino, ethylamino, propylamino or butylamino, linear or branched.

By dialkylamino radical, we mean the radicals in which the alkyl radicals, which may be identical or different, are selected from the alkyl radicals mentioned above. As previously, alkyl radicals having at most 4 carbon atoms are preferred, and we may mention for example the radicals dimethylamino, diethylamino, methylethylamino linear or branched.

The term patient denotes both human beings and other mammals.

The term "prodrug" denotes a product which can be transformed in vivo by metabolic mechanisms (such as hydrolysis) to a product of formula (I). For example, an ester of a product of formula (I) containing a hydroxyl group can be converted by hydrolysis in vivo to its parent molecule; or an ester of a product of formula (I) containing a carboxy group can be converted by hydrolysis in vivo to its parent molecule.

We may mention, as examples, esters of products of formula (I) containing a hydroxyl group such as the acetates, citrates, lactates, tartrates, malonates, oxalates, salicylates, propionates, succinates, fumarates, maleates, methylene-bis-b-hydroxynaphthoates, gentisates, isethionates, di-p-toluoyl-tartrates, methanesulphonates, ethanesulphonates, camphorsulphonates, benzenesulphonates, p-toluenesulphonates, cyclohexyl-sulphamates and quinates.

Particularly useful esters of products of formula (I) containing a hydroxyl group can be prepared from acid residues such as those described by Bundgaard et al., J. Med. Chem., 1989, 32, page 2503-2507: these esters notably include substituted (aminomethyl)-benzoates and dialkylamino-methylbenzoates in which the two alkyl groups can be joined together or can be interrupted by an oxygen atom or by a nitrogen atom optionally substituted i.e. an alkylated nitrogen atom or (morpholino-methyl)benzoates, e.g. 3- or 4-(morpholinomethyl)-benzoates, and (4-alkylpiperazin-1-yl)benzoates, e.g. 3- or 4-(4-alkylpiperazin-1-yl)benzoates.

The carboxy radical or radicals of the products of formula (I) can be salified or esterified by the various groups known by a person skilled in the art, among which we may mention, as non-limiting examples, the following compounds.

among the compounds of salification, inorganic bases such as, for example, an equivalent of sodium, of potassium, of lithium, of calcium, of magnesium or of ammonium or organic bases such as, for example, methylamine, propylamine, trimethylamine, diethylamine, triethylamine, N,N-dimethylethanolamine, tris(hydroxymethyl)aminomethane, ethanolamine, pyridine, picoline, dicyclohexylamine, morpholine, benzylamine, procaine, lysine, arginine, histidine, N-methylglucamine, among the compounds of esterification, alkyl radicals to form alkoxy carbonyl groups such as, for example, methoxycarbonyl, ethoxycarbonyl, tert-butoxy-carbonyl or benzyloxycarbonyl, and said alkyl radicals can be substituted with radicals selected for example from halogen atoms, the hydroxyl, alkoxy, acyl, acyloxy, alkylthio, amino or aryl radicals, for example, from the chloromethyl, hydroxypropyl, methoxymethyl, propionyloxymethyl, methylthiomethyl, dimethyl-aminoethyl, benzyl or phenethyl groups.

By esterified carboxy, we mean for example radicals such as the alkyloxycarbonyl radicals, for example methoxycarbonyl, ethoxycarbonyl, propoxycarbonyl, butyl or tert-butyloxycarbonyl, cyclobutyloxycarbonyl, cyclopentyloxycarbonyl or cyclohexyloxycarbonyl.

We may also mention radicals formed with the ester residues that are easily cleaved, such as the methoxymethyl, ethoxymethyl radicals; the acyloxyalkyl radicals such as pivaloyloxymethyl, pivaloyloxyethyl, acetoxymethyl or acetoxyethyl; the alkyloxycarbonyloxy alkyl radicals such as the methoxycarbonyloxy methyl or ethyl radicals, the isopropyloxycarbonyloxy methyl or ethyl radicals.

A list of such ester radicals may be found for example in European patent EP 0 034 536.

By amidated carboxy, we mean the radicals of the type —CONH2 whose hydrogen atoms are optionally substituted with one or two alkyl radicals to form alkylamino or dialkylamino radicals, themselves optionally substituted as indicated above or below, and said radicals can also form, with the nitrogen atom to which they are attached, a cyclic amine as defined above.

By salified carboxy, we mean the salts formed for example with an equivalent of sodium, of potassium, of lithium, of calcium, of magnesium or of ammonium. We may also mention the salts formed with organic bases such as methylamine, propylamine, trimethylamine, diethylamine, triethylamine. The sodium salt is preferred.

When the products of formula (I) bear an amino radical that is salifiable by an acid, said salts of acids also of course form part of the invention. We may mention the salts supplied with hydrochloric acid or methanesulphonic acid, for example.

The salts of addition of the products of formula (I) with inorganic or organic acids can be, for example, the salts formed with hydrochloric, hydrobromic, hydriodic, nitric, sulphuric, phosphoric, propionic, acetic, trifluoroacetic, formic, benzoic, maleic, fumaric, succinic, tartaric, citric, oxalic, glyoxylic, aspartic, ascorbic acids, the alkylmonosulphonic acids such as for example methanesulphonic acid, ethanesulphonic acid, propanesulphonic acid, the alkyldisulphonic acids such as for example methanedisulphonic acid, alpha, beta-ethanedisulphonic acid, the arylmonosulphonic acids such as benzenesulphonic acid and the aryldisulphonic acids.

It will be recalled that stereoisomerism can be defined broadly as the isomerism of compounds having identical structural formulae, but with the various groups arranged differently in space, such as notably in monosubstituted cyclohexanes in which the substituent can be in an axial or equatorial position, and the various possible rotational conformations of the derivatives of ethane. However, there is another type of stereoisomerism, resulting from different spatial arrangements of substituents attached either to double bonds, or to rings, which is often called geometric isomerism or cis-trans isomerism. The term stereoisomer is used in the present application in its broadest sense and therefore relates to all of the compounds stated above.

The present invention relates in particular to the products of formula (I) as defined in any one of the preceding claims in which Het is selected from the imidazolyl, benzofuranyl, quinolinyl, pyridinyl, indolyl, benzoxazolyl, pyrimidinyl, triazolopyridinyl, benzoxazinyl, quinoxalinyl, indazolyl, pyrrolopyridinyl, tetrahydro-1,8-naphthyridinyl, imidazopyridinyl radicals; said radicals being optionally substituted with one or more radicals R, which may be identical or different, selected from halogen atoms and the cyano and morpholino radicals;

R1 represents the radical —NH—C(O)-heteroaryl, with heteroaryl selected from the radicals quinolyl, pyridyl, purines, quinoxaline, pyrazole, pyrimidinyl, pyrrolo[2,3-b]pyridine, pyrrolo[2,3-c]pyrimidine, imidazo[4,5-b]pyridine, these heteroaryl radicals being optionally substituted with one or more radicals, which may be identical or different, selected from halogen atoms, the methyl, ethyl, NH2, Nhalk and NH-Me radicals, R2 and R'2, represent H, L represents a single bond or C(O), said products of formula (I) being in all possible tautomeric and isomeric forms: racemates, enantiomers and diastereoisomers, as well as salts of addition of said products of formula (Ib) with inorganic and organic acids or with inorganic and organic bases.

The present invention thus relates more particularly to the products of formula (I) as defined above in which Het, R2, R'2, p, p' and L have any one of the meanings defined above and R1 is selected from the following radicals:

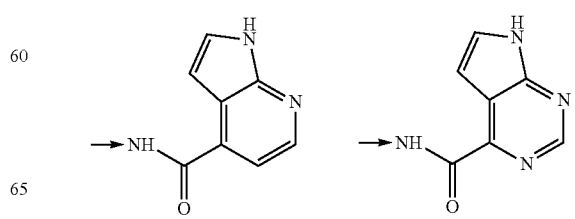

-continued
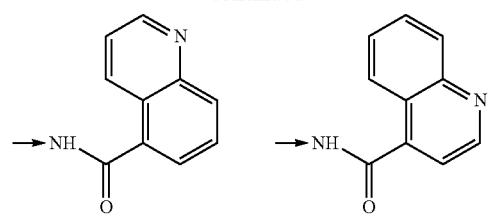
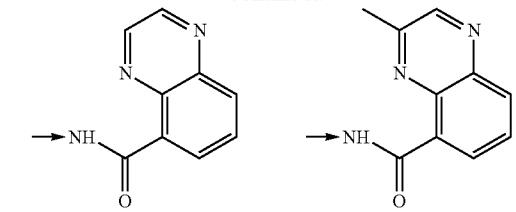
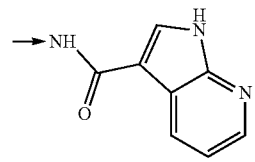
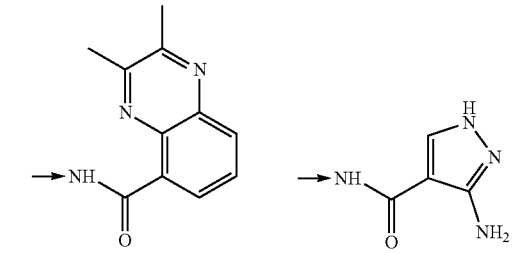
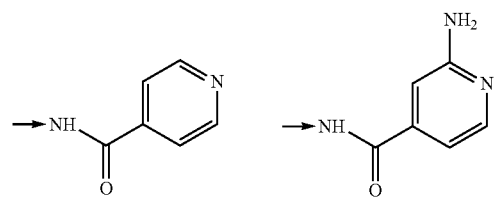
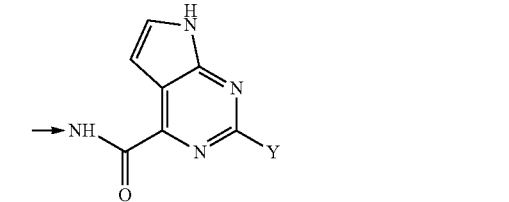
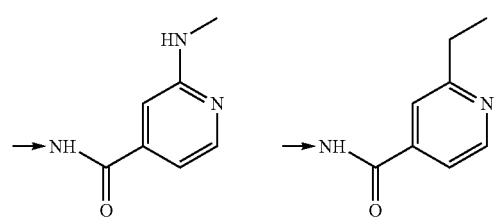
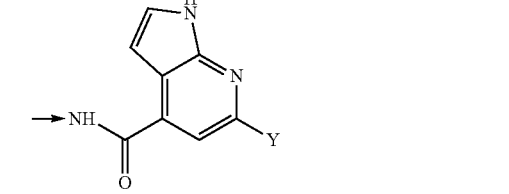
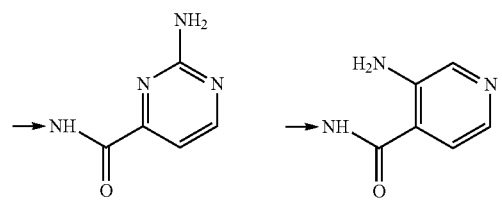
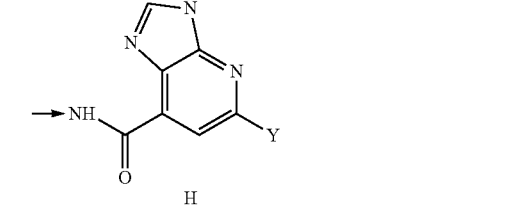
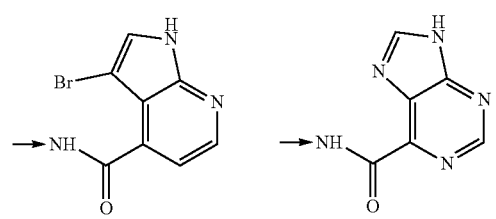
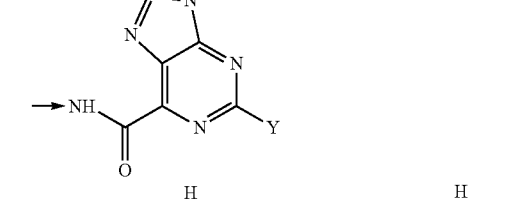
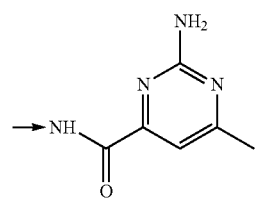
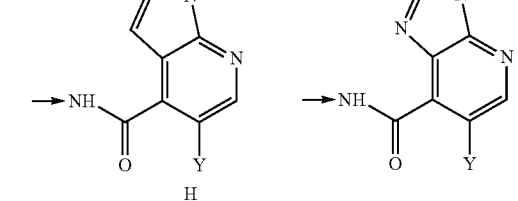
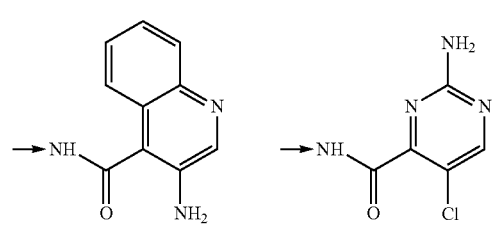
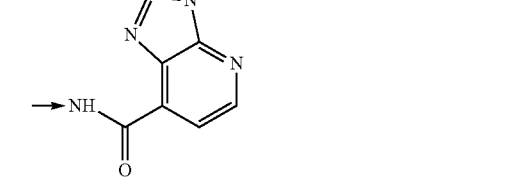

with Y representing a halogen atom or a methyl or ethyl radical, said products of formula (I) being in all possible tautomeric and isomeric forms: racemates, enantiomers and diastereoisomers, as well as salts of addition of said products of formula (I) with inorganic and organic acids or with inorganic and organic bases.

The present invention relates quite particularly to the products of formula (I) as defined above that have the following names:

[4-(1H-imidazol-2-yl)-9H-fluoren-9(R,S)-yl]-amide of 2-amino-5-chloro-pyrimidine-4-carboxylic acid

[4-(benzofuran-2-yl)-9H-fluoren-9(R,S)-yl)]-amide of 1H-pyrrolo[2,3-b]pyridine-4-carboxylic acid.

[4-(quinolin-3-yl)-9H-fluoren-9(R,S)-yl)]-amide of 1H-pyrrolo[2,3-b]pyridine-4-carboxylic acid

[4-(6-fluoro-pyridin-3-yl)-9H-fluoren-9-(R,S)-yl]-amide of 1H-pyrrolo[2,3b]pyridine-4-carboxylic acid.

[4-(1H-indol-2-yl)-9H-fluoren-9-(R,S)-yl]-amide of 1H-pyrrolo[2,3-b]pyridine-4-carboxylic acid

[4-(benzoxazol-2-yl)-9H-fluoren-9-(R,S)-yl]-amide of 1H-pyrrolo[2,3-b]pyridine-4-carboxylic acid

[4-(pyrimidin-5-yl)-9H-fluoren-9-(R,S)yl]-amide of 1H-pyrrolo[2,3-b]pyridine-4-carboxylic acid

[4-(quinolin-2-yl)-9H-fluoren-9-(R,S)-yl]-amide of 1H-pyrrolo[2,3-b]pyridine-4-carboxylic acid (4-[1.2.4]triazolo[1,5-a]pyridin-2-yl-9H-fluoren-9(R,S)-yl)-amide of 1H-pyrrolo[2,3-b]pyridine-4-carboxylic acid

[4-(1,4-benzoxazin-2H-3-yl)-9H-fluoren-9(R,S)-yl]-amide of 1H-pyrrolo[2,3-b]pyridine-4-carboxylic acid

[4-(quinolin-3-yl)-9H-fluoren-9(R,S)-yl]-amide of 7H-pyrrolo[2,3-c]pyrimidine-4-carboxylic acid

[4-(quinoxalin-2-yl)-9H-fluoren-9(R,S)-yl]-amide of 1H-pyrrolo[2,3-b]pyridine-4-carboxylic acid

[4-(quinolin-3-yl)-9H-fluoren-9(R,S)-yl]-amide of 6-bromo-3H-imidazo[4,5-b]pyridine-7-carboxylic acid

[4-(2-morpholino-pyridin-5-yl)-9H-fluoren-9(R,S)-yl]-amide of 1H-pyrrolo[2,3-b]pyridine-4-carboxylic acid

[4-(quinolin-3-yl)-9H-fluoren-9(R,S)-yl]-amide of 2-amino-5-chloro-pyrimidine-4-carboxylic acid

[4-(indazole-1-carbonyl)-9H-fluoren-9(R,S)-yl]-amide of 1H-pyrrolo[2,3-b]pyridine-4-carboxylic acid

[4-(1H-pyrrolo[2,3-b]pyridin-5-yl)-9H-fluoren-9(R,S)-yl]-amide of 1H-pyrrolo[2,3-b]pyridine-4-carboxylic acid 4-(5,6,7,8-tetrahydro-1,8-naphthyridin-3-yl)-9H-fluoren-9(R,S)-yl]-amide of 1H-pyrrolo[2,3-b]pyridine-4-carboxylic acid 4-{imidazo[1,2-a]pyridin-2-yl}-9H-fluoren-9-(R,S)-yl-amide of 1H-pyrrolo[2,3-b]pyridine-4-carboxylic acid dextrorotatory enantiomer of [4-(quinolin-3-yl)-9H-fluoren-9(R,S)-yl]-amide of 6-bromo-3H-imidazo[4,5-b]pyridine-7-carboxylic acid said products of formula (I) being in all possible isomeric forms: racemates, enantiomers and diastereoisomers, as well as salts of addition with inorganic and organic acids or with inorganic and organic bases.

The present invention thus relates to the products of formula (I) corresponding to formula (Ia) in which L represents a single bond and the products of formula (I) corresponding to formula (Ib) in which L represents CH2, C(O), O, S or NH represented as follows:

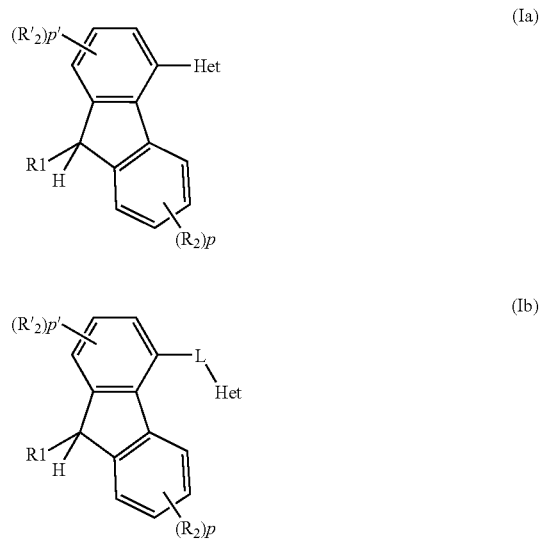

in which Het, R1, R2, R2', p and p' have the values defined above for the products of formula (I)

said products of formula (Ia) or (Ib) being in all possible tautomeric and isomeric forms: racemates, enantiomers and diastereoisomers, as well as salts of addition of said products of formula (Ia) or (Ib) with inorganic and organic acids or with inorganic and organic bases.

The products of formula (I) corresponding to formula (Ia) or (Ib) according to the present invention can be prepared according to the methods known by a person skilled in the art and in particular according to the methods described below: the present invention thus also relates to the methods of syntheses of the products of formula (Ia) or (Ib) according to the present invention and notably the general methods of syntheses described in the schemes given below.

General Methods of Syntheses of the Products of General Formula (Ia):

Coupling Reaction Starting from a 4-Halo-Fluoren-9-One:

A first general method of synthesis comprises coupling a 9H-4-halo-fluoren-9-one—such as 9H-4-bromo-fluoren-9-one, which can be obtained according to J. Amer. Chem. Soc. 1935, 2443-6 or 9H-4-iodo-fluoren-9-one, which can be obtained according to Helv. Chim. Acta 1973, 3044-9—or the triflate of 9-H-4-hydroxy-fluoren-9-one with an organometallic derivative of a heterocycle, according to Scheme 1:

Scheme 1

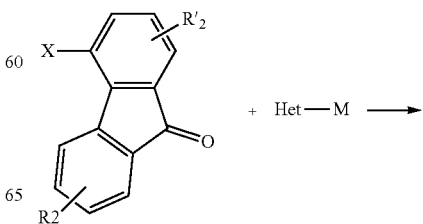

-continued

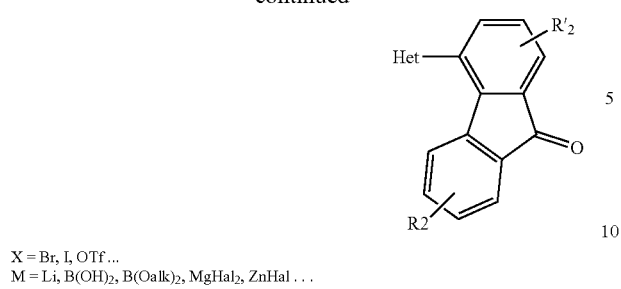

X = Br, I, OTf ...
M = Li, B(OH)$_2$, B(Oalk)$_2$, MgHal$_2$, ZnHal ...

Within the scope of the invention, it is particularly advantageous to use a boronic acid as organometallic derivative of a heterocycle.

Within the scope of the invention, it is particularly advantageous to carry out the coupling in the presence of a catalyst derived from palladium (0), in the conditions of a reaction of the Suzuki type.

Coupling reaction starting from an organometallic derivative of fluoren-9-on-4-yl: In a second general method of synthesis, reverse coupling can be envisaged, in particular using a bromine-containing or iodine-containing heterocycle and an organometallic derivative of fluoren-9-one, such as 9-oxofluorene-4-boronic acid or one of its esters, according to Scheme 2:

Scheme 2

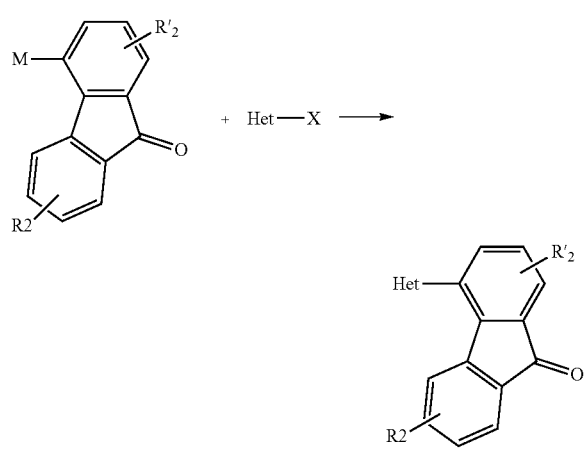

X = Br, I, OTf ...
M = Li, B(OH)$_2$, B(Oalk)$_2$, MgHal$_2$, ZnHal ...

Formation of the Heterocycle from an Acid or Aldehyde Derivative of fluoren-9-on-4-yl:

In a third general method of synthesis, when said heterocycle is of the benzimidazole, benzoxazole, or benzothiazole type, attached to the fluorene derivative in its position 2, it is particularly advantageous to form said heterocycle by coupling a derivative of orthophenylenediamine or of orthoaminophenol or of orthoaminothiophenol with an acid, an acid chloride or an aldehyde in position 4 of a fluoren-9-one, followed by cyclization, according to Scheme 3:

Scheme 3

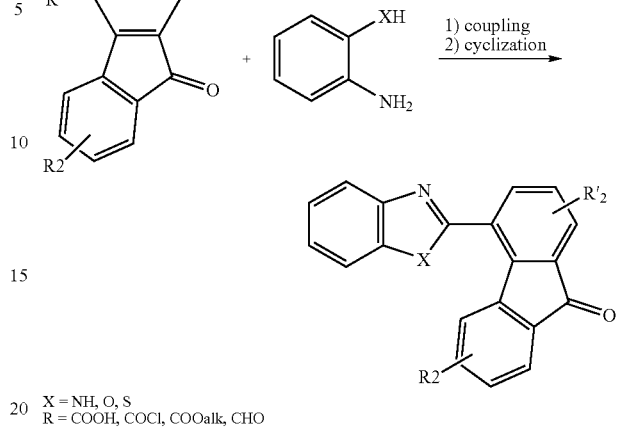

X = NH, O, S
R = COOH, COCl, COOalk, CHO

When a fluoren-9-one-4-carboxylic acid is used, it is particularly advantageous to activate this acid by means of a coupling agent known by a person skilled in the art, such as 1-(3-dimethylaminopropyl)-3-ethylcarbodiimide hydrochloride (EDCI), in the presence of 1-hydroxybenzotriazole (HOBT).

Various conditions of cyclization of the mixture of intermediate amides can be used within the scope of the invention, such as acetic acid or a mixture of trifluoroacetic acid and anhydride. It is also particularly advantageous within the scope of the invention to carry out this type of thermal cyclization in an acid environment by heating in a microwave reactor.

When a derivative of fluoren-9-one-4-carboxaldehyde is used, it is advantageous, within the scope of the invention, to work:

either by microwave heating in the presence of silica, according to Tetrahedron Lett. 1998, 39, 4481-84;

or in the presence of dichloro-dicyano-benzoquinone (DDQ), according to Tetrahedron 1995, 51, 5813-18;

or in the presence of a mixture of thionyl chloride and pyridine, according to E.P. 511187;

or in the presence of ferric chloride, according to Eur. J. Med. Chem. 2006, 31, 635-42.

When said heterocycle is of the imidazole, oxazole, or thiazole type, attached to the fluorene derivative in its position 2, it is particularly advantageous to form said heterocycle from an acid, an acid chloride, an ester or an aldehyde in position 4 of a fluoren-9-one, working according to Scheme 4:

Scheme 4

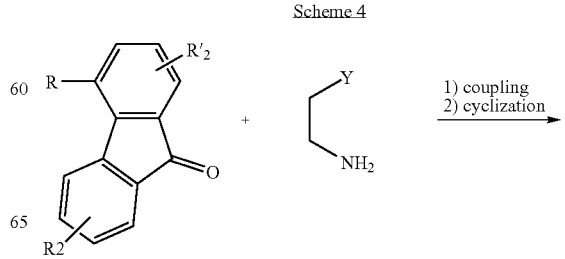

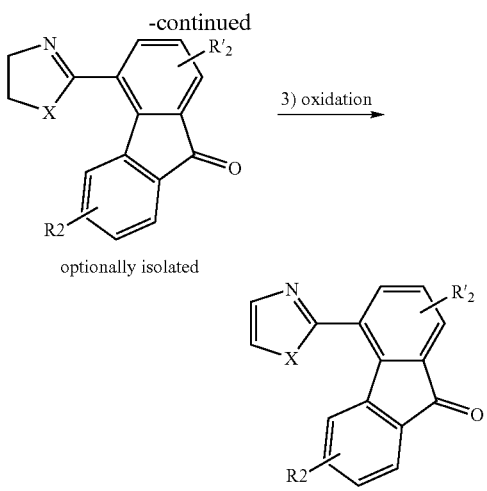

X = NH, O, S
Y = X or a group/reactant which is a precursor of X
R = COOH, COCl, COOalk, CHO Within the scope of the invention it is particularly advantageous to work:
1. in the case when said heterocycle is an imidazole or an imidazoline:
   from a 2-azido-ethylamine, according to Tetrahedron, 47(38), 1991, 8177-94,
   from an ethylenediamine, according to Biorg. Med. Chem. Lett. 12(3), 2002, 471-75,
   from glyoxal and from ammonia, according to J. Med. Chem., 46(25), 2003, 5416-27;
2. in the case when said heterocycle is an oxazole or an oxazoline:
   from a 2-azido-ethanol, according to J. Org. Chem., 61(7), 1996, 2487-96,
   from a 2-aminoethanol, according to J. Med. Chem. 47(8), 2004, 1969-86 or Khim. Geterotsikl. Soed. 1984(7), 881-4,
   from diethylacetal of 2-aminoacetaldehyde, according to Heterocycles, 39(2), 1994, 767-78;
3. in the case when said heterocycle is thiazole or a thiazoline:
   from a 2-chloro-ethylamine and a Lawesson reagent, according to Helv. Chim. Acta, 88(2), 2005, 187-95,
   from a 2-aminoethanethiol, according to J. Org. Chem. 69(3), 2004, 811-4, or Tetrahedron Lett., 41(18), 2000, 3381-4.

More generally, it is advantageous, within the scope of the invention, to form any heterocycle from an acid, an acid chloride of an ester or of an aldehyde in position 4 of a fluoren-9-one, by any one of the methods of synthesis known by a person skilled in the art, such as those described in Comprehensive Organic Chemistry, by D. Barton et al. (Pergamon Press) or Advances in Heterocyclic Chemistry (Academic Press) or Heterocyclic Compounds (Wiley Interscience).

The transformation of the C=O radical to CHR1 radicals as defined in general formula (Ia) can be effected according to the general methods known by a person skilled in the art, in particular those described in Comprehensive Organic Chemistry, by D. Barton et al. (Pergamon Press), Advanced Organic Chemistry, by J. Marsh (Wiley Interscience), or Compendium of Organic Synthetic Methods (Wiley Interscience).

Coupling reaction starting from a brominated or organometallic derivative of fluoren-4-yl substituted in position 9 with a CHR1 radical: A fourth general method of synthesis comprises first carrying out the transformation of the C=O radical of a fluoren-9-one derivative, substituted in position 4 with a halogen, a triflate, a boronate or a boronic 9-oxo-fluorene-4-carboxylic acid, to a CHR1 radical, as defined in general formula (Ia), then coupling the derivative obtained with a heterocycle derivative suitably substituted with a halogen, a boronate or boronic acid.

Formation of the heterocycle from an acid or aldehyde derivative of fluoren-4-yl substituted in position 9 with a CHR1 radical: A fifth general method of synthesis comprises forming the heterocycle after previously introducing the CHR1 radical on an acid, an ester, an acid chloride or an aldehyde in position 4 of the fluorene nucleus.

When said heterocycle is of the benzimidazole, benzoxazole, or benzothiazole type, attached to the fluorene derivative in its position 2, it is advantageous first to carry out the transformation of the C=O radical of a fluoren-9-one derivative, substituted in position 4 with a carboxylic acid derivative—acid, acid chloride or ester—or with an aldehyde, to a CHR1 radical, as defined in general formula (I), then coupling the derivative obtained with a derivative of o-phenylenediamine or of o-aminophenol or of o-aminothiophenol, according to the conditions described previously.

When said heterocycle is of the imidazole, oxazole, or thiazole type, attached to the fluorene derivative in its position 2, it is advantageous first to carry out the transformation of the C=O radical of a fluoren-9-one derivative, substituted in position 4 with a carboxylic acid derivative—acid, acid chloride or ester—or with an aldehyde, to a CHR1 radical, as defined in general formula (I), and then form the heterocycle according to the methods described previously.

More generally, it is advantageous, within the scope of the invention, to form any heterocycle starting from an acid, an acid chloride of an ester or of an aldehyde in position 4 of a fluorene nucleus substituted in position 9 with a CHR1 radical, by any one of the methods of synthesis known by a person skilled in the art, such as those described in Comprehensive Organic Chemistry, by D. Barton et al. (Pergamon Press) or Advances in Heterocyclic Chemistry (Academic Press) or Heterocyclic Compounds (Wiley Interscience).

Preparation of the Compounds of General Formula (Ib) in which L=Co

The compounds of general formula (Ib), in which L=CO, and for which the heterocycle Het is attached via a carbon atom, can be prepared advantageously by a reaction of the Friedel-Crafts type according to Scheme 6:
either by the action of a fluoren-9-one-4-carboxylic acid or acid chloride on a heterocycle sufficiently rich in electrons, notably according to the method described in Eur. J. Med. Chem. 1988, 23(2), 165-72;
or by the action of a heterocyclic acid chloride on a derivative of fluoren-9-one.

Scheme 6

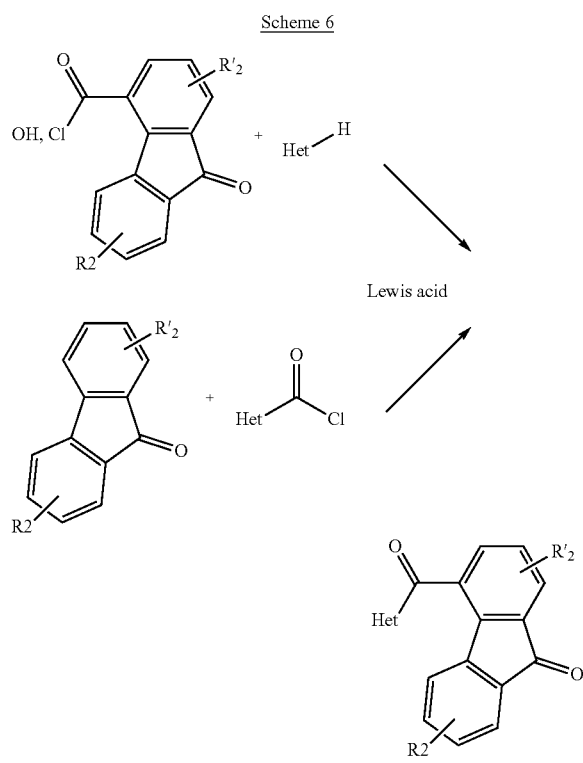

The compounds of general formula (Ib) in which L=CO, and for which the heterocycle Het is attached via a nitrogen atom, such as the heterocycles of the pyrrole, pyrazole, imidazole, indole, isoindole, indazole, benzimidazole or imidazo [4,3-c]pyridine type, can be prepared advantageously by coupling an anion derived from said heterocycle with a fluoren-9-one-4-carboxylic acid chloride according to Scheme 7:

Scheme 7

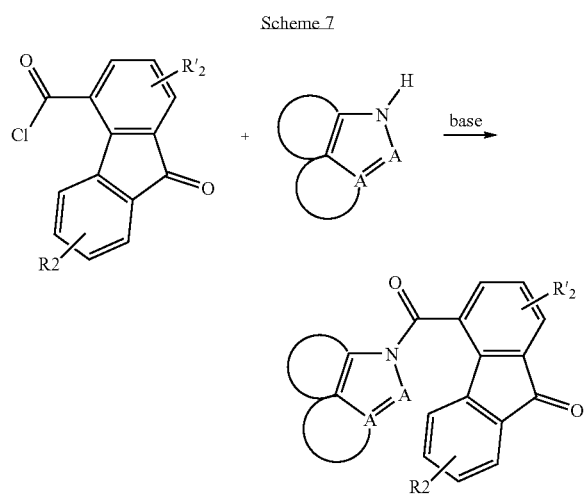

The compounds of general formula (Ib) in which L=CH2 can be prepared advantageously according to one of the general methods described in Scheme 8,
either by coupling between a derivative of 4-halomethyl-fluoren-9-one and a heterocyclic organic compound;
or by cyclization between a derivative of (fluoren-9-on-4-yl)acetic acid and an aromatic or heteroaromatic ortho-disubstituted nucleus:

Scheme 8

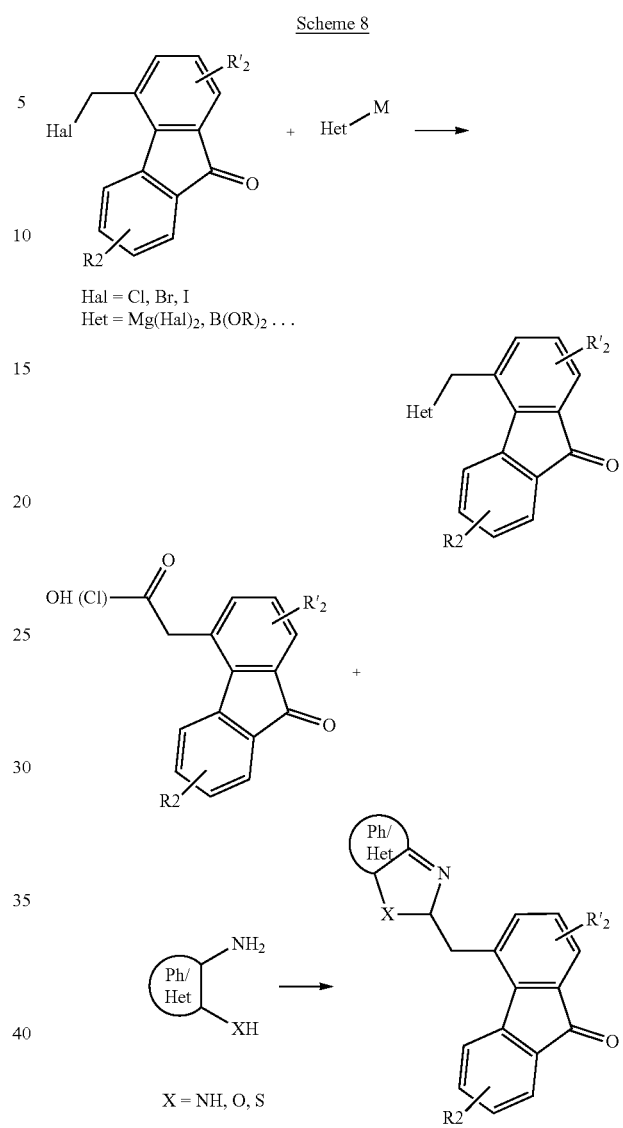

Hal = Cl, Br, I
Het = Mg(Hal)$_2$, B(OR)$_2$ . . .

X = NH, O, S

The compounds of general formula (Ib) in which L=O can be prepared according to any one of the general methods of synthesis of aryl(heteroaryl)ethers known by a person skilled in the art, notably those using catalysis with copper iodide, starting from:
either a 4-halo-fluoren-9-one and an alkaline salt of a hydroxy-heterocycle;
or an alkaline salt of 4-hydroxy-fluoren-9-one and a heteroaryl halide.

The compounds of general formula (Ib) in which L=S can be prepared according to any one of the general methods of synthesis of aryl(heteroaryl)thioethers known by a person skilled in the art, notably those using catalysis with palladium acetate, starting from:
either a 4-halo-fluoren-9-one and an alkaline salt of a mercapto-heterocycle;
or an alkaline salt of 4-mercapto-fluoren-9-one and a heteroaryl halide.

The transformation of the C=O radical to CHR1 radicals as defined in general formula (Ib) in which L=CO, CH2, O and S can be effected according to the general methods known by a person skilled in the art, in particular those described in Comprehensive Organic Chemistry, by D. Barton et al. (Pergamon Press), Advanced Organic Chemistry, by J. Marsh (Wiley Interscience), or Compendium of Organic Synthetic Methods (Wiley Interscience), according to Scheme 9:

For preparing the compounds of general formula (Ib) in which L=NH, it is particularly advantageous, within the scope of the invention, to reverse the order of the reactions, first transforming the C=O radical to a CHR1 radical, from a derivative of 4-nitro-fluoren-9-one, then reducing the nitro group to a primary amine function, and finally carrying out a heteroarylation of said primary amine with a heterocyclic bromide or iodide in the presence of palladium(0), in the conditions of the Hartwig-Buchwald reaction, according to General Scheme 10:

General Scheme 10

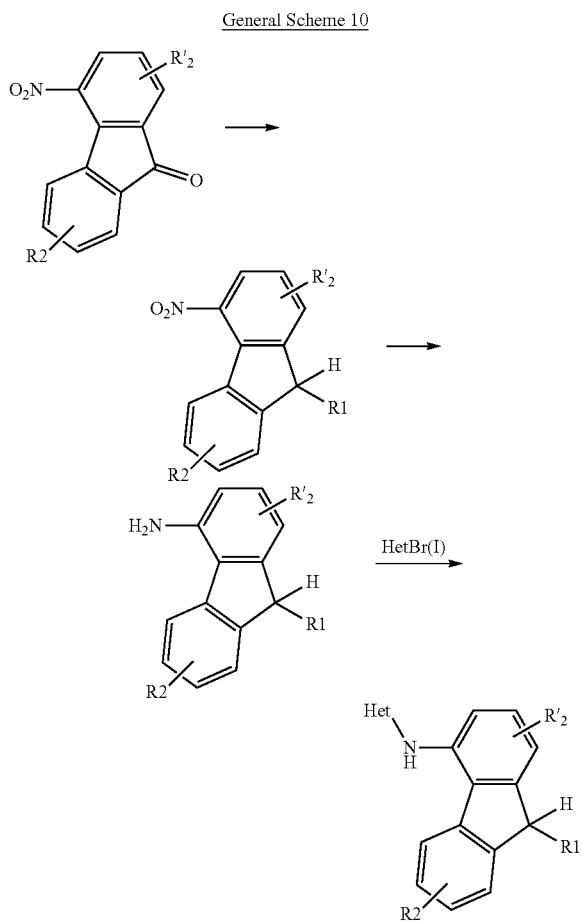

The reactions described above can be carried out according to the conditions described in the preparation of the examples given below and also according to the general methods known by a person skilled in the art, in particular those described in: Comprehensive Organic Chemistry, by D. Barton et al. (Pergamon Press); Advanced Organic Chemistry, by J. Marsh (Wiley Interscience).

The products according to the present invention possess interesting pharmacological properties: notably, it was found that they possess properties of inhibiting the activities of the chaperone proteins and notably their ATPase activities.

Among these chaperone proteins, we may notably mention the human chaperone HSP90.

The products corresponding to general formula (I) as defined above thus display significant inhibitory action on the Hsp90 chaperone.

Tests given in the experimental section below illustrate the inhibitory activity of products of the present invention with respect to said chaperone proteins.

These properties therefore mean that the products of general formula (I) of the present invention can be used as medicinal products for the treatment of malignant tumours.

The products of formula (I) can also be used in the veterinary field.

The invention therefore relates to the application, as medicinal products, of the pharmaceutically acceptable products of general formula (I).

The invention relates in particular to the application, as medicinal products, of the products of formula (I) as defined above having the following names:

[4-(1H-imidazol-2-yl)-9H-fluoren-9(R,S)-yl]-amide of 2-amino-5-chloro-pyrimidine-4-carboxylic acid

[4-(benzofuran-2-yl)-9H-fluoren-9(R,S)-yl)]-amide of 1H-pyrrolo[2,3-b]pyridine-4-carboxylic acid

[4-(quinolin-3-yl)-9H-fluoren-9(R,S)-yl)]-amide of 1H-pyrrolo[2,3-b]pyridine-4-carboxylic acid

[4-(6-fluoro-pyridin-3-yl)-9H-fluoren-9-(R,S)-yl]-amide of 1H-pyrrolo[2,3-b]pyridine-4-carboxylic acid

[4-(1H-indol-2-yl)-9H-fluoren-9-(R,S)-yl]-amide of 1H-pyrrolo[2,3-b]pyridine-4-carboxylic acid

[4-(benzoxazol-2-yl)-9H-fluoren-9-(R,S)-yl]-amide of 1H-pyrrolo[2,3-b]pyridine-4-carboxylic acid

[4-(pyrimidin-5-yl)-9H-fluoren-9-(R,S)yl]-amide of 1H-pyrrolo[2,3-b]pyridine-4-carboxylic acid

[4-(quinolin-2-yl)-9H-fluoren-9-(R,S)-yl]-amide of 1H-pyrrolo[2,3-b]pyridine-4-carboxylic acid (4-[1.2.4]triazolo[1,5-a]pyridin-2-yl-9H-fluoren-9(R,S)-yl)-amide of 1H-pyrrolo[2,3-b]pyridine-4-carboxylic acid

[4-(1,4-benzoxazin-2H-3-yl)-9H-fluoren-9(R,S)-yl]-amide of 1H-pyrrolo[2,3-b]pyridine-4-carboxylic acid

[4-(quinolin-3-yl)-9H-fluoren-9(R,S)-yl]-amide of 7H-pyrrolo[2,3-c]pyrimidine-4-carboxylic acid

[4-(quinoxalin-2-yl)-9H-fluoren-9(R,S)-yl]-amide of 1H-pyrrolo[2,3-b]pyridine-4-carboxylic acid

[4-(quinolin-3-yl)-9H-fluoren-9(R,S)-yl]-amide of 6-bromo-3H-imidazo[4,5-b]pyridine-7-carboxylic acid

[4-(2-morpholino-pyridin-5-yl)-9H-fluoren-9(R,S)-yl]-amide of 1H-pyrrolo[2,3-b]pyridine-4-carboxylic acid

[4-(quinolin-3-yl)-9H-fluoren-9(R,S)-yl]-amide of 2-amino-5-chloro-pyrimidine-4-carboxylic acid

[4-(indazole-1-carbonyl)-9H-fluoren-9(R,S)-yl]-amide of 1H-pyrrolo[2,3-b]pyridine-4-carboxylic acid

[4-(1H-pyrrolo[2,3-b]pyridin-5-yl)-9H-fluoren-9(R,S)-yl]-amide of 1H-pyrrolo[2,3-b]pyridine-4-carboxylic acid 4-(5,6,7,8-tetrahydro-1,8-naphthyridin-3-yl)-9H-fluoren-9(R,S)-yl]-amide of 1H-pyrrolo[2,3-b]pyridine-4-carboxylic acid 4-{imidazo[1,2-a]pyridin-2-yl}-9H-fluoren-9-(R,S)-yl-amide of 1H-pyrrolo[2,3-b]pyridine-4-carboxylic acid dextrorotatory enantiomer of [4-(quinolin-3-yl)-9H-fluoren-9(R,S)-yl]-amide of 6-bromo-3H-imidazo[4,5-b]pyridine-7-carboxylic acid as well as their prodrugs, said products of formula (I) being in all possible isomeric forms: racemates, enantiomers and diastereoisomers, as well as salts of addition of said products of formula (I) with pharmaceutically acceptable inorganic and organic acids or inorganic and organic bases.

The products can be administered by the parenteral, oral, perlingual, rectal or topical route.

The invention also relates to pharmaceutical compositions, characterized in that they contain, as active principle, at least one of the medicinal products of general formula (I).

These compositions can be presented in the form of injectable solutions or suspensions, tablets, coated tablets, capsules, syrups, suppositories, creams, ointments and lotions. These pharmaceutical forms are prepared by the usual methods. The active principle can be incorporated in excipients usually employed in these compositions, such as aqueous or non-aqueous vehicles, talc, gum arabic, lactose, starch, magnesium stearate, cocoa butter, fats of animal or vegetable origin, paraffinic derivatives, glycols, various wetting agents, dispersants or emulsifiers, preservatives.

The usual dose, which varies depending on the subject being treated and the disorder in question, can be for example from 10 mg to 500 mg per day in humans, by the oral route.

The present invention thus relates to the use of products of formula (I) as defined above or of pharmaceutically acceptable salts of said products of formula (I) for the preparation of medicinal products intended to inhibit the activity of chaperone proteins and notably of Hsp90.

The present invention thus relates in particular to the use of products of formula (I) as defined above or of pharmaceutically acceptable salts of said products of formula (I) in which the chaperone protein is HSP90.

The present invention thus relates to the use of products of formula (I) as defined above or of pharmaceutically acceptable salts of said products of formula (I) for the preparation of a medicinal product intended for preventing or treating a disease characterized by disturbance of the activity of a chaperone protein of the Hsp90 type and notably such a disease in a mammal.

The present invention relates to the use of products of formula (I) as defined above or of pharmaceutically acceptable salts of said products of formula (I) for the preparation of a medicinal product intended for preventing or treating a disease belonging to the following group: neurodegenerative diseases such as Huntington's disease, Parkinson's disease, focal cerebral ischaemia, Alzheimer's disease, multiple sclerosis and amyotrophic lateral sclerosis, malaria, brugian and bancroftian filarioses, toxoplasmosis, mycoses resistant to treatments, hepatitis B, hepatitis C, herpes virus, dengue (or breakbone fever), spinal and bulbar muscular atrophy, disorders of proliferation of mesangial cells, thromboses, retinopathies, psoriasis, muscular degeneration, oncologic diseases, cancers.

The present invention thus relates to the use of products of formula (I) as defined above or of pharmaceutically acceptable salts of said products of formula (I) for the preparation of a medicinal product intended for treating oncologic diseases.

The present invention relates in particular to the use of products of formula (I) as defined above or of pharmaceutically acceptable salts of said products of formula (I) for the preparation of a medicinal product intended for treating cancers.

Among these cancers, the present invention relates quite particularly to the treatment of solid tumours and to the treatment of cancers that are resistant to cytotoxic agents.

The present invention thus relates notably to the use of products of formula (I) as defined in any one of the preceding claims or of pharmaceutically acceptable salts of said products of formula (I) for the preparation of a medicinal product intended for treating cancers including lung, breast and ovarian cancers, glioblastomas, chronic myeloid leukaemias, acute lymphoblastic leukaemias, cancers of the prostate, pancreas and colon, metastatic melanomas, tumours of the thyroid and renal carcinomas.

Thus, among the main potential indications of Hsp90 inhibitors, we may mention, non-limitatively:

non-small-cell lung cancers, breast cancers, ovarian cancers and glioblastomas that overexpress EGF-R or HER2;

chronic myeloid leukaemias overexpressing Bcr-Abl;

acute lymphoblastic leukaemias overexpressing Flt-3;

cancers of the breast, prostate, lung, pancreas, colon or ovary overexpressing Akt;

metastatic melanomas and thyroid tumours overexpressing the mutated form of the B-Raf protein;

androgen-dependent and androgen-independent prostate cancers;

oestrogen-dependent and oestrogen-independent breast cancers;

renal carcinomas overexpressing HIF-1a or the mutated c-met protein.

The present invention further relates more particularly to the treatment of breast cancer, colon cancer and lung cancer.

The present invention also relates to the use of products of formula (I) as defined above or of pharmaceutically acceptable salts of said products of formula (I) for the preparation of a medicinal product intended for cancer chemotherapy.

As medicinal products according to the present invention intended for cancer chemotherapy, the products of formula (I) according to the present invention can be used alone or in combination with chemotherapy or radiotherapy or alternatively in combination with other therapeutic agents.

The present invention thus relates notably to the pharmaceutical compositions as defined above containing, in addition, active principles of other medicinal products for chemotherapy against cancer.

Said therapeutic agents can be commonly used antitumour agents.

As examples of known inhibitors of protein kinases, we may mention notably butyrolactone, flavopiridol, 2-(2-hydroxyethylamino)-6-benzylamino-9-methylpurine, olomucin, Glivec and Iressa.

The products of formula (I) according to the present invention can thus also be used advantageously in combination with antiproliferative agents: as examples of said antiproliferative agents though without being limited to this list, we may mention aromatase inhibitors, anti-oestrogens, inhibitors of topoisomerase I, inhibitors of topoisomerase II, agents that act upon microtubules, alkylating agents, histone deacetylase inhibitors, farnesyl transferase inhibitors, COX-2 inhibitors, MMP inhibitors, mTOR inhibitors, antineoplastic antimetabolites, platinum compounds, proteasome inhibitors, such as Bortezomib, inhibitors of Histone Deacetylase (HDACs), such as SAHA, and notably inhibitors of HDAC6, compounds causing a decrease in activity of protein kinases and also anti-angiogenic compounds, gonadorelin agonists, anti-androgens, bengamides, biphosphonates and trastuzumab.

We may thus mention as examples, anti-microtubule agents, such as taxoids, epothilones, Vinca alkaloids, alkylating agents such as cyclophosphamide, DNA-intercalating agents such as cis-platinum and oxaliplatin, agents that interact with topoisomerase such as camptothecin and its derivatives, anthracyclines such as Adriamycin, antimetabolites such as 5-fluorouracil and derivatives and analogues.

The products of formula (I) according to the present invention can be prepared by the application or the adaptation of known methods and notably the methods described in the literature, for example those described by R. C. Larock in: Comprehensive Organic Transformations, VCH Publishers, 1989.

In the reactions described below, it may be necessary to protect reactive functional groups such as for example hydroxy, amino, imino, thio or carboxy groups, when they are desired in the final product but when their participation is undesirable in the reactions of synthesis of the products of formula (I). Conventional protective groups can be used in accordance with the usual standard practices such as those described for example by T. W. Greene and P. G. M. Wuts in "Protective Groups in Organic Chemistry" John Wiley and Sons, 1991.

The experimental section presented below gives non-limiting examples of starting products: other starting products are commercially available or can be prepared by the usual methods known by a person skilled in the art.

EXAMPLES

Examples illustrating the invention: The examples whose preparation is given below illustrate the present invention though without limiting it.

All the examples described were characterized by proton NMR spectroscopy and by mass spectroscopy, and most of these examples were also characterized by infrared spectroscopy.

Example 1

Synthesis of [4-(1H-imidazol-2-yl)-9H-fluoren-9(R,S)-yl]-amide of 2-amino-5-chloro-pyrimidine-4-carboxylic acid Stage 1: In a 250 mL three-necked flask, dissolve 1.5 g of 2-azido-ethylamine, which can be prepared according to Tetrahedron, 47(38), 1991, 8177-8194, and 3.5 g of chloride of fluoren-4-one-9-carboxylic acid in 100 mL of dichloromethane and 4 mL of triethylamine. After stirring for 20 hours at room temperature, pour the reaction mixture into water and extract with dichloromethane. Wash the organic phases with a saturated aqueous solution of sodium bicarbonate and then with water, dry over magnesium sulphate and concentrate at reduced pressure. Make the residue into a paste with diisopropyl oxide, filter and dry in a desiccator at 35° C. We thus obtain 3.65 g of (2-azido-ethyl)-amide of 9-oxo-9H-fluorene-4-carboxylic acid in the form of a yellow powder, to be used as it is in the next stage, and having the following characteristics:

Mass spectrum (E/I): m/z=292 (M+)

Stage 2: In a 250 mL flask under an argon atmosphere, stir, at room temperature overnight, a solution of 3.65 g of (2-azido-ethyl)-amide of 9-oxo-9H-fluorene-4-carboxylic acid, obtained in the preceding stage, 4 g of ditertbutyldicarbonate and 1.5 g of dimethylaminopyridine in 55 mL of tetrahydrofuran. Pour the reaction mixture into water and extract with ethyl acetate. Wash the organic phases with an aqueous solution of sodium dihydrogen phosphate then with a saturated aqueous solution of sodium chloride, dry over magnesium sulphate and concentrate at reduced pressure. We thus obtain 5.25 g of the tert-butyl ester of (2-azido-ethyl)-(9-oxo-9H-fluorene-4-carbonyl)carbamic acid in the form of an orange-coloured oil, to be used as it is in the next stage, and having the following characteristics:

Mass spectrum (LCMS): m/z=392 (M+)

Stage 3: In a 250 mL flask under an argon atmosphere, stir at room temperature for 20 hours, a solution of 4.4 g of the tert-butyl ester of (2-azido-ethyl)-(9-oxo-9H-fluorene-4-carbonyl) carbamic acid, obtained in the preceding stage, and 2.9 g of triphenylphosphine in a mixture of 52 mL of toluene and 13 mL of dichloromethane. Evaporate to dryness at reduced pressure. Purify by flash chromatography on silica gel (40-63 µm), eluting with a mixture of dichloromethane and ethyl acetate (95/5 then 9/1 by volume), obtaining 1.29 g of the tert-butyl ester of (4,5-dihydro-imidazole)-2-(9-oxo-9H-fluoren-4-yl)-1-carboxylic acid, in the form of a yellow powder to be used as it is in the next stage, and having the following characteristics:

$^1$H NMR spectrum (400 MHz, δ in ppm, DMSO-$d_6$): 0.93 (s, 9H); 4.00 (s broad, 4H); 7.36 (d, J=7.5 Hz, 1H); from 7.39 to 7.46 (m, 2H); 7.53 (dd, J=1.5 and 7.5 Hz, 1H); 7.61 (dt, J=1.5 and 7.5 Hz, 1H); from 7.66 to 7.70 (m, 2H).

Stage 4: In a 50 mL flask under an argon atmosphere, cool to 0° C. a solution of 1.29 g of the tert-butyl ester of (4,5-dihydro-imidazole)-2-(9-oxo-9H-fluoren-4-yl)-1-carboxylic acid, obtained in the preceding stage, in 20 mL of dichloromethane and add dropwise 8.5 mL of trifluoroacetic acid. Leave to return to room temperature and stir for 20 hours. Evaporate to dryness at reduced pressure. Add toluene and evaporate to dryness at reduced pressure. Make the residue obtained into a paste in diisopropyl oxide, filter and dry in a desiccator at 35° C. We obtain 1.65 g (100%) of the trifluoroacetate of 4-(4,5-dihydro-1H-imidazol-2-yl)-fluoren-9-one acid, in the form of a yellow powder to be used as it is in the next stage, and having the following characteristics:

Mass spectrum (EI/CI): m/z=362 (M+).

Stage 5: In a 100 mL three-necked flask under an argon atmosphere, cool to −65° C., a solution of 0.65 mL of oxalyl chloride in 5 mL of dichloromethane, then add, dropwise, 0.94 mL of dimethylsulphoxide on 3A molecular sieve. Stir for 10 minutes, then add, dropwise, a solution of 1.65 g of trifluoroacetate of 4-(4,5-dihydro-1H-imidazol-2-yl)-fluoren-9-one acid in 15 mL of dichloromethane then 5 mL of triethylamine. Stir at −65° C. for one hour, then leave to return to room temperature and stir for 2 hours. Pour the reaction mixture into water, and extract with dichloromethane. Wash the organic phases with a saturated aqueous solution of sodium chloride, dry over magnesium sulphate and evaporate to dryness at reduced pressure. After purification by flash chromatography on silica gel (40-63 µm), eluting with a mixture of dichloromethane and methanol (98/2 by volume), we obtain 560 mg of 4-(1H-imidazol-2-yl)-fluoren-9-one in the form of a yellow powder to be used as it is in the next stage, and having the following characteristics:

$^1$H NMR spectrum (400 MHz, δ in ppm, DMSO-$d_6$): From 7.13 to 7.33 (m spread out, 2H); 7.37 (t, J=7.5 Hz, 1H); from 7.45 to 7.53 (m, 2H); 7.64 (d broad, J=7.5 Hz, 1H); 7.69 (d, J=7.5 Hz, 2H); 7.83 (d broad, J=7.5 Hz, 1H); 12.65 (s broad, 1H).

Stage 6: Follow the procedure as in Stage 2 in Example 5, starting from 560 mg of 4-(1H-imidazol-2-yl)-fluoren-9-one, obtained in the preceding stage, 474 mg of hydroxylamine hydrochloride and 933 mg of sodium acetate in 12 mL of ethanol for 20 hours at room temperature. After concentrating the solvent at reduced pressure, take up the residue successively in water, then toluene and finally make into a paste in diisopropyl oxide. We thus obtain 449 mg of 4-(1H-imidazol-2-yl)-fluoren-9-one oxime (Z,E), as a 50-50 mixture of the Z and E isomers, in the form of a pale yellow powder, and having the following characteristics:

Mass spectrum (EI): m/z=261 (M+).

Stage 7: Work in an autoclave as in Stage 3 in Example 5, starting from 449 mg of equimolecular mixture of the Z and E isomers of 4-(1H-imidazol-2-yl)-fluoren-9-one oxime, obtained in the preceding stage, in a mixture of 25 mL of ethanol and 25 mL of tetrahydrofuran, in the presence of Raney nickel, under an initial hydrogen pressure of 1 bar, at 60° C. for 3 hours. After filtration of the catalyst on Celite, concentration of the filtrate at reduced pressure and purification by making into a paste with diisopropyl oxide, we obtain 367 mg of 4-(1H-imidazol-2-yl)-9H-fluorene-9(R,S)-amine, in the form of a white powder, with the following characteristics:

Mass spectrum (EI): m/z=247 (M+).
$^1$H NMR spectrum (400 MHz, δ in ppm, DMSO-$d_6$): 2.29 (m spread out, 2H); 4.76 (s, 1H); 7.14 (s broad, 1H); 7.16 (t partially masked, J=7.5 Hz, 1H); 7.28 (t, J=7.5 Hz, 1H); 7.31 (s broad, 1H); from 7.36 to 7.42 (m, 3H); 7.65 (d, J=7.5 Hz, 1H); 7.74 (m, 1H); 12.4 (s broad, 1H).

Stage 8: Follow the procedure as in Stage 4 in Example 5, starting from 100 mg of 4-(1H-imidazol-2-yl)-9H-fluorene-9(R,S)-amine, obtained in the preceding stage, and 74 mg of 2-amino-5-chloro-pyrimidine-4-carboxylic acid in 2 mL of dimethylformamide, in the presence of 116 mg of hydrochloride of 1-(3-dimethylaminopropyl)-3-ethylcarbodiimide (EDCI) and 82 mg of 1-hydroxybenzotriazole (HOBT), for 20 hours at room temperature. After purification by flash chromatography on silica gel (40-63 μm), eluting with a mixture of dichloromethane and methanol (98/2 then 95/5 by volume), we obtain 52 mg of [4-(1H-imidazol-2-yl)-9H-fluoren-9(R,S)-yl]-amide of 2-amino-5-chloro-pyrimidine-4-carboxylic acid, in the form of an off-white powder with the following characteristics:

Mass spectrum (EI/CI/LCMS): m/z=402 (M+).
$^1$H NMR spectrum (400 MHz, δ in ppm, DMSO-$d_6$): 6.20 (d, J=8.5 Hz, 1H); 7.10 (s broad, 2H); 7.17 (s broad, 1H); 7.27 (t, J=7.5 Hz, 1H); 7.34 (m, 2H); 7.45 (t, J=7.5 Hz, 1H); 7.48 (d, J=7.5 Hz, 1H); 7.54 (d, J=7.5 Hz, 1H); 7.60 (m, 2H); 8.38 (s, 1H); 9.25 (d, J=8.5 Hz, 1H); 12.45 (s broad, 1H).

Example 2

Synthesis of [4-(benzofuran-2-yl)-9H-fluoren-9(R,S)-yl)]-amide of 1H-pyrrolo[2,3-b]pyridine-4-carboxylic acid Stage 1: Introduce successively 5 g of 9-fluorenone-4-carboxylic acid, 22 g of iodobenzene diacetate, 17 g of doubly sublimed iodine and 450 mL of carbon tetrachloride in a photochemical reactor containing a 125 W lamp. After heating for 20 hours at 78° C. under radiation, add 300 mL of a 10% aqueous solution of sodium thiosulphate and stir for 15 minutes. Remove the precipitate (unreacted starting product) and purify the organic phase of the filtrate by flash chromatography on silica gel (20-40 μm), eluting with a mixture of cyclohexane and ethyl acetate (90-10 by volume). We thus obtain 1.59 g of 4-iodo-fluoren-9-one in the form of a yellow solid with the following characteristics:

Mass spectrum (E/I): m/z=306 (M+)
$^1$H NMR spectrum (400 MHz, δ in ppm, DMSO-$d_6$): 7.14 (t, J=8.0 Hz, 1H); 7.48 (d broad, J=7.5 Hz, 1H); 7.66 (dd, J=1.0 and 7.5 Hz, 1H); 7.69 (d broad, J=8.0 Hz, 1H); 7.74 (dt, J=1.0 and 7.5 Hz, 1H); 8.05 (dd, J=1.0 and 7.5 Hz, 1H); 8.59 (d broad, J=8.0 Hz, 1H).

Stage 2: In a microwave tube, dissolve 1.2 g of 4-iodo-fluoren-9-one, obtained in Stage 1, in 30 mL of ethanol, then add successively 0.52 g of bis(triphenylphosphine) palladium (II) chloride, 0.6 g of benzofuran-2-boronic acid and 0.5 mL of triethylamine. After 6 minutes of reaction at 140° C., concentrate to dryness, take up in dichloromethane and in water, extract with 2 times 20 mL of dichloromethane, dry over sodium sulphate, filter and concentrate to dryness. Purify the raw solid obtained by flash chromatography on silica gel (20-40 μm), eluting with a mixture of cyclohexane and ethyl acetate (98-02 by volume). We thus obtain 0.64 g of 4-(benzofuran-2-yl)-fluoren-9-one in the form of a yellow solid, to be used as it is in the next stage and having the following characteristics:

Mass spectrum (E/I): m/z=296 (M+)
$^1$H NMR spectrum (400 MHz, δ in ppm, DMSO-$d_6$): 7.27 (d, J=8.0 Hz, 1H); from 7.34 to 7.46 (m, 4H); from 7.49 to 7.56 (m, 2H); 7.71 (m, 2H); 7.78 (m, 2H); 7.83 (d, J=8.0 Hz, 1H).

Stage 3: In a 100 mL three-necked flask, dissolve 0.64 g of 4-(benzofuran-2-yl)-fluoren-9-one, obtained in Stage 2, in 20 mL of ethanol, then add successively 0.45 g of hydroxylamine hydrochloride and 0.88 g of dry sodium acetate. After stirring overnight at room temperature, concentrate to dryness, and add 20 mL of water. Drain the precipitate that forms, wash with water and dry under a hood. We thus obtain 0.58 g of equimolecular mixture of the Z and E oximes of 4-(benzofuran-2-yl)-fluoren-9-one, in the form of a yellow powder, with the following characteristics:

Melting point (Kofler): 188° C.
Mass spectrum (E/I): m/z=311 (M+)

Stage 4: In a 100 mL autoclave, dissolve 0.58 g of equimolecular mixture of the Z and E isomers of the 4-(benzofuran-2-yl)-fluoren-9-one obtained in Stage 3, in a mixture of 24 mL of ethanol and 24 mL of tetrahydrofuran, add a spatula tip of Raney nickel, then submit to an initial hydrogen pressure of 1 bar and heat the autoclave at 60° C. for 3 hours. After cooling, concentrate the filtrate at reduced pressure. We thus obtain 0.4 g of 4-(benzofuran-2-yl)-9H-fluoren-9(R,S)-yl)-amine, in the form of a semi-solid, to be used as it is in the next stage, having the following characteristics:

Mass spectrum (E/I): m/z=297 (M+)

Stage 5: In a 25 mL three-necked flask, dissolve 400 mg of 4-(benzofuran-2-yl)-9H-fluoren-9(R,S)-yl)-amine, obtained in Stage 4, in 9 mL of dimethylformamide, then add successively 283 mg of hydrochloride of 1-(3-dimethylaminopropyl)-3-ethylcarbodiimide (EDCI), 90 mg of 1-hydroxybenzotriazole (HOBT) and 218 mg of 1H-pyrrolo[2,3-b] pyridine-4-carboxylic acid, then stir for 20 hours at room temperature. Then add 50 mL of water, drain the precipitate that formed and wash it with water and then with a saturated solution of sodium bicarbonate. Purify the raw solid obtained by flash chromatography on silica gel (20-40 μm), eluting with a mixture of dichloromethane and methanol (90-10 by volume). We thus obtain 59 mg of [4-(benzofuran-2-yl)-9H-fluoren-9(R,S)-yl)]-amide of 1H-pyrrolo[2,3-b]pyridine-4-carboxylic acid in the form of a beige solid with the following characteristics:

Melting point (Kofler)>260° C.
Mass spectrum (E/I): m/z=441 (M+)
$^1$H NMR spectrum (400 MHz, δ in ppm, DMSO-$d_6$): 6.41 (d, J=8.5 Hz, 1H); 6.90 (s broad, 1H); 7.19 (d, J=8.0 Hz, 1H); 7.25 (s, 1H); 7.28 (t partially masked, J=8.0 Hz, 1H); from 7.32 to 7.53 (m, 5H); 7.62 (m, 3H); 7.69 (d, J=8.0 Hz, 1H); 7.73 (d, J=8.0 Hz, 1H); 7.79 (d, J=8.0 Hz, 1H); 8.29 (d, J=5.0 Hz, 1H); 9.25 (d, J=8.5 Hz, 1H); 11.85 (m broad, 1H).

Example 3

Synthesis of [4-(quinolin-3-yl)-9H-fluoren-9(R,S)-yl)]-amide of 1H-pyrrolo[2,3-b]pyridine-4-carboxylic acid Stage 1: In a microwave tube, dissolve 1.1 g of 4-iodo-fluoren-9-one, obtained as in Stage 1 in Example 2, in 25 mL of ethanol, then add successively 0.46 g of (triphenylphosphine) palladium (II) chloride, 0.57 g of quinoline-3-boronic acid and 0.9 mL of triethylamine. After reaction at 140° C. for 8 minutes, concentrate to dryness, take up in dichloromethane and in water, extract with 2×20 mL of dichloromethane, dry over magnesium sulphate, filter and concentrate to dryness. Purify the raw solid obtained by flash chromatography on silica gel (20-40 µm), eluting with a mixture of cyclohexane and ethyl acetate (90-10 by volume). We thus obtain 0.53 g of 4-(quinolin-3-yl)-fluoren-9-one in the form of a yellow solid, to be used as it is in the next stage, and having the following characteristics:

Mass spectrum (E/I): m/z=307 (M+)

Stage 2: In a 50 mL three-necked flask, dissolve 0.53 g of 4-(quinolin-3-yl)-fluoren-9-one, obtained in Stage 1, in 15 mL of ethanol, then add successively 0.36 g of hydroxylamine hydrochloride and 0.7 g of dry sodium acetate. After stirring overnight at room temperature, concentrate to dryness, and add 20 mL of water. Drain the precipitate that forms, wash with water and dry under a hood. We thus obtain 0.51 g (92%) of equimolecular mixture of the Z and E oximes of 4-(quinolin-3-yl)-fluoren-9-one, in the form of a yellow powder, to be used as it is in the next stage, and having the following characteristics:

Melting point (Kofler): 204° C.

Mass spectrum (E/I): m/z=322 (M+)

Stage 3: In a 100 mL autoclave, dissolve 0.51 g of equimolecular mixture of the Z and E isomers of 4-(quinolin-3-yl)-fluoren-9-one obtained in Stage 2, in a mixture of 20 mL of ethanol and 20 mL of tetrahydrofuran, add a spatula tip of Raney nickel, then submit to an initial hydrogen pressure of 1 bar and heat the autoclave at 60° C. for 8 hours. After cooling, filter the catalyst on Celite. Concentrate the filtrate at reduced pressure. After purification by flash chromatography on silica gel (20-40 µm), elute with a mixture of dichloromethane and methanol (95-05 by volume). We thus obtain 0.18 g of [4-(quinolin-3-yl)-9H-fluoren-9(R,S)-yl]-amine, in the form of a white meringue, with the following characteristics:

Mass spectrum (E/I): m/z=308 (M+)

Stage 4: In a 25 mL three-necked flask, dissolve 180 mg of [4-(quinolin-3-yl)-9H-fluoren-9(R,S)-yl]-amine, obtained in Stage 3, in 4 mL of dimethylformamide, then add successively 123 mg of hydrochloride of 1-(3-dimethylaminopropyl)-3-ethylcarbodiimide (EDCI), 40 mg of 1-hydroxybenzotriazole (HOBT) and 104 mg of 1H-pyrrolo[2,3-b]pyridine-4-carboxylic acid, then stir for 20 hours at room temperature. Then add 30 mL of water, drain the precipitate that formed and wash it with water and then with a saturated solution of sodium bicarbonate. Purify the raw solid obtained by flash chromatography on silica gel (20-40 µm), eluting with a mixture of dichloromethane and methanol (90-10 by volume). We thus obtain 130 mg of [(4-quinolin-3-yl)-9H-fluoren-9(R,S)-yl]-amide of 1H-pyrrolo[2,3-b]pyridine-4-carboxylic acid in the form of a white solid with the following characteristics:

Melting point (Kofler)>260° C.

Mass spectrum (E/I): m/z=452 (M+)

$^1$H NMR spectrum (400 MHz, δ in ppm, DMSO-$d_6$): 6.43 (d, J=8.5 Hz, 1H); 6.74 (dt, J=8.0 Hz, 1H); 6.92 (dd, J=2.0 and 3.5 Hz, 1H); 7.12 (t, J=7.5 Hz, 1H); 7.29 (t, J=7.5 Hz, 1H); 7.43 (d, J=7.5 Hz, 1H); 7.47 (d, J=5.0 Hz, 1H); 7.49 (t, J=7.5 Hz, 1H); from 7.60 to 7.67 (m, 2H); from 7.70 to 7.75 (m, 2H); 7.88 (t broad, J=7.5 Hz, 1H); 8.12 (d, J=8.5 Hz, 1H); 8.17 (d, J=8.5 Hz, 1H); 8.30 (d, J=5.0 Hz, 1H); 8.53 (m spread out, 1H); 9.01 (m spread out, 1H); 9.26 (d, J=8.5 Hz, 1H); 11.85 (m broad, 1H).

Example 4

Synthesis of [4-(6-fluoro-pyridin-3-yl)-9H-fluoren-9-(R,S)-yl]-amide of 1H-pyrrolo[2,3-b]pyridine-4-carboxylic acid Stage 1: In a microwave tube, dissolve 0.6 g of 4-iodo-fluoren-9-one, obtained as in Stage 1 in Example 2, in 12 mL of ethanol, then add successively 0.28 g of bis(triphenylphosphine) palladium (II) chloride, 0.29 g of 2-fluoropyridine-5-boronic acid and 0.55 mL of triethylamine. After reaction at 140° C. for 6 minutes, concentrate to dryness, take up in dichloromethane and in water, extract with 2 times 20 mL of dichloromethane, dry over magnesium sulphate, filter and concentrate to dryness. Purify the raw solid obtained by flash chromatography on silica gel (20-40 µm), eluting with a mixture of cyclohexane and ethyl acetate (95-05 by volume). We thus obtain 0.28 g of 4-(6-fluoro-pyridin-3-yl)-fluoren-9-one in the form of a yellow solid with the following characteristics:

Melting point (Kofler): 138° C.

Mass spectrum (E/I): m/z=275 (M+)

Stage 2: In a 50 mL three-necked flask, dissolve 0.28 g of 4-(6-fluoro-pyridin-3-yl)-fluoren-9-one obtained in Stage 1, in 10 mL of ethanol, then add successively 0.21 g of hydroxylamine hydrochloride and 0.41 g of dry sodium acetate. After stirring for 4 hours at room temperature, concentrate to dryness, and add 100 mL of water. Drain the precipitate that forms, wash with water and dry under a hood. We thus obtain 0.27 g of equimolecular mixture of the Z and E oximes of 4-(6-fluoro-pyridin-3-yl)-fluoren-9-one, in the form of a pale yellow solid, to be used as it is in the next stage and having the following characteristics:

Mass spectrum (E/I): m/z=290 (M+)

Stage 3: In a 50 mL autoclave, dissolve 0.27 g of equimolecular mixture of the Z and E isomers of 4-(6-fluoro-pyridin-3-yl)-fluoren-9-one, obtained in Stage 2, in a mixture of 10 mL of ethanol and 10 mL of tetrahydrofuran, add a spatula tip of Raney nickel, then submit to an initial hydrogen pressure of 1 bar and heat the autoclave at 60° C. for 3 hours. After cooling, concentrate at reduced pressure. We thus obtain 0.23 g of 4-(6-fluoro-pyridin-3-yl-9H-)-fluoren-9(R,S)-yl]-amine, in the form of a yellow lacquer, to be used as it is and having the following characteristics:

Mass spectrum (E/I): m/z=276 (M+)

Stage 4: In a 25 mL three-necked flask, dissolve 230 mg of 4-(6-fluoro-pyridin-3-yl-9H-)-fluoren-9(R,S)-yl]-amine, obtained in Stage 3, in 7 mL of dimethylformamide, then add successively 175 mg of hydrochloride of 1-(3-dimethylaminopropyl)-3-ethylcarbodiimide (EDCI), 57 mg of 1-hydroxybenzotriazole (HOBT) and 149 mg of 1H-pyrrolo[2,3-b]pyridine-4-carboxylic acid, then stir for 20 hours at room temperature. Then add 30 mL of water, drain the precipitate formed and wash it with water and then with a saturated solution of sodium bicarbonate. Purify the raw solid obtained by flash chromatography on silica gel (20-40 µm), eluting with a mixture of dichloromethane and ethanol (95-05 by volume). We thus obtain 184 mg of [4-(6-fluoro-pyridin-3-yl)-9H-fluoren-9-(R,S)-yl]-amide of 1H-pyrrolo[2,3-b]pyridine-4-carboxylic acid, in the form of a pink solid with the following characteristics:

Melting point (Kofler)>260° C.

Mass spectrum (E/I): m/z=420 (M+)

$^1$H NMR spectrum (400 MHz, δ in ppm, DMSO-$d_6$): 6.40 (d, J=8.5 Hz, 1H); 6.80 (d, J=7.5 Hz, 1H); 6.91 (dd, J=2.0 and 3.5 Hz, 1H); 7.21 (t, J=7.5 Hz, 1H); from 7.29 to 7.34 (m, 2H); 7.41 (dd, J=2.5 and 8.5 Hz, 1H); 7.55 (d, J=5.0 Hz, 1H); 7.56

(t, J=7.5 Hz, 1H); 7.61 (m, 2H); 7.65 (d, J=7.5 Hz, 1H); 8.11 (m spread out, 1H); 8.28 (d, J=5.0 Hz, 1H); 8.35 (m spread out, 1H); 9.23 (d, J=8.5 Hz, 1H); 11.85 (m broad, 1H).

Example 5

[4-(1H-indol-2-yl)-9H-fluoren-9-(R,S)-yl]-amide of 1H-pyrrolo[2,3-b]pyridine-4-carboxylic acid Stage 1: In a 100 mL three-necked flask, under an argon atmosphere, introduce successively 0.59 g of 4-iodo-fluoren-9-one, obtained as in Stage 1 in Example 2, 0.22 g of palladium (0) tetrakis (triphenylphosphine), 0.6 g of sodium carbonate, 0.5 g of 1-(tert-butoxycarbonyl)-indole-2 boronic acid, 2.8 mL of water and 25 mL dioxan. After heating at 100° C. for 1 h 30 min, cool, then add dichloromethane and water, wash with 3×30 mL of water, dry over magnesium sulphate, filter and concentrate to dryness. Purify the raw solid obtained by flash chromatography on silica gel (20-40 µm), eluting with a mixture of cyclohexane and ethyl acetate (98-02 by volume). We thus obtain 0.44 g of tert-butyl ester of 2-(9-oxo-9H-fluoren-4-yl)-indole-1-carboxylic acid in the form of a yellow solid with the following characteristics:
Melting point (Kofler): 170° C.
Mass spectrum (E/I): m/z=395 (M+)

Stage 2: In a 50 mL single-necked flask, dissolve 0.44 g of tert-butyl ester of the 2-(9-oxo-9H-fluoren-4-yl)-indole-1-carboxylic acid obtained in Stage 1, in 10 mL of ethanol, then add successively 0.23 g of hydroxylamine hydrochloride and 0.45 g of dry sodium acetate. After stirring for 20 hours at room temperature, concentrate to dryness, and add 100 mL of water. Drain the precipitate that forms, wash with petroleum ether and dry under a hood. We thus obtain 0.4 g of equimolecular mixture of the Z and E oximes of the tert-butyl ester of 2-(9-oxo-9H-fluoren-4-yl)-indole-1-carboxylic acid in the form of a pale yellow solid, to be used as it is in the next stage, and having the following characteristics:
Melting point (Kofler): 130° C.
Mass spectrum (E/I): m/z=410 (M+)

Stage 3: In a 100 mL autoclave, dissolve 0.4 g of equimolecular mixture of the Z and E isomers of the tert-butyl ester of 2-(9-oxo-9H-fluoren-4-yl)-indole-1-carboxylic acid obtained in Stage 2, in a mixture of 12 mL of ethanol and 12 mL of tetrahydrofuran, add a spatula tip of Raney nickel, then submit to an initial hydrogen pressure of 1 bar and heat the autoclave at 60° C. for 8 hours. After cooling, filter the catalyst on Celite. Concentrate the filtrate at reduced pressure. We thus obtain 0.38 g of tert-butyl ester of 2-[9(R,S)-amino-9H-fluoren-4-yl-]-indole-1-carboxylic acid, in the form of a white lacquer, to be used as it is and having the following characteristics:
Mass spectrum (E/I): m/z=396 (M+)

Stage 4: In a 25 mL three-necked flask, dissolve 375 mg of the tert-butyl ester of 2-[9(R,S)-amino-9H-fluoren-4-yl-]-indole-1-carboxylic acid obtained in Stage 3, in 8 mL of dimethylformamide, then add successively 200 mg of hydrochloride of 1-(3-dimethylaminopropyl)-3-ethylcarbodiimide (EDCI), 65 mg of 1-hydroxybenzotriazole (HOBT) and 169 mg of 1H-pyrrolo[2,3-b]pyridine-4-carboxylic acid, then stir for 20 hours at room temperature. Then add 200 mL of water, drain the precipitate formed and wash it with water, with a saturated solution of sodium bicarbonate and then with petroleum ether. We thus obtain 400 mg of tert-butyl ester of 2-{(R,S)-9-[(1H-pyrrolo[2,3-b]pyridine-4-carbonyl)-amino]-9H-fluoren-4-yl}-indole-1-carboxylic acid in the form of a pale yellow solid, to be used as it is and having the following characteristics:
Mass spectrum (E/I): m/z=540 (M+)

Stage 5: Dissolve 85 mg of tert-butyl ester of 2-{-9-(R,S)-[(1H-pyrrolo[2,3-b]pyridine-4-carbonyl)-amino]-9H-fluoren-4-yl}-indole-1-carboxylic acid, obtained in Stage 4, in 2 mL of dichloromethane and add 0.2 mL of trifluoroacetic acid. After stirring for 20 hours at room temperature, concentrate to dryness, then wash with a solution of sodium bicarbonate, and purify the raw product by flash chromatography on silica gel (20-40 µm), eluting with a mixture of dichloromethane and methanol (95-05 by volume). We thus obtain 35 mg of [4-(1H-indol-2-yl)-9H-fluoren-9(R,S)-yl]-amide of 1H-pyrrolo[2,3-b]pyridine-4-carboxylic acid in the form of a white powder, with the following characteristics:
Mass spectrum (LC/MS): m/z=440 (M+).
$^1$H NMR spectrum (400 MHz, δ in ppm, DMSO-$d_6$): 6.41 (d, J=8.5 Hz, 1H); 6.59 (s broad, 1H); 6.91 (d broad, J=3.5 Hz, 1H); from 7.02 to 7.11 (m, 2H); from 7.13 to 7.22 (m, 2H); 7.31 (t, J=7.5 Hz, 1H); from 7.41 to 7.51 (m, 4H); from 7.57 to 7.69 (m, 4H); 8.29 (d, J=5.0 Hz, 1H); 9.24 (d, J=8.5 Hz, 1H); 11.55 (m broad, 1H); 11.85 (m broad, 1H).

Example 6

[4-(benzoxazol-2-yl)-9H-fluoren-9-(R,S)-yl]-amide of 1H-pyrrolo[2,3-b]pyridine-4-carboxylic acid Stage 1: In a 500 mL three-necked flask, dissolve 2.5 g of 2-amino-phenol in 120 mL of dichloromethane, then add successively at room temperature, 2.8 mL of triethylamine and 2.5 g of chloride of fluoren-4-one-9-carboxylic acid. After stirring for 20 hours at room temperature, pour into 150 mL of water, extract with 20 mL of dichloromethane, wash with a solution of sodium bicarbonate, then with water, and after drying over magnesium sulphate and purifying by flash chromatography on silica gel (40-63 µm), eluting with a mixture of dichloromethane and methanol (98-2 by volume), we obtain 1.8 g of (2-hydroxy-phenyl)-amide of 9-oxo-9H-fluoren-4-carboxylic acid, which is used as it is in the next stage.
Mass spectrum (E/I): m/z=315 (M+).

Stage 2: In a microwave reactor, heat, at 200° C. for 30 minutes, a solution of 1.5 g of (2-hydroxy-phenyl)-amide of 9-oxo-9H-fluoren-4-carboxylic acid obtained in the preceding stage, in 80 mL of acetic acid. After cooling, concentrate in a rotary evaporator and purify the residue by flash chromatography on silica gel (40-63 µm), eluting with dichloromethane. We thus obtain 0.2 g of (4-benzoxazol-2-yl)-9H-fluoren-9-one, in the form of a yellow solid, with the following characteristics:
Mass spectrum (E/I): m/z=297 (M+).

Stage 3: Follow the procedure as in Stage 3 in Example 2, starting from 280 mg of (4-benzoxazol-2-yl)-9H-fluoren-9-one, obtained in the preceding stage, 196 mg of hydroxylamine hydrochloride and 386 mg of sodium acetate, stirring at room temperature for 48 hours in 12 mL of ethanol. After the precipitate that formed has been washed with water and with petroleum ether we obtain, after filtration and drying, 220 mg of (4-benzoxazol-2-yl)-9H-fluoren-9-one oxime, as a 50-50 mixture of the Z and E isomers, in the form of an off-white solid, with the following characteristics:
Melting point (Kofler): 206° C.
Mass spectrum (E/I): m/z=312 (M+).

Stage 4: In a 50 mL autoclave, dissolve 0.22 g of equimolecular mixture of the Z and E isomers of 4-(benzoxazol-2-yl)-fluoren-9-one, obtained in Stage 3, in a mixture of 12 mL of ethanol and 12 mL of tetrahydrofuran, add a spatula tip of Raney nickel, then submit to an initial hydrogen pressure of 1 bar and heat the autoclave at 60° C. for 2 hours. After cooling, filter the catalyst on Celite. Concentrate the filtrate at reduced pressure. We thus obtain 0.21 g of [4-(benzoxazol-2-yl)-9H-fluoren-9-(R,S)-yl]-amine in the form of a brown lacquer, to be used as it is and having the following characteristics:

Mass spectrum (E/I): m/z=298 (M+)

Stage 5: Follow the procedure as in Stage 3 in Example 5 starting from 205 mg of [4-(benzoxazol-2-yl)-9H-fluoren-9-(R,S)-yl]-amine, obtained in Stage 4, and 123 mg of 1H-pyrrolo[2,3-b]pyridine-4-carboxylic acid, in the presence of 145 mg of EDCI and 47 mg of HOBT, in 6 mL of DMF for 6 hours. Pour the reaction mixture into 50 mL of water and drain the precipitate that forms, wash with water, then with a saturated solution of sodium bicarbonate and again with water. Purify the solid obtained by chromatography on silica gel (40-63 µm), eluting with a mixture of dichloromethane and methanol (95/05 by volume). After evaporating to dryness under vacuum, triturate the solid obtained in petroleum ether, filter and dry under vacuum at 40° C. We thus obtain 129 mg of [4-(benzoxazol-2-yl)-9H-fluoren-9-(R,S)-yl]-amide of 1H-pyrrolo[2,3-b]pyridine-4-carboxylic acid, in the form of a beige solid with the following characteristics:

Melting point (Kofler)>260° C.

$^1$H NMR spectrum (400 MHz-DMSO-$d_6$) δ in ppm: 6.42 (d, J=8.5 Hz, 1H); 6.91 (d broad, J=3.5 Hz, 1H); from 7.35 to 7.45 (m, 2H); 7.47 (d, J=5.0 Hz, 1H); from 7.48 to 7.56 (m, 2H); 7.59 (t, J=7.5 Hz, 1H); 7.63 (t, J=3.5 Hz, 1H); 7.66 (d, J=7.5 Hz, 1H); 7.86 (d, J=7.5 Hz, 1H); 7.88 (d, J=7.5 Hz, 1H); 7.97 (d, J=7.5 Hz, 1H); 8.01 (d, J=7.5 Hz, 1H); from 8.25 to 8.35 (m, 2H); 9.29 (d, J=8.5 Hz, 1H); 11.85 (m broad, 1H)

Example 7

[4-(pyrimidin-5-yl)-9H-fluoren-9-(R,S)yl]-amide of 1H-pyrrolo[2,3-b]pyridine-4-carboxylic acid Stage 1: In a microwave tube, dissolve 0.5 g of 4-bromo-fluoren-9-one, which can be obtained according to J. Amer. Chem. Soc, 57, 2443-6, 1935, in 12 mL of ethanol, then add successively 0.27 g of bis(triphenylphosphine) palladium (II) chloride, 0.25 g of pyrimidino-5-boronic acid and 0.54 mL of triethylamine. After reaction at 140° C. for 18 minutes, concentrate to dryness, take up in dichloromethane and in water, dry over magnesium sulphate, filter and concentrate to dryness. Purify the raw solid obtained by flash chromatography on silica gel (20-40 µm), eluting with a mixture of cyclohexane and ethyl acetate (80-20 by volume). We thus obtain 0.3 g of 4-(pyrimidin-5-yl)-fluoren-9-one in the form of a yellow solid, to be used as it is in the next stage and having the following characteristics:

Melting point (Kofler): 188° C.

Stage 2: Follow the procedure as in Stage 2 in Example 5, starting from 300 mg of 4-(pyrimidin-5-yl)-fluoren-9-one, obtained in the preceding stage, 242 mg of hydroxylamine hydrochloride and 477 mg of sodium acetate, stirring at room temperature for 24 hours in 10 mL of ethanol. After concentrating the solvent at reduced pressure, take up the residue in water and drain the precipitate that forms, then rinse with pentane. We thus obtain 310 mg of 4-(pyrimidin-5-yl)-fluoren-9-one oxime, as a 50-50 mixture of the Z and E isomers, in the form of a yellow solid with the following characteristics:

Melting point (Kofler): 222° C.
Mass spectrum (E/I): m/z=273 (M+).

Stage 3: In a 50 mL autoclave, dissolve 0.31 g of equimolecular mixture of the Z and E isomers of 4(-pyrimidin-5-yl)-fluoren-9-one, obtained in Stage 2, in a mixture of 15 mL of ethanol and 15 mL of tetrahydrofuran, add a spatula tip of Raney nickel, then submit to an initial hydrogen pressure of 1 bar and heat the autoclave at 60° C. for 2 hours. After cooling, filter the catalyst on Celite. Concentrate the filtrate at reduced pressure. We thus obtain 0.3 g of 4-(pyrimidin-5-yl)-9H-fluoren-9-(R,S)-yl-amine in the form of a brown lacquer, to be used as it is and having the following characteristics:

Mass spectrum (E/I): m/z=259 (M+)

Stage 4: Follow the procedure as in Stage 4 in Example 5 starting from 290 mg of 4-(pyrimidin-5-yl)-9H-fluoren-9-(R,S)-yl-amine, obtained in Stage 4, and 200 mg of 1H-pyrrolo[2,3-b]pyridine-4-carboxylic acid, in the presence of 236 mg of EDCI and 77 mg of HOBT, in 15 mL of DMF for 48 hours. Pour the reaction mixture into 50 mL of water and drain the precipitate that forms, wash with water, then with a saturated solution of sodium bicarbonate and again with water. Purify the solid obtained by chromatography on silica gel (40-63 µm), eluting with a mixture of dichloromethane and methanol (95/05 by volume). We thus obtain 195 mg of [4-(pyrimidin-5-yl)-9H-fluoren-9-(R,S)-yl]-amide of 1H-pyrrolo[2,3-b]pyridine-4-carboxylic acid, in the form of a white solid with the following characteristics:

Melting point (Kofler)>260° C.
Mass spectrum (E/I): m/z=403 (M+)

$^1$H NMR spectrum (400 MHz-DMSO-$d_6$) δ in ppm: 6.40 (d, J=8.5 Hz, 1H); 6.78 (d, J=7.5 Hz, 1H); 6.91 (d broad, J=3.5 Hz, 1H); 7.21 (t, J=7.5 Hz, 1H); 7.32 (t, J=7.5 Hz, 1H); 7.38 (d, J=7.5 Hz, 1H); 7.47 (d, J=5.0 Hz, 1H); 7.50 (t, J=7.5 Hz, 1H); 7.62 (m, 2H); 7.72 (d, J=7.5 Hz, 1H); 8.29 (d, J=5.0 Hz, 1H); 8.98 (s, 2H); 9.23 (d, J=8.5 Hz, 1H); 9.39 (s, 1H); 11.85 (m broad, 1H).

Example 8

[4-(quinolin-2-yl)-9H-fluoren-9-(R,S)-yl]-amide of 1H-pyrrolo[2,3-b]pyridine-4-carboxylic acid Stage 1: In a 250 mL three-necked flask, introduce successively 2 g of 4-bromo-fluoren-9-one, which can be obtained according to J. Amer. Chem. Soc. 57, 2443-6 (1935), 175 mg of palladium (II) acetate, 3.8 g of potassium acetate, 4.8 g of 4,4,5,5,4',4',5',5'-octamethyl-2,2'-bi[1,3,2-dioxaborolanyl] and 150 mL of dimethylformamide. Pass an argon stream into the solution obtained for 1 hour, then heat at about 70° C. for 1 hour. After cooling, filter the mixture on Celite, add 200 mL of water to the filtrate, extract with 3×50 mL of ethyl acetate, dry over magnesium sulphate and concentrate at reduced pressure. Purify the solid obtained by chromatography on silica gel (40-63 µm), eluting with a mixture of cyclohexane and ethyl acetate (95/05 by volume). We thus obtain 2 g of 4-(4,4,5,5-tetramethyl-1,3,2-dioxaborolan-2-yl)-fluoren-9-one, in the form of a yellow solid, which is used as it is in the next stage, and has the following characteristics:

Mass spectrum (E/I): m/z=306 (M+)

$^1$H spectrum (400 MHz-DMSO-$d_6$) δ in ppm: 1.40 (s, 12H); 7.39 (t broad, J=7.5 Hz, 2H); from 7.59 to 7.66 (m, 2H); 7.71 (d broad, J=7.5 Hz, 1H); 7.87 (dd, J=1.0 and 7.5 Hz, 1H); 8.47 (d broad, J=7.5 Hz, 1H).

Stage 2: In a 250 mL three-necked flask, under an argon atmosphere, introduce successively 2 g of 4-(4,4,5,5-tetramethyl-1,3,2-dioxaborolan-2-yl)-fluoren-9-one, obtained in the preceding stage, 1 g of palladium (0) tetrakis (triphenylphosphine), 2.2 g of caesium carbonate, 0.96 g of 2-bromo-quinoline obtained according to Tetrahedron Letters, 40, (1999), 7477-78, and 60 mL of anhydrous dimethylformamide. After heating at 80° C. for 5 h 30 min, cool, then pour into 200 mL of water, extract with 3×50 mL of ethyl acetate, dry over magnesium sulphate, filter and concentrate at reduced pressure. Purify the raw solid obtained by flash chromatography on silica gel (20-40 µm), eluting with a mixture of cyclohexane and ethyl acetate (90-10 by volume). We thus obtain 0.95 g of 4-(quinolin-2-yl)-fluoren-9-one in the form of a yellow solid with the following characteristics:

Melting point (Kofler): 155° C.

Mass spectrum (E/I): m/z=307 (M+)

Stage 3: Follow the procedure as in Stage 2 in Example 5 starting from 940 mg of 4-quinolin-2-yl-fluoren-9-one, obtained in the preceding stage, 640 mg of hydroxylamine hydrochloride and 1.25 g of sodium acetate, stirring at room temperature for 24 hours in 26 mL of ethanol. After concentrating the solvent at reduced pressure, take up the residue in water and filter the precipitate that formed, then rinse with pentane. We thus obtain 910 mg of 4-(quinolin-2-yl)-fluoren-9-one oxime, as a 50-50 mixture of the Z and E isomers, in the form of a white solid with the following characteristics:

Melting point (Kofler): 260° C.

Mass spectrum (E/I): m/z=322 (M+).

Stage 4: In a 100 mL autoclave, dissolve 0.9 g of equimolecular mixture of the Z and E isomers of 4-(quinolin-2-yl)-fluoren-9-one oxime, obtained in Stage 3, in a mixture of 40 mL of ethanol and 40 mL of tetrahydrofuran, add a spatula tip of Raney nickel, then submit to an initial hydrogen pressure of 1 bar and heat the autoclave at 60° C. for 2 hours. After cooling, filter the catalyst on Celite and concentrate the filtrate at reduced pressure. After purification by flash chromatography on silica gel (20-40 µm), eluting with a mixture of dichloromethane and methanol (95-05 by volume), we obtain 0.72 g of 4-(quinolin-2-yl)-9H-fluoren-9-(R,S)-yl-amine in the form of a white meringue with the following characteristics:

Mass spectrum (E/I): m/z=308 (M+)

Stage 5: Follow the procedure as in Stage 4 in Example 5 starting from 200 mg of 4-(quinolin-2-yl)-9H-fluoren-9-(R,S)-yl-amine, obtained in Stage 4, and 116 mg of 1H-pyrrolo[2,3-b]pyridine-4-carboxylic acid, in the presence of 137 mg of EDCI and 45 mg of HOBT, in 6 mL of DMF for 20 hours. Pour the reaction mixture into 60 mL of water and drain the precipitate that forms, wash with 6×20 mL of water, then with a saturated solution of sodium bicarbonate, again with water and then with isopropyl ether. We thus obtain 185 mg of [4-(quinolin-2-yl)-9H-fluoren-9-(R,S)-yl]-amide of 1H-pyrrolo[2,3-b]pyridine-4-carboxylic acid, in the form of a pinkish-white solid with the following characteristics:

Melting point (Kofler)=260° C.

Mass spectrum (E/I): m/z=452 (M+)

$^1$H NMR spectrum (400 MHz-DMSO-$d_6$) δ in ppm: 6.43 (d, J=8.5 Hz, 1H); 6.82 (d, J=7.5 Hz, 1H); 6.92 (s, 1H); 7.08 (t, J=7.5 Hz, 1H); 7.28 (t, J=7.5 Hz, 1H); from 7.44 to 7.54 (m, 3H); from 7.57 to 7.65 (m, 2H); from 7.62 to 7.75 (m, 2H); 7.78 (t, J=8.0 Hz, 1H); 7.86 (t, J=8.0 Hz, 1H); 8.06 (d, J=8.0 Hz, 1H); 8.13 (d, J=8.0 Hz, 1H); 8.30 (d, J=5.0 Hz, 1H); 8.58 (d, J=8.0 Hz, 1H); 9.26 (d, J=8.5 Hz, 1H); 11.9 (s, 1H).

Example 9

(4-[1.2.4]triazolo[1,5-a]pyridin-2-yl-9H-fluoren-9(R,S)-yl)-amide of 1H-pyrrolo[2,3-b]pyridine-4-carboxylic acid Stage 1: In a microwave reactor, introduce successively 165 mg of 4-(4,4,5,5-tetramethyl-1,3,2-dioxaborolan-2-yl)-fluoren-9-one, obtained in Stage 1 in Example 8, 109 mg of palladium (0) tetrakis (triphenylphosphine), 230 mg of caesium carbonate, 93 mg of 2-bromo-[1.2.4]triazolo[1,5-a]pyridine in 2 mL of anhydrous dimethylformamide. After heating at 140° C. for 18 minutes, pour into 50 mL of water, filter the precipitate that formed and then dissolve it in 20 mL of a mixture of dichloromethane and methanol, dry over magnesium sulphate and concentrate at reduced pressure. Purify the raw solid obtained by flash chromatography on 25 g of silica gel (20-40 µm), eluting with a mixture of cyclohexane and ethyl acetate (70-30 by volume). We thus obtain 70 mg of 4-{[1.2.4]triazolo[1,5-a]pyridin-2-yl}-fluoren-9-one, in the form of a yellow solid with the following characteristics:

Mass spectrum (E/I): m/z=297 (M+)

2-Bromo-[1.2.4]triazolo[1,5-a]pyridine can be obtained by a Sandmeyer-Gattermann diazo-bromination reaction from [1.2.4]triazolo[1,5-a]pyridine-2-amine, prepared in its turn according to Monatsch. Chem. 1983, 114, 789.

Stage 2: Follow the procedure as in Stage 2 in Example 5, starting from 65 mg of 4-{[1.2.4]triazolo[1,5-a]pyridin-2-yl}-fluoren-9-one, obtained in the preceding stage, 45.6 mg of hydroxylamine hydrochloride and 89.7 mg of sodium acetate, stirring at room temperature for 2 hours, then under reflux for 9 hours and 30 minutes in 26 mL of ethanol. After concentrating the solvent at reduced pressure, take up the residue in water and filter the precipitate that formed, then dry under vacuum at 50°. We thus obtain 67 mg of 4-{[1.2.4]triazolo[1,5-a]pyridin-2-yl}-fluoren-9-one oxime, as a 50-50 mixture of the Z and E isomers, in the form of a white powder to be used as it is in the next stage, and having the following characteristics:

Mass spectrum (E/I): m/z=312 (M+).

Stage 3: In a 25 mL three-necked flask, dissolve 67 mg of equimolecular mixture of the Z and E isomers of 4-{[1.2.4]triazolo[1,5-a]pyridin-2-yl}-fluoren-9-one oxime, obtained in Stage 2, in a mixture of 2 mL of ethanol, 1 mL of acetic acid and 1 mL of water, then add 56 mg of zinc and stir at room temperature for 1 hour. After filtering the excess zinc on Celite, rinsing with ethanol and concentrating to dryness at reduced pressure, take up the residue in 50 mL of water. Adjust the pH to 12 by adding 1N aqueous solution of sodium hydroxide and drain the precipitate that forms, then take up in 50 mL of a mixture of dichloromethane and methanol, stir for 15 minutes and finally filter. We thus obtain 54 mg of 4-{[1.2.4]triazolo[1,5-a]pyridin-2-yl}-9H-fluoren-9-(R,S)-yl-amine, in the form of an off-white powder to be used as it is in the next stage, and having the following characteristics:

Mass spectrum (E/I): m/z=298 (M+)

Stage 4: Follow the procedure as in Stage 4 in Example 5 starting from 48 mg of 4-{[1.2.4]triazolo[1,5-a]pyridin-2-yl}-9H-fluoren-9-(R,S)-yl-amine, obtained in Stage 3, and 28.7 mg of 1H-pyrrolo[2,3-b]pyridine-4-carboxylic acid, in the presence of 33.9 mg of EDCI and 12.3 mg of HOBT, in 1 mL of DMF for 2 hours. Pour the reaction mixture into 7 mL of water and drain the precipitate that forms, wash with 10 mL of water, then 3 times with a saturated solution of sodium bicarbonate and then with water. After drying under vacuum at 50°, we obtain 65 mg of 4-{[1.2.4]triazolo[1,5-a]pyridin-2-yl}-9H-fluoren-9-(R,S)-yl-amide of 1H-pyrrolo[2,3-b]pyridine-4-carboxylic acid, in the form of a light beige solid with the following characteristics:

Mass spectrum (E/I): m/z=452 (M+)

Example 10

[4-(1,4-benzoxazin-2H-3-yl)-9H-fluoren-9(R,S)-yl]-amide of 1H-pyrrolo[2,3-b]pyridine-4-carboxylic acid Stage 1: In a microwave reactor, introduce successively 410 mg of 4-(4,4,5,5-tetramethyl-1,3,2-dioxaborolan-2-yl)- fluoren-9-one, obtained in Stage 1 in Example 8, 535 mg of palladium (0) tetrakis (triphenylphosphine), 535 mg of caesium carbonate and 555 mg of N-tert-butyloxycarbonyl-3-iodo-1,4-benzoxazine in 10 mL of anhydrous dimethylformamide. After heating at 140° C. for 12 minutes, pour into 60 mL of water, and extract with 2×30 mL of ethyl acetate. After drying over magnesium sulphate and concentrating at reduced pressure, purify the raw solid obtained by flash chromatography on 25 g of silica gel (40-60 μm), eluting with cyclohexane and then with a mixture of cyclohexane and ethyl acetate (90-10 by volume). We thus obtain 421 mg of 4-(N-tert-butyloxycarbonyl-1,4-benzoxazin-3-yl)-fluoren-9-one, in the form of a beige solid with the following characteristics:

Mass spectrum (E/I): m/z=411 (M+)

N-tert-Butyloxycarbonyl-3-iodo-1,4-benzoxazine can be obtained following the procedure according to Tetrahedron Lett. (1998), 39(32), 5763-4.

Stage 2: Follow the procedure as in Stage 2 in Example 5, starting from 374 mg of 4-(N-tert-butyloxycarbonyl-1,4-benzoxazin-3-yl)-fluoren-9-one, obtained in the preceding stage, 189.5 mg of hydroxylamine hydrochloride and 373 mg of sodium acetate, stirring at room temperature for 3 days in 15 mL of ethanol. After concentrating the solvent at reduced pressure, take up the residue in water; drain the precipitate that forms, wash with petroleum ether, then dry in air. We thus obtain 340 mg of 4-(N-tert-butyloxycarbonyl-1,4-benzoxazin-3-yl)-fluoren-9-one oxime, as a 50-50 mixture of the Z and E isomers, in the form of a yellow powder to be used as it is in the next stage, with the following characteristics:

Mass spectrum (E/I): m/z=323 (M+).

Melting point (Kofler)=223° C.

Stage 3: In a 25 mL three-necked flask, dissolve 190 mg of equimolecular mixture of the Z and E isomers of 4-(N-tert-butyloxycarbonyl-1,4-benzoxazin-3-yl)-fluoren-9-one oxime, obtained in Stage 2, in a mixture of 4 mL of ethanol, 2 mL of acetic acid and 2 mL of water, then add 116.5 mg of zinc and stir at room temperature for 2 hours. After filtration of the excess zinc on Celite, rinse with dichloromethane then with ethanol, and concentrate to dryness at reduced pressure. Purify the raw solid obtained by flash chromatography on 25 g of silica gel (40-60 μm), eluting with dichloromethane then with a mixture of dichloromethane and ammoniacal methanol 0.7N (98-2 by volume). We thus obtain 134 mg of 4-(N-tert-butyloxycarbonyl-1,4-benzoxazin-3-yl)-9H-fluoren-9-(R,S)-yl-amine, in the form of a viscous yellow oil, to be used as it is in the next stage, and having the following characteristics:

Mass spectrum (E/I): m/z=412 (M+)

Stage 4: Follow the procedure as in Stage 4 in Example 5 starting from 210 mg of 4-(N-tert-butyloxycarbonyl-1,4-benzoxazin-3-yl)-9H-fluoren-9-(R,S)-yl-amine, obtained in Stage 3, and 90.89 mg of 1H-pyrrolo[2,3-b]pyridine-4-carboxylic acid, in the presence of 107.34 mg of EDCI and 34.96 mg of HOBT, in 4 mL of DMF for 20 hours. Pour the reaction mixture into 7 mL of water and drain the precipitate that forms, wash with 10 mL of water, then 3 times with a saturated solution of sodium bicarbonate then with water. After purification by flash chromatography on 25 g of silica gel (40-60 μm), eluting with dichloromethane then with a mixture of dichloromethane and methanol (98-2 by volume), we obtain 195 mg of [4-(N-tert-butyloxycarbonyl-1,4-benzoxazin-3-yl)-9H-fluoren-9-(R,S)-yl]-amide of 1H-pyrrolo[2,3-b]pyridine-4-carboxylic acid, in the form of a yellow solid with the following characteristics:

Mass spectrum (E/I): m/z=556 (M+)

Stage 5: In a 25 mL flask, dissolve 180 mg of 4-[(N-tert-butyloxycarbonyl-1,4-benzoxazin-3-yl)-9H-fluoren-9-(R, S)-yl]-amide of 1H-pyrrolo[2,3-b]pyridine-4-carboxylic acid, obtained in the preceding stage, in 10 mL of dichloromethane, then slowly add 1 mL of 4N solution of hydrochloric acid in dioxan and stir overnight at room temperature. After concentrating to dryness, take up the residue in 20 mL of a 7N solution of ammoniacal methanol and concentrate to dryness again. After purification by flash chromatography on 25 g of silica gel (20-40 μm), eluting with dichloromethane then with a mixture of dichloromethane and methanol (98-2 by volume), we obtain 80 mg of [4-(1,4-benzoxazin-2H-3-yl)-9H-fluoren-9-(R,S)-yl]-amide of 1H-pyrrolo[2,3-b]pyridine-4-carboxylic acid, in the form of a yellow solid with the following characteristics:

Mass spectrum (E/I): m/z=456 (M+)

$^1$H NMR spectrum (400 MHz-DMSO-$d_6$) δ in ppm: 5.00 (d, J=16.0 Hz, 1H); 5.14 (d, J=16.0 Hz, 1H); 6.39 (d, J=8.0 Hz, 1H); 6.90 (d, J=3.5 Hz, 1H); 7.05 (d, J=8.0 Hz, 1H); 7.09 (t, J=8.0 Hz, 1H); 7.28 (t, J=8.0 Hz, 1H); from 7.33 to 7.42 (m, 3H); 7.44 (d, J=5.0 Hz, 1H); 7.48 (t, J=8.0 Hz, 1H); 7.54 (d, J=8.0 Hz, 1H); 7.62 (m, 2H); 7.71 (d, J=8.0 Hz, 1H); 7.87 (m, 1H); 8.29 (d, J=5.0 Hz, 1H); 9.21 (d, J=8.0 Hz, 1H); 11.85 (s broad, 1H).

Example 11

[4-(quinolin-2-yl)-9H-fluoren-9(R,S)-yl]-amide of 7H-pyrrolo[2,3-c]pyrimidine-4-carboxylic acid In a 50 mL three-necked flask under an argon atmosphere, stir at room temperature for 10 minutes 308.4 mg of 4-(quinolin-3-yl)-9H-fluoren-9-(R,S)-yl-amine, obtained as in Stage 3 in Example 3, and 239 mg of ethyl ester of 7H-pyrrolo[2,3-c]pyrimidine-4-carboxylic acid in 32 mL of tetrahydrofuran. Add, to the brown suspension thus obtained, 1 mL of a 2M solution of trimethylaluminium in tetrahydrofuran and stir for 1 hour at room temperature. Repeat this operation—addition of 1 mL of a 2M solution of trimethylaluminium in tetrahydrofuran then stirring for 1 hour at room temperature—two more times. Then add 100 mL of a 0.1N aqueous solution of hydrochloric acid and 50 mL of ethyl acetate. Decant the organic phase, then extract the aqueous phase again with 2×50 mL of ethyl acetate. Wash the combined organic phases with a saturated aqueous solution of sodium bicarbonate, dry over magnesium sulphate and concentrate to dryness at reduced pressure. After purification by flash chromatography on 50 g of silica gel (20-40 μm), eluting with a mixture of dichloromethane and methanol (97.5-2.5 by volume), we obtain 90 mg of [4-(quinolin-3-yl)-9H-fluoren-9(R,S)-yl]-amide of 7H-pyrrolo[2,3-c]pyrimidine-4-carboxylic acid, in the form of a light beige solid with the following characteristics:

Mass spectrum (E/I): m/z=453 (M+)

$^1$H NMR spectrum (400 MHz-DMSO-$d_6$) δ in ppm: 6.31 (d, J=8.5 Hz, 1H); 6.73 (d, J=8.0 Hz, 1H); 7.11 (t, J=8.0 Hz, 1H); 7.13 (d, J=3.5 Hz, 1H); 7.26 (t, J=8.0 Hz, 1H); 7.41 (d, J=8.0 Hz, 1H); 7.48 (d, J=8.0 Hz, 1H); 7.57 (d, J=8.0 Hz, 1H); 7.67 (d, J=8.0 Hz, 1H); 7.71 (t, J=8.0 Hz, 1H); 7.79 (d, J=3.5 Hz, 1H); 7.88 (t broad, J=8.0 Hz, 1H); 8.11 (d, J=8.0 Hz, 1H); 8.19 (d, J=8.0 Hz, 1H); 8.53 (s broad, 1H); 8.82 (s, 1H); 9.05 (d, J=2.0 Hz, 1H); 9.41 (d, J=8.5 Hz, 1H); 12.4 (s broad, 1H).

Example 12

[4-(quinoxalin-2-yl)-9H-fluoren-9(R,S)-yl]-amide of 1H-pyrrolo[2,3-b]pyridine-4-carboxylic acid Stage 1: In a microwave reactor, introduce successively 284 mg of 4-(4,4,5,5-tetramethyl-1,3,2-dioxaborolan-2-yl)- fluoren-9-one, obtained in Stage 1 in Example 8, 280 mg of palladium (0) tetrakis (triphenylphosphine), 443.5 mg of caesium carbonate and 150 mg of 2-chloroquinoxaline in 5 mL of anhydrous dimethylformamide. After heating at 140° C. for 30 minutes, pour into 60 mL of water, and extract with 2×30 mL of ethyl acetate. After drying over magnesium sulphate and concentrating at reduced pressure, purify the raw solid obtained by flash chromatography on 25 g of silica gel (40-60 μm), eluting with cyclohexane and then with a mixture of cyclohexane and ethyl acetate (80-20 by volume). We thus obtain 175 mg of 4-(quinoxalin-2-yl)-fluoren-9-one, in the form of a yellow solid with the following characteristics:

Mass spectrum (E/I): m/z=308 (M+)

Stage 2: Follow the procedure as in Stage 3 in Example 2, starting from 170 mg of 4-(quinoxalin-2-yl)-fluoren-9-one, obtained in the preceding stage, 115 mg of hydroxylamine hydrochloride and 226 mg of sodium acetate, stirring at room temperature for 20 hours, then under reflux for 3 hours in 8 mL of ethanol. After concentrating the solvent at reduced pressure, take up the residue in water; filter the precipitate that formed, wash with petroleum ether and then dry in air. We thus obtain 175 mg of 4-(quinoxalin-2-yl)fluoren-9-one oxime, as a 50-50 mixture of the Z and E isomers, in the form of a grey powder, to be used as it is in the next stage, and having the following characteristics:

Mass spectrum (E/I): m/z=323 (M+).

Stage 3: In a 25 mL three-necked flask, dissolve 175 mg of equimolecular mixture of the Z and E isomers of 4-(quinoxalin-2-yl)fluoren-9-one oxime, obtained in Stage 2, in a mixture of 2.5 mL of ethanol, 2.5 mL of acetic acid and 5 mL of water, then add 141.5 mg of zinc and stir at room temperature for 5 hours. After filtering the excess zinc on Celite, and rinsing with ethanol, add 20 mL of a 7N solution of ammonia in methanol and concentrate to dryness at reduced pressure. Purify the raw solid obtained by flash chromatography on 25 g of silica gel (40-60 μm), eluting with dichloromethane and then with a mixture of dichloromethane and methanol (98-2 by volume). We thus obtain 30 mg of 4-(quinoxalin-2-yl)-9H-fluoren-9-(R,S)-yl-amine in the form of a yellow meringue to be used as it is in the next stage, and having the following characteristics:

Mass spectrum (E/I): m/z=309 (M+)

Stage 4: Follow the procedure as in Stage 4 in Example 5 starting from 30 mg of 4-(quinoxalin-2-yl)-9H-fluoren-9-(R,S)-yl-amine, obtained in Stage 3, and 17.3 mg of 1H-pyrrolo[2,3-b]pyridine-4-carboxylic acid, in the presence of 20.4 mg of EDCI and 6.6 mg of HOBT, in 1 mL of DMF for 7 hours. Pour the reaction mixture into 7 mL of water and drain the precipitate that forms, wash with 10 mL of water, then 3 times with a saturated solution of sodium bicarbonate, then with water. After purification by flash chromatography on 25 g of silica gel (40-60 μm), eluting with dichloromethane and then with a mixture of dichloromethane and methanol (98-2 by volume), we obtain 15 mg of [4-(quinoxalin-2-yl)-9H-fluoren-9(R,S)-yl]-amide of 1H-pyrrolo[2,3-b]pyridine-4-carboxylic acid, in the form of a white solid with the following characteristics:

Mass spectrum (E/I): m/z=453 (M+)

$^1$H NMR spectrum (400 MHz-DMSO-$d_6$) δ in ppm: 6.43 (d, J=8.5 Hz, 1H); 6.85 (d, J=7.5 Hz, 1H); 6.92 (dd, J=2.0 and 3.5 Hz, 1H); 7.13 (t, J=7.5 Hz, 1H); 7.31 (t, J=7.5 Hz, 1H); 7.48 (d, J=5.0 Hz, 1H); 7.55 (t, J=7.5 Hz, 1H); from 7.60 to 7.68 (m, 3H); 7.79 (d, J=7.5 Hz, 1H); 7.98 (m, 2H); 8.17 (m, 1H); 8.26 (m, 1H); 8.30 (d, J=5.0 Hz, 1H); 9.22 (s, 1H); 9.28 (d, J=8.5 Hz, 1H); 11.85 (s broad, 1H).

Example 13

[4-(quinolin-3-yl)-9H-fluoren-9(R,S)-yl]-amide of 6-bromo-3H-imidazo[4,5-b]pyridine-7-carboxylic acid Follow the procedure as in Stage 4 in Example 5 starting from 400 mg of 4-(quinolin-3-yl)-9H-fluoren-9(R,S)-yl-amine, obtained as in Stage 4 in Example 8, and 282.4 mg of 6-bromo-3H-imidazo[4,5-b]pyridine-7-carboxylic acid, in the presence of 246 mg of EDCI and 173.5 mg of HOBT, in 12 mL of DMF for 20 hours. Pour the reaction mixture into 60 mL of water and drain the precipitate that forms, wash with 6×20 mL of water, then with a saturated solution of sodium bicarbonate, again with water and then with isopropyl ether. After purification by flash chromatography on 50 g of silica gel (20-40 μm), eluting with a mixture of dichloromethane and methanol (97.5-2.5 by volume), we obtain 245 mg of [4-(quinolin-3-yl)-9H-fluoren-9(R,S)-yl]-amide of 6-bromo-3H-imidazo[4,5-b]pyridine-7-carboxylic acid, in the form of a beige solid with the following characteristics:

Mass spectrum (E/I): m/z=532 (M+)

$^1$H NMR spectrum (500 MHz-DMSO-$d_6$) δ in ppm: 6.43 (d, J=8.5 Hz, 1H); 6.71 (d, J=7.5 Hz, 1H); 7.13 (t, J=7.5 Hz, 1H); 7.33 (t, J=7.5 Hz, 1H); 7.43 (d, J=7.5 Hz, 1H); 7.55 (t, J=7.5 Hz, 1H); 7.71 (t, J=7.5 Hz, 1H); 7.80 (m broad, 1H); 7.88 (t, J=7.5 Hz, 1H); 7.91 (m broad, 1H); 8.10 (d, J=7.5 Hz, 1H); 8.17 (d, J=7.5 Hz, 1H); 8.49 (m broad, 1H); 8.53 (s, 1H); 8.60 (s, 1H); 9.00 (m spread out, 1H); 9.47 (d broad, J=8.5 Hz, 1H); 13.4 (m spread out, 1H).

Example 14

[4-(2-morpholino-pyridin-5-yl)-9H-fluoren-9(R,S)-yl]-amide of 1H-pyrrolo[2,3-b]pyridine-4-carboxylic acid Stage 1: In a 50 mL three-necked flask, introduce successively 864 mg of 4-bromo-fluoren-9-one, which can be obtained according to J. Amer. Chem. Soc. 57, 2443-6 (1935), 1 g of 5-(4,4,5,5-tetramethyl-1,3,2-dioxaborolan-2-yl)-2-morpholino-pyridine, 773 mg of palladium (0) tetrakis (triphenylphosphine) and 1.635 g of caesium carbonate in 21 mL of anhydrous dimethylformamide. After heating for 20 hours at 120° C., pour into 25 mL of water, and extract with 2×30 mL of ethyl acetate. After drying over magnesium sulphate and concentrating at reduced pressure, purify the raw solid obtained by flash chromatography on 100 g of silica gel (40-60 μm), eluting with cyclohexane and then with a mixture of cyclohexane and ethyl acetate (80-20 by volume). We thus obtain 1 g of 4-(2-morpholino-pyridin-5-yl)-fluoren-9-one, in the form of a yellow solid with the following characteristics:

Mass spectrum (E/I): m/z=342 (M+)

Stage 2: Follow the procedure as in Stage 3 in Example 2, starting from 1 g of 4-(2-morpholino-pyridin-5-yl)-fluoren-9-one, obtained in the preceding stage, 609 mg of hydroxylamine hydrochloride and 1.198 g of sodium acetate, stirring at room temperature for 20 hours in 27 mL of ethanol. After concentrating the solvent at reduced pressure, take up the residue in water; filter the precipitate that formed, wash with pentane and then dry in air. We thus obtain 1 g of 4-(2-morpholino-pyridin-5-yl)-fluoren-9-one oxime, as a 50-50 mixture of the Z and E isomers, in the form of a yellow powder, to be used as it is in the next stage, and having the following characteristics:

Mass spectrum (E/I): m/z=357 (M+).

Stage 3: In a 100 mL autoclave, dissolve 1 g of equimolecular mixture of the Z and E isomers of 4-(2-morpholino-pyridin-5-yl)-fluoren-9-one oxime, obtained in Stage 2, in a mixture of 25 mL of ethanol and 25 mL of tetrahydrofuran, then add 175 mg of Raney nickel and stir at a hydrogen pressure of 1 bar for 10 hours at 60° C. After filtering the catalyst and washing it with ethanol, concentrate to dryness at reduced pressure. Purify the raw solid obtained by making a paste in diisopropyl oxide. We thus obtain 960 mg of 4-(2-morpholino-pyridin-5-yl)fluoren-9(R,S)-yl-amine, in the form of a light green solid, to be used as it is in the next stage, and having the following characteristics:

Mass spectrum (E/I): m/z=343 (M+)

Stage 4: Follow the procedure as in Stage 4 in Example 5 starting from 343 mg of 4-(2-morpholino-pyridin-5-yl)fluoren-9(R,S)-yl-amine, obtained in Stage 3, and 162 mg of 1H-pyrrolo[2,3-b]pyridine-4-carboxylic acid, in the presence of 211 mg of EDCI and 148.6 mg of HOBT, in 10 mL of DMF for 20 hours. Pour the reaction mixture into 7 mL of water and drain the precipitate that forms, wash with 10 mL of water, then 3 times with a saturated solution of sodium bicarbonate then with water. After purification by flash chromatography on 50 g of silica gel (40-60 μm), eluting with a mixture of dichloromethane and methanol (97.5-2.5 by volume), we obtain 240 mg of [4-(2-morpholino-pyridin-5-yl)-9H-fluoren-9(R,S)-yl]-amide of 1H-pyrrolo[2,3-b]pyridine-4-carboxylic acid, in the form of a beige solid with the following characteristics:

Mass spectrum (E/I): m/z=487 (M+)

$^1$H NMR spectrum (500 MHz-DMSO-$d_6$) δ in ppm: 3.55 (m, 4H); 3.87 (m, 4H); 6.39 (d, J=8.5 Hz, 1H); 6.90 (dd, J=2.0 and 3.0 Hz, 1H); 7.02 (d, J=7.5 Hz, 1H); 7.08 (d, J=7.5 Hz, 1H); 7.23 (m, 2H); 7.30 (t, J=7.5 Hz, 1H); 7.40 (t, J=7.5 Hz, 1H); 7.46 (d, J=5.0 Hz, 1H); 7.60 (m, 2H); 7.62 (t, J=3.0 Hz, 1H); 7.70 (m spread out, 1H); 8.22 (s broad, 1H); 8.29 (d, J=5.0 Hz, 1H); 9.22 (d, J=8.5 Hz, 1H); 11.9 (s broad, 1H).

Example 15

[4-(quinolin-3-yl)-9H-fluoren-9(R,S)-yl]-amide of 2-amino-5-chloro-pyrimidine-4-carboxylic acid Follow the procedure as in Stage 4 in Example 5 starting from 308 mg of 4-(quinolin-3-yl)-9H-fluoren-9(R,S)-yl-amine, obtained as in Stage 4 in Example 8, and 173.6 mg of 2-amino-5-chloro-pyrimidine-4-carboxylic acid, in the presence of 211 mg of EDCI and 148.6 mg of HOBT, in 10 mL of DMF for 3 days. Pour the reaction mixture into 60 mL of water and drain the precipitate that forms, wash with 6×20 mL of water, then with a saturated solution of sodium bicarbonate, again with water and then with isopropyl ether. Purify the raw product successively by flash chromatography on 25 g of silica gel (20-40 μm), eluting with a mixture of dichloromethane and methanol (97.5-2.5 by volume), then HPLC on a column of Kromasil C18 10 μm (length 35 cm, diameter 8 cm), eluting with a mixture of water containing 0.1% of trifluoroacetic acid and acetonitrile (65/35 by volume). We thus obtain 106 mg of [4-(quinolin-3-yl)-9H-fluoren-9(R,S)-yl]-amide of 2-amino-5-chloro-pyrimidine-4-carboxylic acid, in the form of white crystals with the following characteristics:

Mass spectrum (E/I): m/z=463 (M+)

$^1$H NMR spectrum (400 MHz-DMSO-$d_6$) δ in ppm: 6.28 (d, J=8.5 Hz, 1H); 6.71 (d, J=7.5 Hz, 1H); 7.09 (s, 2H); 7.11 (t, J=7.5 Hz, 1H); 7.30 (t, J=7.5 Hz, 1H); 7.42 (d, J=7.5 Hz, 1H); 7.52 (t, J=7.5 Hz, 1H); 7.58 (d, J=7.5 Hz, 1H); 7.68 (d, J=7.5 Hz, 1H); 7.72 (t, J=7.5 Hz, 1H); 7.88 (t broad, J=7.5 Hz, 1H); 8.10 (d broad, J=7.5 Hz, 1H); 8.17 (d, J=7.5 Hz, 1H); 8.39 (s, 1H); 8.51 (s broad, 1H); 8.99 (s broad, 1H); 9.28 (d, J=8.5 Hz, 1H).

Example 16

[4-(indazole-1-carbonyl)-9H-fluoren-9(R,S)-yl]-amide of 1H-pyrrolo[2,3-b]pyridine-4-carboxylic acid Stage 1: In a 50 mL three-necked flask, under argon, dissolve 243.4 mg of indazole in 10 mL of anhydrous dimethylformamide, then add, a portion at a time, 99 mg of sodium hydride, and stir for 30 minutes, until it dissolves completely. Then add a solution of 500 mg of the chloride of fluoren-9-one-4-carboxylic acid in 7 mL of dimethylformamide. After stirring for 1 h 30 min at room temperature, heat for 1 hour at 70° C., then continue stirring overnight. Pour into 100 mL of water, drain the precipitate that forms and then wash with petroleum ether, and dry in air. We thus obtain 385 mg of 4-(indazole-1-carbonyl)-fluoren-9-one, in the form of a yellow solid with the following characteristics:

Mass spectrum (E/I): m/z=324 (M+)

Stage 2: Follow the procedure as in Stage 3 in Example 2, starting from 385 mg of 4-(indazole-1-carbonyl)-fluoren-9-one, obtained in the preceding stage, 318 mg of hydroxylamine hydrochloride and 318 mg of sodium acetate, stirring at room temperature for 3 hours, then under reflux for 1 hour in 20 mL of ethanol. After concentrating the solvent at reduced pressure, take up the residue in water; filter the precipitate that formed, wash with petroleum ether and then dry in air. We thus obtain 364 mg of 4-(indazole-1-carbonyl)-fluoren-9-one oxime, as a 50-50 mixture of the Z and E isomers, in the form of a yellow powder, to be used as it is in the next stage, and having the following characteristics:

Mass spectrum (E/I): m/z=339 (M+).

Stage 3: In a 25 mL three-necked flask, dissolve 360 mg of equimolecular mixture of the Z and E isomers of 4-(indazole-1-carbonyl)-fluoren-9-one oxime, obtained in Stage 2, in a mixture of 9.5 mL of ethanol, 4.5 mL of acetic acid and 4.5 mL of water, then add 277.5 mg of zinc and stir at room temperature for 1 h 30 min. After filtration of the excess zinc on Celite, rinsing with ethanol, add 20 mL of a 7N solution of ammonia in methanol and concentrate to dryness at reduced pressure. Purify the raw solid obtained by flash chromatography on 25 g of silica gel (15-40 μm), eluting with a mixture of dichloromethane and methanol (95-5 by volume). We thus obtain 239 mg of 4-(indazole-1-carbonyl)-fluoren-9(R,S)-yl-amine, in the form of a white solid used as it is in the next stage, and having the following characteristics:

Mass spectrum (E/I): m/z=325 (M+)

Stage 4: Follow the procedure as in Stage 4 in Example 5 starting from 235 mg of 4-(indazole-1-carbonyl)-fluoren-9(R,S)-yl-amine, obtained in Stage 3, and 128.8 mg of 1H-pyrrolo[2,3-b]pyridine-4-carboxylic acid, in the presence of 152.2 mg of EDCI and 49.8 mg of HOBT, in 5 mL of DMF overnight. Pour the reaction mixture into 7 mL of water and drain the precipitate that forms, wash with 10 mL of water, then 3 times with a saturated solution of sodium bicarbonate and then with water. After purification by flash chromatography on 25 g of silica gel (20-40 μm), eluting with dichloromethane then with mixtures of dichloromethane and methanol (98-2 then 95-5 by volume), we obtain 122 mg of [4-(indazole-1-carbonyl)-9H-fluoren-9(R,S)-yl]-amide of 1H-pyrrolo[2,3-b]pyridine-4-carboxylic acid, in the form of a white solid with the following characteristics:

Melting point (Kofler)=220° C.

Mass spectrum (E/I): m/z=453 (M+)

$^1$H NMR spectrum (400 MHz-DMSO-$d_6$) δ in ppm: 6.41 (d, J=8.5 Hz, 1H); 6.92 (dd, J=2.0 and 3.0 Hz, 1H); 7.09 (d, J=7.5 Hz, 1H); 7.20 (t, J=7.5 Hz, 1H); 7.31 (t, J=7.5 Hz, 1H); 7.48 (d, J=5.0 Hz, 1H); 7.50 (t, J=7.5 Hz, 1H); 7.58 (t, J=7.5 Hz, 1H); from 7.60 to 7.69 (m, 3H); 7.80 (m, 2H); 7.99 (d, J=7.5 Hz, 1H); 8.29 (d, J=5.0 Hz, 1H); 8.43 (s, 1H); 8.60 (d, J=7.5 Hz, 1H); 9.30 (d, J=8.5 Hz, 1H); 11.85 (s broad, 1H).

Example 17

[4-(1H-pyrrolo[2,3-b]pyridin-5-yl)-9H-fluoren-9(R, S)-yl]-amide of 1H-pyrrolo[2,3-b]pyridine-4-carboxylic acid Stage 1: In a 50 mL three-necked flask, introduce successively 1.062 g of 4-bromo-fluoren-9-one, which can be obtained according to J. Amer. Chem. Soc. 57, 2443-6 (1935), 1 g of 5-(4,4,5,5-tetramethyl-1,3,2-dioxaborolan-2-yl)-1H-pyrrolo[2,3-b]pyridine, 947 mg of palladium (0) tetrakis (triphenylphosphine) and 2.003 g of caesium carbonate in 32 mL of anhydrous dimethylformamide. After heating for 20 hours at 120° C., concentrate the dimethylformamide at reduced pressure and then pour it into 25 mL of water, and extract with 2×30 mL of ethyl acetate. After drying over magnesium sulphate and concentrating at reduced pressure, purify the raw solid obtained by flash chromatography on 100 g of silica gel (40-60 µm), eluting with cyclohexane and then with a mixture of cyclohexane and ethyl acetate (70-30 by volume). We thus obtain 455 mg of 4-(1H-pyrrolo[2,3-b]pyridin-5-yl)-fluoren-9-one, in the form of a light brown solid with the following characteristics:

Mass spectrum (E/I): m/z=296 (M+)

Stage 2: Follow the procedure as in Stage 3 in Example 2, starting from 450 g 4-(1H-pyrrolo[2,3-b]pyridin-5-yl)-fluoren-9-one, obtained in the preceding stage, 317 mg of hydroxylamine hydrochloride and 623 mg of sodium acetate, stirring at room temperature for 20 hours in 14 mL of ethanol. After concentrating the solvent at reduced pressure, take up the residue in water; filter the precipitate that formed, wash with a saturated solution of sodium bicarbonate then with pentane and then dry in air. We thus obtain 450 mg of 4-(1H-pyrrolo[2,3-b]pyridin-5-yl)-fluoren-9-one oxime, as a 50-50 mixture of the Z and E isomers, in the form of a yellow powder, to be used as it is in the next stage, and having the following characteristics:

Mass spectrum (E/I): m/z=311 (M+).

Stage 3: In a 100 mL autoclave, dissolve 450 mg of equimolecular mixture of the Z and E isomers of 4-(1H-pyrrolo[2,3-b]pyridin-5-yl)-fluoren-9-one oxime, obtained in Stage 2, in a mixture of 12 mL of ethanol and 12 mL of tetrahydrofuran, then add 90 mg of Raney nickel and stir at a hydrogen pressure of 1 bar for 10 hours at 60° C. After filtering the catalyst and washing it with ethanol, concentrate to dryness at reduced pressure. Purify the raw solid obtained by making a paste in diisopropyl oxide. We thus obtain 400 mg of 4-(1H-pyrrolo[2,3-b]pyridin-5-yl)-fluoren-9(R,S)-yl-amine, in the form of a greenish solid, which is used as it is in the next stage, and has the following characteristics:

Mass spectrum (E/I): m/z=297 (M+)

Stage 4: Follow the procedure as in Stage 4 in Example 5 starting from 400 mg of 4-(1H-pyrrolo[2,3-b]pyridin-5-yl)-fluoren-9(R,S)-yl-amine, obtained in Stage 3, and 218 mg of 1H-pyrrolo[2,3-b]pyridine-4-carboxylic acid, in the presence of 284 mg of EDCI and 200 mg of HOBT, in 13.5 mL of DMF for 20 hours. Pour the reaction mixture into 7 mL of water and drain the precipitate that forms, wash with 10 mL of water, then 3 times with a saturated solution of sodium bicarbonate and then with water. After purification by flash chromatography on 25 g of silica gel (40-60 µm), eluting with a mixture of dichloromethane and methanol (97.5-2.5 by volume), we obtain 175 mg of [4-(1H-pyrrolo[2,3-b]pyridin-5-yl)-9H-fluoren-9(R,S)-yl]-amide of 1H-pyrrolo[2,3-b]pyridine-4-carboxylic acid, in the form of a beige solid with the following characteristics:

Mass spectrum (E/I): m/z=441 (M+):

$^1$H NMR spectrum (400 MHz-DMSO-$d_6$) δ in ppm: 6.41 (d, J=8.5 Hz, 1H); 6.55 (dd, J=2.0 and 3.0 Hz, 1H); 6.73 (d, J=7.5 Hz, 1H); 6.92 (dd, J=2.0 and 3.0 Hz, 1H); 7.10 (t, J=7.5 Hz, 1H); 7.26 (t, J=7.5 Hz, 1H); 7.31 (d, J=7.5 Hz, 1H); 7.44 (t, J=7.5 Hz, 1H); 7.48 (d, J=5.0 Hz, 1H); from 7.55 to 7.68 (m, 4H); 8.02 (m spread out, 1H); 8.27 (m spread out, 1H); 8.29 (d, J=5.0 Hz, 1H); 9.21 (d, J=8.5 Hz, 1H); 11.8 (s broad, 1H); 11.85 (s broad, 1H).

Example 18

[4-(5,6,7,8-tetrahydro-1,8-naphthyridin-3-yl)-9H-fluoren-9(R,S)-yl]-amide of 1H-pyrrolo[2,3-b]pyridine-4-carboxylic acid Stage 1: In a microwave reactor, introduce successively 916 mg of 4-(4,4,5,5-tetramethyl-1,3,2-dioxaborolan-2-yl)-fluoren-9-one, obtained as in Stage 1 in Example 8, 671 mg of palladium (0) tetrakis (triphenylphosphine), 1.42 g of caesium carbonate and 1 g of N8-pivaloyl-3-iodo-5,6,7,8-tetrahydro-1,8-naphthyridine in 20 mL of anhydrous dimethylformamide. After heating for 20 hours at 120° C., pour into 60 mL of water, and extract with 2×30 mL of ethyl acetate. After drying over magnesium sulphate and concentrating at reduced pressure, purify the raw solid obtained by flash chromatography on 100 g of silica gel (40-60 µm), eluting with cyclohexane then with a mixture of cyclohexane and ethyl acetate (70-30 by volume). We thus obtain 1.1 g of 4-(N8-pivaloyl-5,6,7,8-tetrahydro-1,8-naphthyridin-3-yl)-fluoren-9-one, in the form of a yellow meringue with the following characteristics:

Mass spectrum (E/I): m/z=396 (M+)

Stage 2: Follow the procedure as in Stage 3 in Example 2, starting from 950 mg of 4-(N8-pivaloyl-5,6,7,8-tetrahydro-1,8-naphthyridin-3-yl)-fluoren-9-one, obtained in the preceding stage, 500 mg of hydroxylamine hydrochloride and 983 mg of sodium acetate, stirring at room temperature for 20 hours, then under reflux for 3 hours in 22 mL of ethanol. After concentrating the solvent at reduced pressure, take up the residue in water; filter the precipitate that formed, wash with pentane and then dry in air. We thus obtain 750 mg of 4-(5,6,7,8-tetrahydro-1,8-naphthyridin-3-yl)-fluoren-9-one oxime, as a 50-50 mixture of the Z and E isomers, in the form of a grey powder, to be used as it is in the next stage, and having the following characteristics:

Mass spectrum (E/I): m/z=327 (M+).

Stage 3: In a 250 mL autoclave, dissolve 750 mg of equimolecular mixture of the Z and E isomers of 4-(5,6,7,8-tetrahydro-1,8-naphthyridin-3-yl)-fluoren-9-one oxime, obtained in Stage 2, in a mixture of 23 mL of ethanol and 23 mL of tetrahydrofuran, then add 143 mg of Raney nickel and stir at a hydrogen pressure of 1 bar for 8 hours at 60° C. After filtering the catalyst and washing it with ethanol, concentrate to dryness at reduced pressure. Purify the raw solid obtained by making a paste in diisopropyl oxide. We thus obtain 700 mg of 4-(5,6,7,8-tetrahydro-1,8-naphthyridin-3-yl)-fluoren-9(R,S)-yl-amine, in the form of a greenish gum to be used as it is in the next stage, and having the following characteristics:

Mass spectrum (E/I): m/z=313 (M+)

Stage 4: Follow the procedure as in Stage 4 in Example 5 starting from 700 mg of 4-(5,6,7,8-tetrahydro-1,8-naphthyridin-3-yl)-fluoren-9(R,S)-yl-amine, obtained in Stage 3, and 362 mg of 1H-pyrrolo[2,3-b]pyridine-4-carboxylic acid, in the presence of 471 mg of EDCI and 332 mg of HOBT, in 23 mL of DMF for 20 hours. Pour the reaction mixture into 7 mL of water and drain the precipitate that forms, wash with 10 mL of water, then 3 times with a saturated solution of sodium bicarbonate and then with water. After purification by flash chromatography on 100 g of silica gel (40-60 µm), eluting with a mixture of dichloromethane and methanol (97.5-2.5 by volume), we obtain 510 mg of [4-(5,6,7,8-tetrahydro-1,8-naphthyridin-3-yl)-9H-fluoren-9(R,S)-yl]-amide of 1H-pyrrolo[2,3-b]pyridine-4-carboxylic acid, in the form of a white solid with the following characteristics:

Mass spectrum (E/I): m/z=457 (M+)

$^1$H NMR spectrum (400 MHz-DMSO-$d_6$) δ in ppm: 1.85 (m, 2H); 2.77 (m, 2H); 3.48 (m, 2H); 6.37 (d, J=8.5 Hz, 1H); 6.61 (s broad, 1H); 6.91 (dd, J=2.0 and 3.0 Hz, 1H); from 7.15 to 7.33 (m, 5H); 7.38 (t, J=7.5 Hz, 1H); 7.47 (d, J=5.0 Hz, 1H); from 7.51 to 7.67 (m, 3H); 7.84 (s broad, 1H); 8.29 (d, J=5.0 Hz, 1H); 9.19 (d, J=8.5 Hz, 1H); 11.85 (s broad, 1H).

Example 19

4-{imidazo[1,2-a]pyridin-2-yl}-9H-fluoren-9-(R,S)-yl-amide of 1H-pyrrolo[2,3-b]pyridine-4-carboxylic acid Stage 1: In a 1 L flask containing 30 g of monochloroacetic acid dissolved in 150 mL of distilled water, add, in small portions, 24.1 g of potassium carbonate. After stirring for 15 minutes after the end of this addition (end of effervescence), add 30 g of 2-aminopyridine and reflux the reaction mixture for 6 hours. Leave to return to room temperature overnight. Filter the pinkish suspension, wash the solid with distilled water, then dry under vacuum at 40° C. We obtain 15 g of a beige solid of 2-hydroxy-imidazo[1,2-a]pyridine.

Stage 2: In a 500 mL flask containing 1 g of 2-hydroxy-imidazo[1,2-a]pyridine obtained in the preceding stage and 60 mL of toluene, add 2.6 g of N-phenyl-bis(trifluoromethanesulphonimide) and 1 mL of triethylamine and then heat under reflux. After reflux for 2 hours and 4 hours, add respectively 2.5 mL and 5 mL of triethylamine, then continue with reflux for 8 hours. After cooling add 50 mL of distilled water, decant and re-extract the aqueous phase with 3×50 mL of ethyl acetate. Wash the combined organic phases with 3×50 mL of distilled water, 1×50 mL of saturated sodium chloride solution and then dry over magnesium sulphate. After evaporating to dryness under vacuum, chromatograph the oily residue on silica gel (40-63 µm), eluting with dichloromethane. We obtain 0.3 g of 2-trifluoromethanesulphonyloxy-imidazo[1,2-a]pyridine in the form of white crystals with the following characteristics:

Mass spectrum (LC/MS): m/z=266 (M+).

Stage 3: In a 100 mL flask, heat under argon at 120° C. a mixture of 178 mg of 4-(4,4,5,5-tetramethyl-1,3,2-dioxaborolan-2-yl)-fluoren-9-one, obtained in Stage 1 in Example 8, 150 mg of 2-trifluoromethanesulphonyloxy-imidazo[1,2-a]pyridine obtained in the preceding stage, 130 mg of palladium (0) tetrakis (triphenylphosphine), 276 mg of caesium carbonate in 20 mL of anhydrous dimethylformamide for 3 hours. After evaporating the reaction mixture to dryness under vacuum, take up the residue in 20 mL of distilled water and extract with 8×15 mL of ethyl acetate. Wash the combined organic phases with 2×15 mL of distilled water, 15 mL of saturated sodium chloride solution, and then dry over sodium sulphate. After evaporating to dryness under vacuum, chromatograph the oily residue on silica gel (40-63 µm), eluting with a mixture of ethyl acetate and cyclohexane (4:6). We obtain 120 mg of 4-{imidazo[1,2-a]pyridin-2-yl}-fluoren-9-one in the form of yellow crystals with the following characteristics:

Mass spectrum (LC/MS): m/z=296 (M+).

Stage 4: In a 100 mL flask, stir under argon at room temperature 120 mg of 4-{imidazo[1,2-a]pyridin-2-yl}-fluoren-9-one obtained in the preceding stage, 84 mg of hydroxylamine hydrochloride and 160 mg of sodium acetate in 5 mL of ethanol. Evaporate the reaction mixture to dryness under vacuum. Take up the residue in 10 mL of distilled water and filter the precipitate, wash with 3×1.5 ml of distilled water, 2×1.5 mL of a saturated solution of sodium bicarbonate, 3×1.5 mL of distilled water, and then dry under vacuum. We obtain 48 mg of 4-{imidazo[1,2-a]pyridin-2-yl}-fluoren-9-one oxime, as equimolecular mixture of the Z and E isomers, in the form of a beige solid with the following characteristics:

Mass spectrum (LC/MS): m/z=311 (M+).

Stage 5: In a 25 mL flask, stir at room temperature overnight 102 mg of 4-{imidazo[1,2-a]pyridin-2-yl}-fluoren-9-one oxime obtained in the preceding stage and 86 mg of zinc powder in a mixture of 0.6 mL of acetic acid, 0.6 mL of distilled water and 0.6 mL of ethanol. After adding Celite, filter the reaction mixture and wash the precipitate with 3×1.5 mL of ethanol. Evaporate the filtrate to dryness under vacuum and chromatograph the residue on silica gel (40-63 µm), eluting with a mixture of dichloromethane-ethanol-ammonia 7N in methanol (90/10/0.5 by volume). We obtain 95 mg of 4-{imidazo[1,2-a]pyridin-2-yl}-9H-fluoren-9(R,S)-yl-amine in the form of a beige meringue with the following characteristics:

Mass spectrum (LC/MS): m/z=297 (M+).

Stage 6: In a 50 mL flask, stir under argon overnight at room temperature, 94 mg of 4-{imidazo[1,2-a]pyridin-2-yl}-9H-fluoren-9(R,S)-yl-amine obtained in the preceding stage, 51 mg of 1H-pyrrolo[2,3-b]pyridine-4-carboxylic acid, 61 mg of EDCI and 21 mg of HOBt in 10 mL of DMF. After evaporating the reaction mixture to dryness under vacuum, take up the residue in 15 mL of distilled water and extract with 3×15 mL of ethyl acetate. Wash the combined organic phases with 10 mL of a saturated solution of sodium bicarbonate, 2×10 mL of distilled water, 10 mL of saturated solution of sodium chloride, and dry over magnesium sulphate. After evaporating to dryness under vacuum, chromatograph the residue on silica gel (40-63 µm), eluting with a mixture of dichloromethane-ethanol (92.5:7.5). We thus obtain 38 mg of 4-{imidazo[1,2-a]pyridin-2-yl}-9H-fluoren-9(R,S)-yl-amide of 1H-pyrrolo[2,3-b]pyridine-4-carboxylic acid in the form of white crystals with the following characteristics:

Melting point (Kofler): 270° C.

Mass spectrum (LC/SM): m/z 441 (M+)

$^1$H NMR spectrum (400 MHz-DMSO-$d_6$) δ in ppm: 6.39 (d, J=8.5 Hz, 1H); 6.91 (dd, J=2.0 and 3.5 Hz, 1H); 7.00 (dt, J=1.5 and 7.5 Hz, 1H); 7.21 (dt, J=1.5 and 7.5 Hz, 1H); from 7.28 to 7.39 (m, 2H); 7.42 (t, J=7.5 Hz, 1H); 7.47 (d, J=5.5 Hz, 1H); 7.50 (d, J=7.5 Hz, 1H); 7.59 (d, J=7.5 Hz, 1H); 7.62 (m, 3H); 7.69 (d, J=7.5 Hz, 1H); 8.20 (s, 1H); 8.29 (d, J=5.5 Hz, 1H); 8.63 (d, J=7.5 Hz, 1H); 9.26 (d, J=8.5 Hz, 1H); 11.9 (s broad, 1H).

Examples 20 and 21

Levorotatory Enantiomer and Dextrorotatory Enantiomer of [4-(quinolin-3-yl)-9H-fluoren-9(R,S)-yl]-amide of 6-bromo-3H-imidazo[4,5-b]pyridine-7-carboxylic acid Resolve 95 mg of [4-(quinolin-3-yl)-9H-fluoren-9(R,S)-yl]-amide of 6-bromo-3H-imidazo[4,5-b]pyridine-7-carboxylic acid, obtained as in Example 13, by high-performance liquid chromatography on a column with length of 350 mm and diameter of 50 mm filled with silica Chiralpak 50801 20 μm, eluting with a mixture of acetonitrile and methanol (90/10 by volume) at a flow rate of 50 mL/min, monitoring the separation by UV detection at 254 nm.

Recovering the second fraction eluted (retention time 9.86 minutes) and concentrating at reduced pressure, we obtain 38.9 mg of the levorotatory enantiomer of [4-(quinolin-3-yl)-9H-fluoren-9(R,S)-yl]-amide of 6-bromo-3H-imidazo[4,5-b]pyridine-7-carboxylic acid, in the form of a white meringue with the following characteristics:

$\alpha^D_{20}$+−109.4±1.6°(c=0.47; DMSO)

Recovering the second fraction eluted (retention time 16.91 minutes) and concentrating at reduced pressure, we obtain 31.1 mg of the dextrorotatory enantiomer of [4-(quinolin-3-yl)-9H-fluoren-9(R,S)-yl]-amide of 6-bromo-3H-imidazo[4,5-b]pyridine-7-carboxylic acid, in the form of a white meringue with the following characteristics:

$\alpha^D_{20}$=+87.5±1.5°(c=0.41; DMSO)

Example 22

Pharmaceutical Composition

Tablets were prepared with the following formula:

| | |
|---|---|
| Product from Example 1 | 0.2 g |
| Excipient for one tablet to give | 1 g |

(details of excipient: lactose, talc, starch, magnesium stearate).

Example 23

Pharmaceutical Composition

Tablets were prepared with the following formula:

| | |
|---|---|
| Product from Example 16 | 0.2 g |
| Excipient for one tablet to give | 1 g |

(details of excipient: lactose, talc, starch, magnesium stearate).

The present invention also comprises all pharmaceutical compositions prepared with any product of formula (I) according to the present invention.

Examples 24-01 to 24-106

By proceeding according to the general methods described previously, and more specifically according to one of the two schemes below,

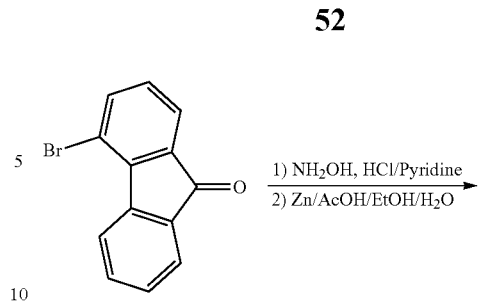

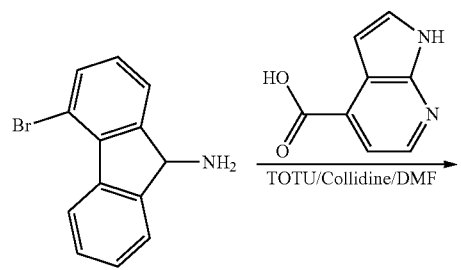

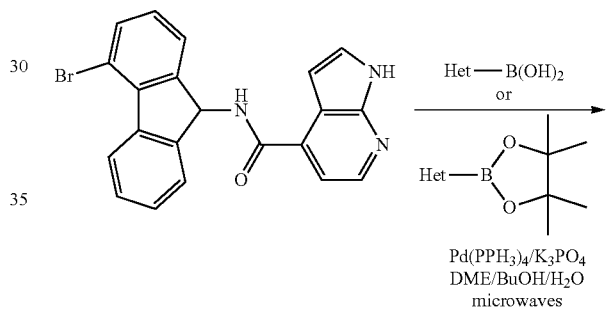

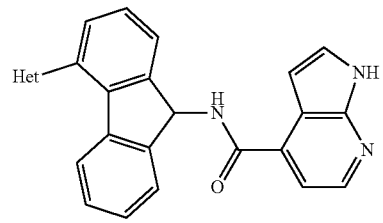

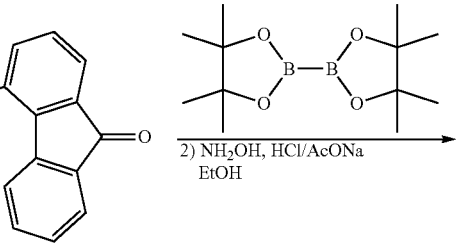

53
-continued
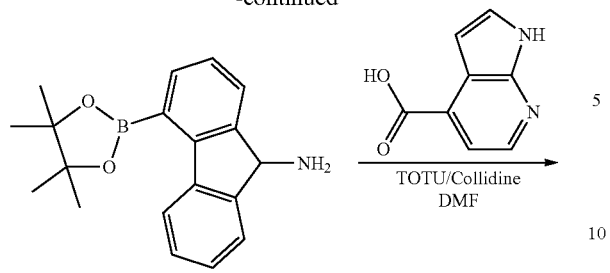
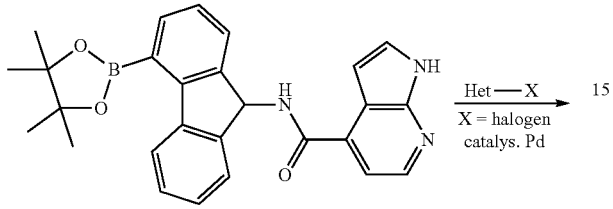
54
-continued
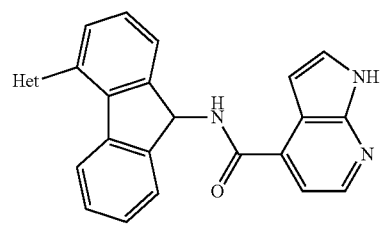
the compounds from Table 1 below are obtained (after deprotection of the protecting groups present, where appropriate), which compounds also constitute exemplary embodiments of the present invention.
TABLE 1
Examples 24-01 to 24-106
| Example | Structure |
| --- | --- |
| 24-01 | 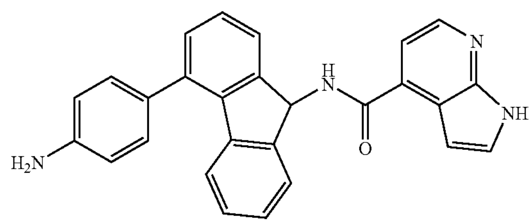 |
| 24-02 | 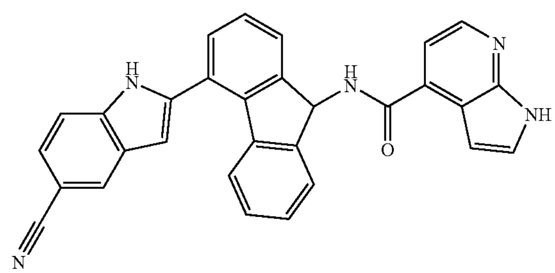 |
| 24-03 | 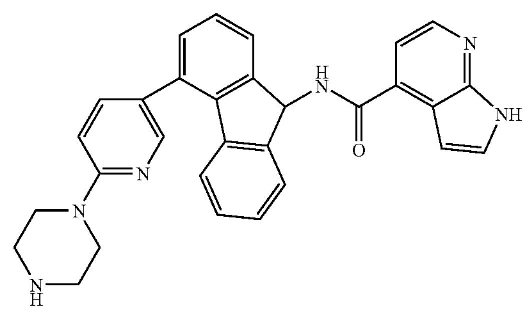 |
| 24-04 | 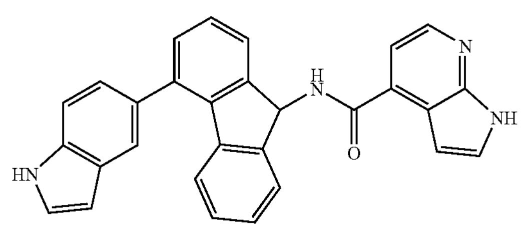 |

TABLE 1-continued

Examples 24-01 to 24-106

| Example | Structure |
|---------|-----------|
| 24-05 | 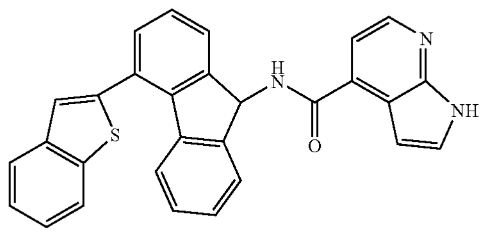 |
| 24-06 | 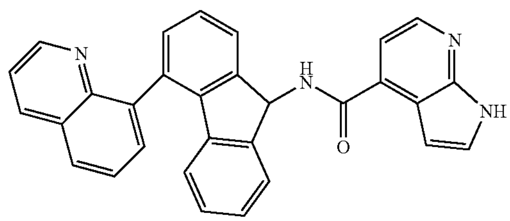 |
| 24-07 | 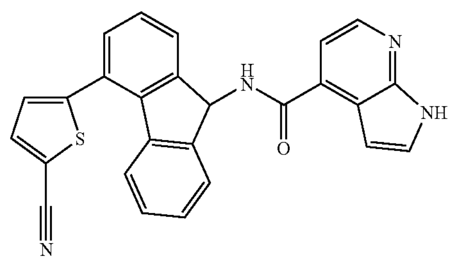 |
| 24-08 | 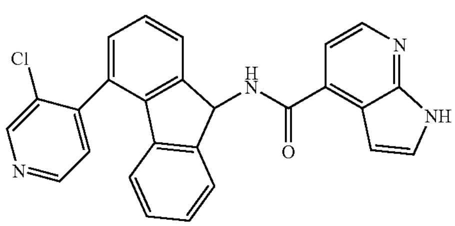 |
| 24-09 | 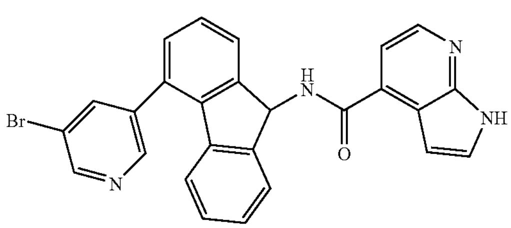 |
| 24-10 | 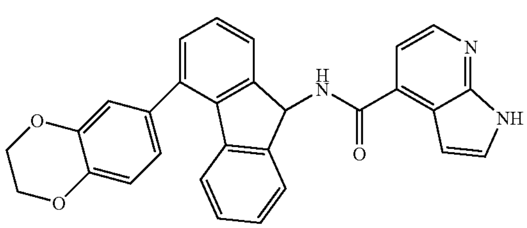 |

TABLE 1-continued

Examples 24-01 to 24-106

| Example | Structure |
|---|---|
| 24-11 | 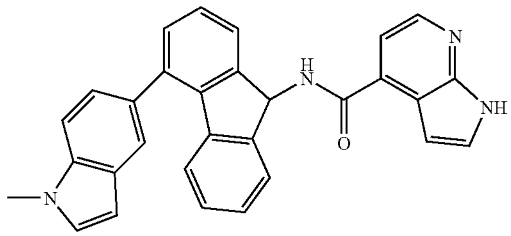 |
| 24-12 | 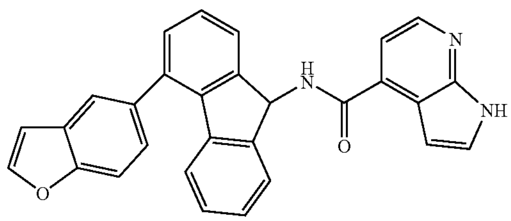 |
| 24-13 | 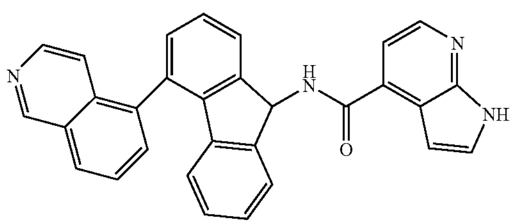 |
| 24-14 | 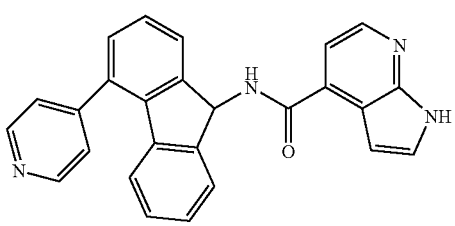 |
| 24-15 | 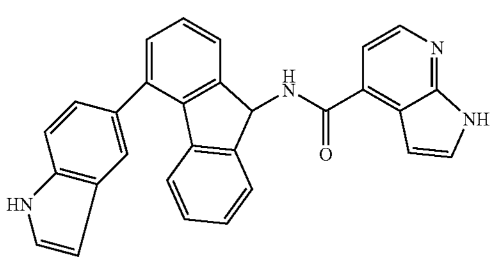 |
| 24-16 | 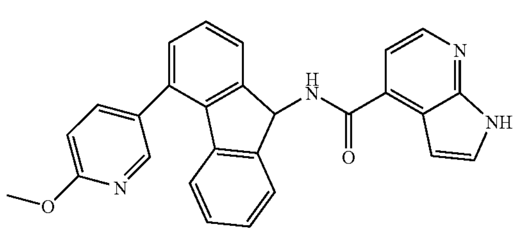 |

TABLE 1-continued

Examples 24-01 to 24-106

| Example | Structure |
|---------|-----------|
| 24-17 | 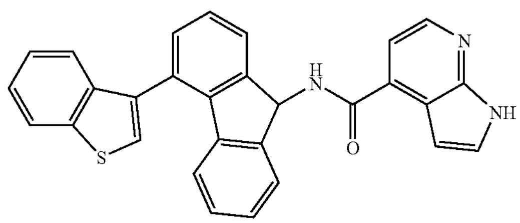 |
| 24-18 | 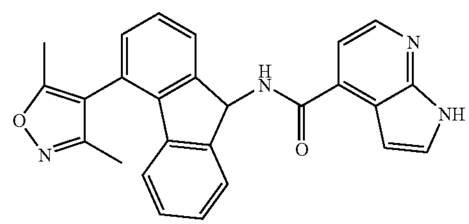 |
| 24-19 | 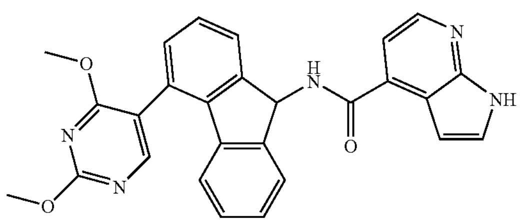 |
| 24-20 | 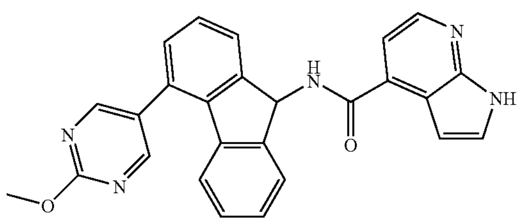 |
| 24-21 | 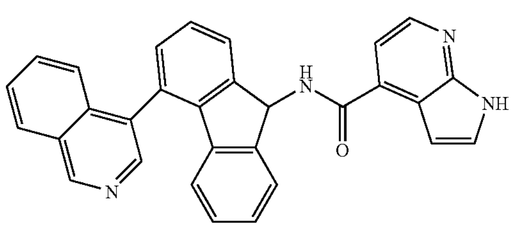 |
| 24-22 | 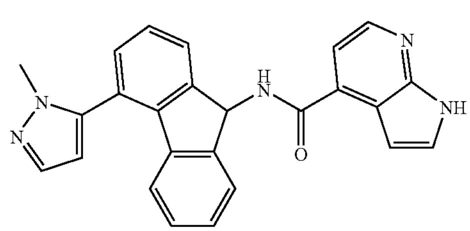 |

TABLE 1-continued

Examples 24-01 to 24-106

| Example | Structure |
|---|---|
| 24-23 | 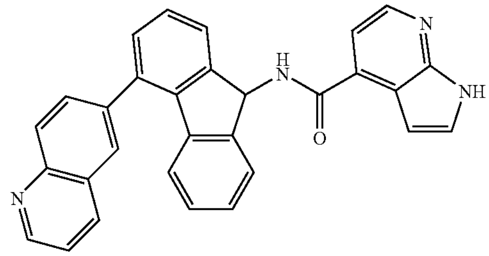 |
| 24-24 | 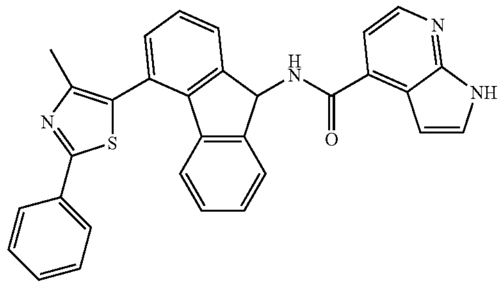 |
| 24-25 | 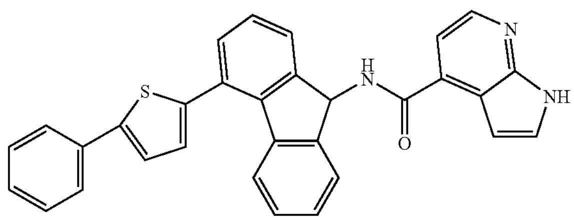 |
| 24-26 | 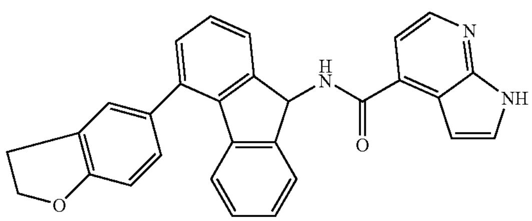 |
| 24-27 | 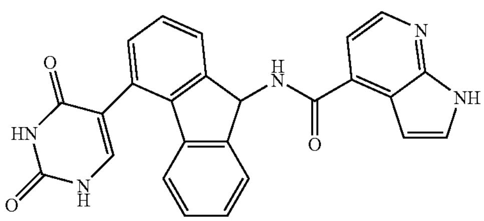 |
| 24-28 | 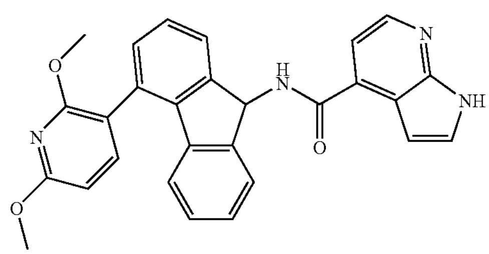 |

TABLE 1-continued
Examples 24-01 to 24-106
| Example | Structure |
|---|---|
| 24-29 | 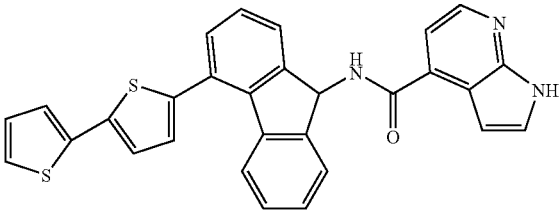 |
| 24-30 | 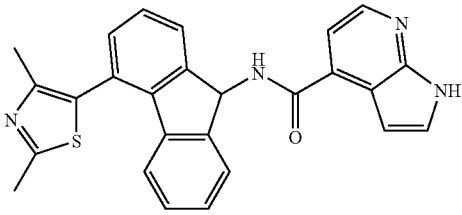 |
| 24-31 | 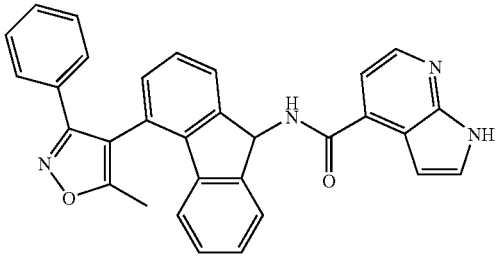 |
| 24-32 | 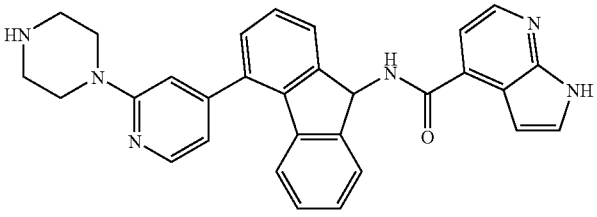 |
| 24-33 | 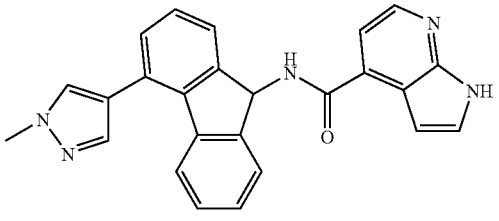 |
| 24-34 | 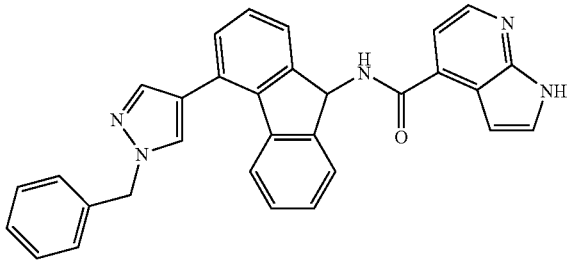 |

TABLE 1-continued
Examples 24-01 to 24-106
| Example | Structure |
|---|---|
| 24-35 | 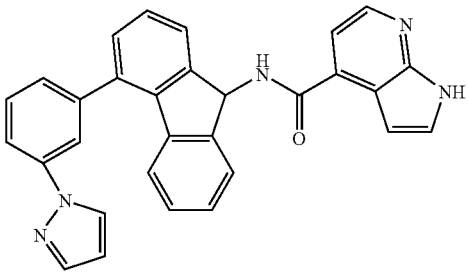 |
| 24-36 | 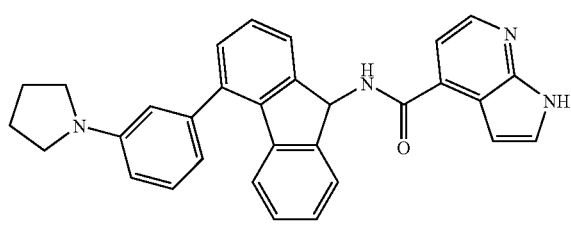 |
| 24-37 | 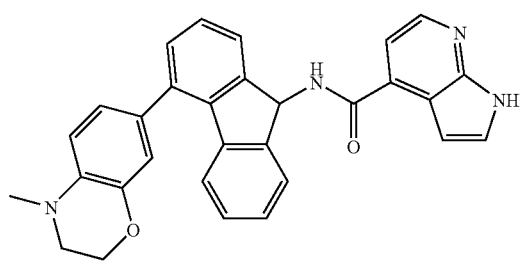 |
| 24-38 | 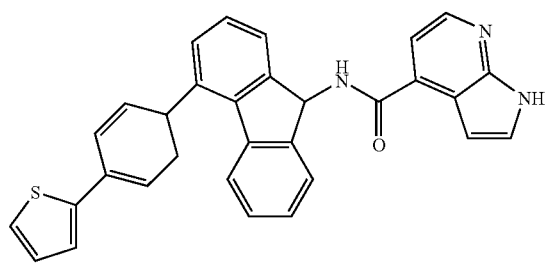 |
| 24-39 | 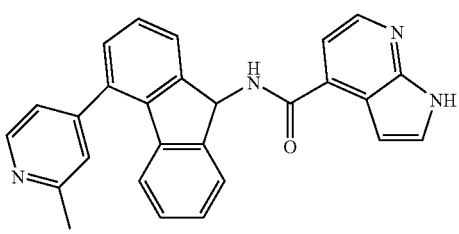 |
| 24-40 | 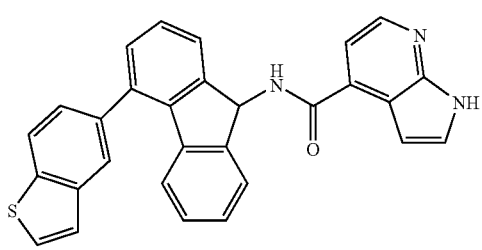 |

US 8,163,750 B2
TABLE 1-continued
Examples 24-01 to 24-106
| Example | Structure |
|---|---|
| 24-41 | 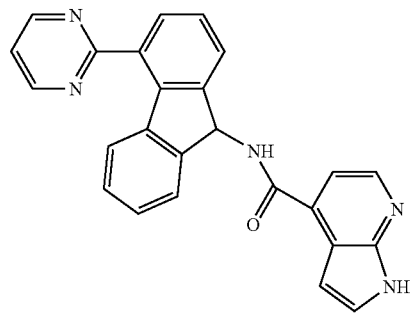 |
| 24-42 | 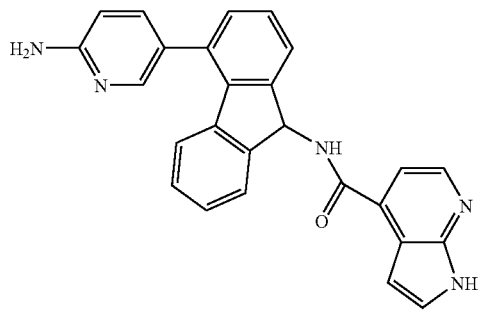 |
| 24-43 | 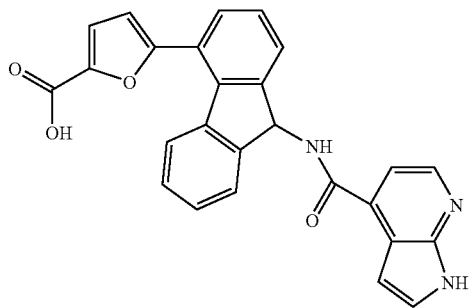 |
| 24-44 | 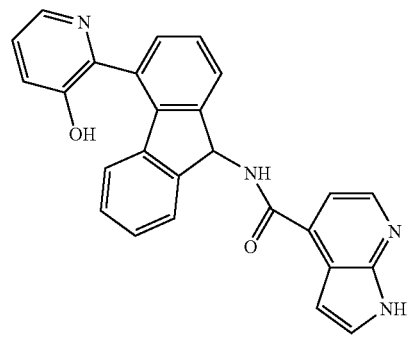 |

TABLE 1-continued

Examples 24-01 to 24-106

| Example | Structure |
|---------|-----------|
| 24-45 | 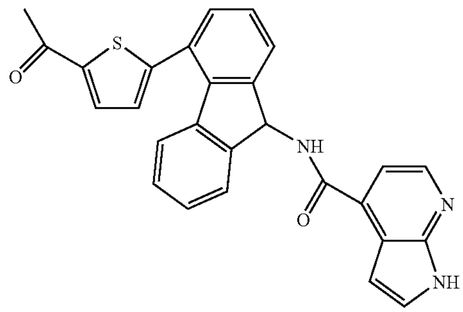 |
| 24-46 | 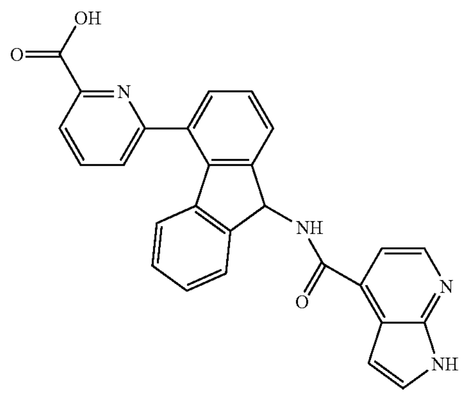 |
| 24-47 | 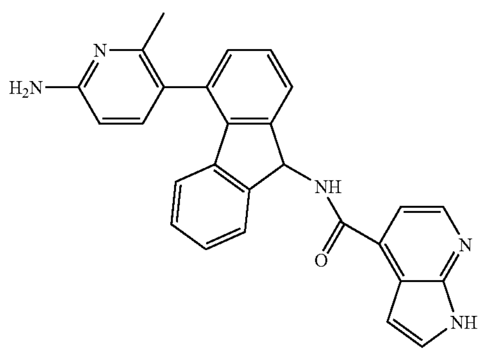 |
| 24-48 | 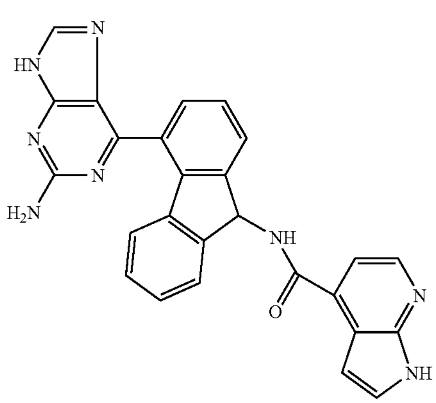 |

TABLE 1-continued
Examples 24-01 to 24-106
| Example | Structure |
|---|---|
| 24-49 | 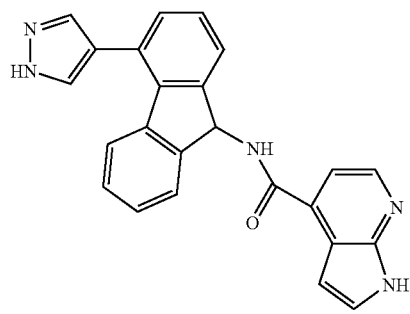 |
| 24-50 | 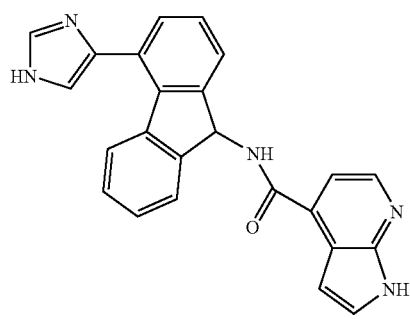 |
| 24-51 | 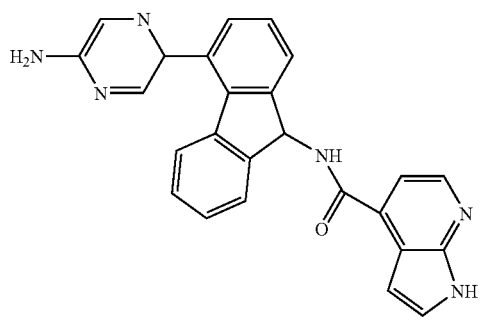 |
| 24-52 | 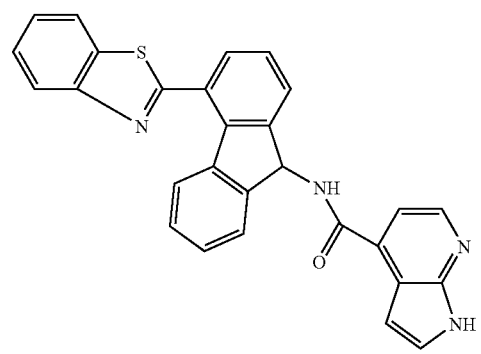 |

TABLE 1-continued

Examples 24-01 to 24-106

| Example | Structure |
|---|---|
| 24-53 | (structure) |
| 24-54 | (structure) |
| 24-55 | (structure) |
| 24-56 | (structure) |

TABLE 1-continued
Examples 24-01 to 24-106
| Example | Structure |
|---|---|
| 24-57 | 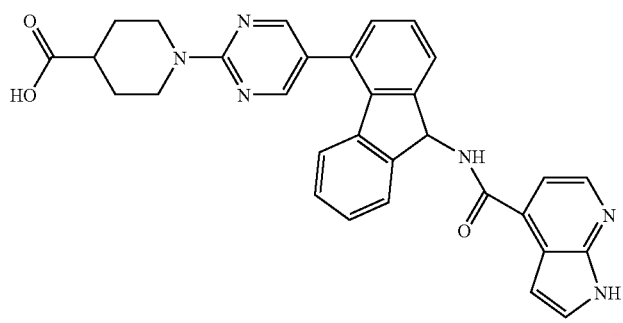 |
| 24-58 | 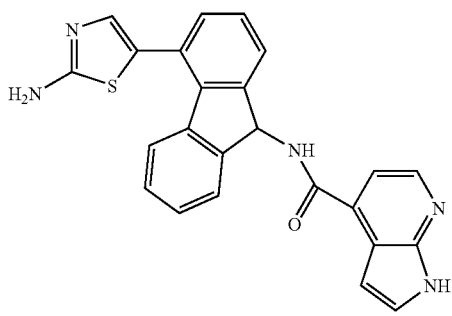 |
| 24-59 | 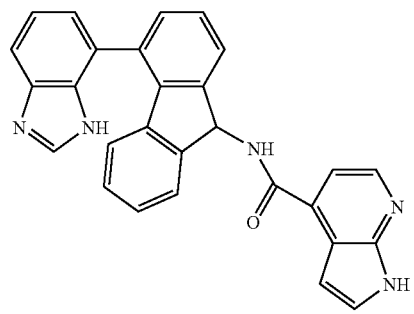 |
| 24-60 | 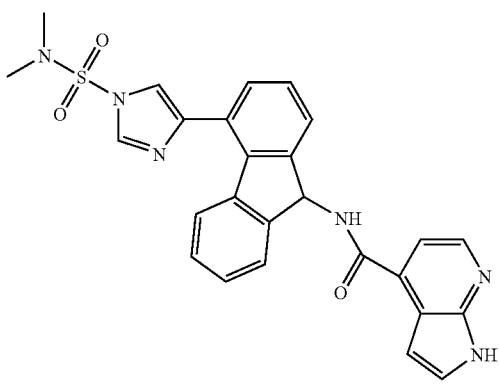 |

TABLE 1-continued
Examples 24-01 to 24-106
| Example | Structure |
|---|---|
| 24-61 | 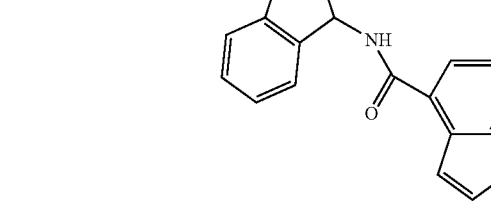 |
| 24-62 | 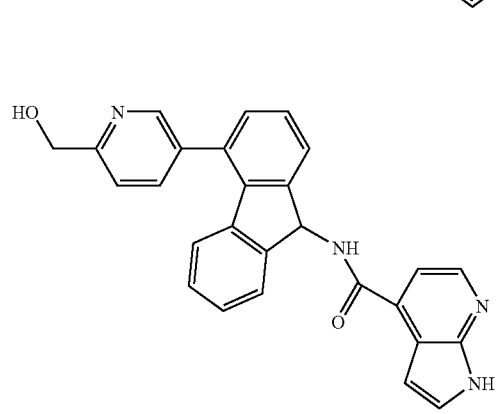 |
| 24-63 | 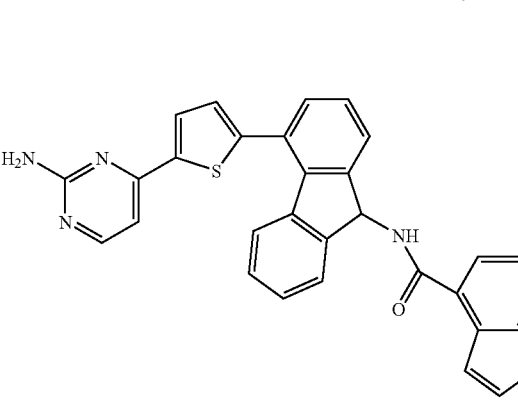 |
| 24-64 | 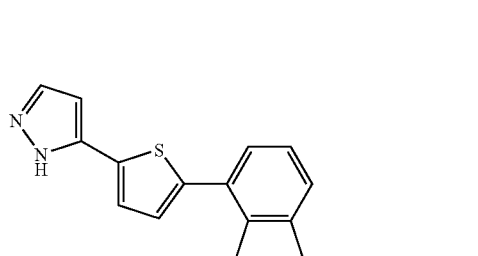 |

TABLE 1-continued

Examples 24-01 to 24-106

| Example | Structure |
|---------|-----------|
| 24-65 | 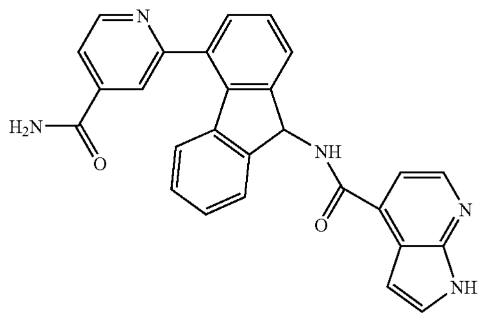 |
| 24-66 | 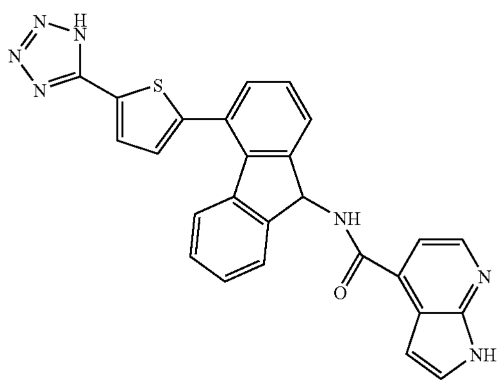 |
| 24-67 | 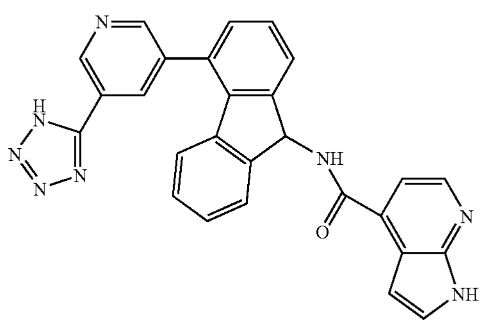 |
| 24-68 | 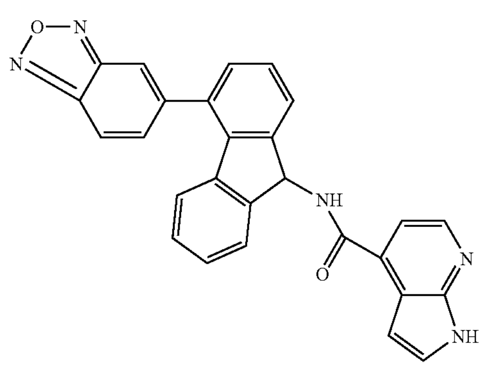 |

TABLE 1-continued
Examples 24-01 to 24-106
| Example | Structure |
|---|---|
| 24-69 | 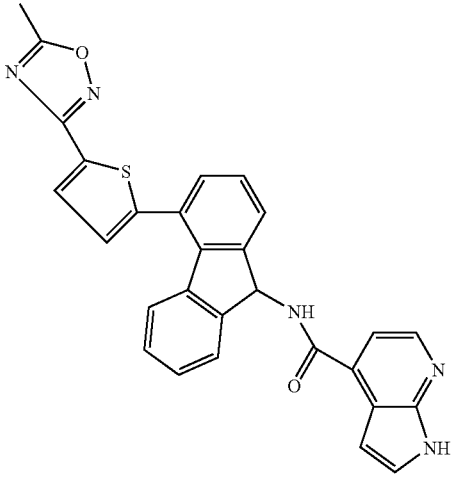 |
| 24-70 | 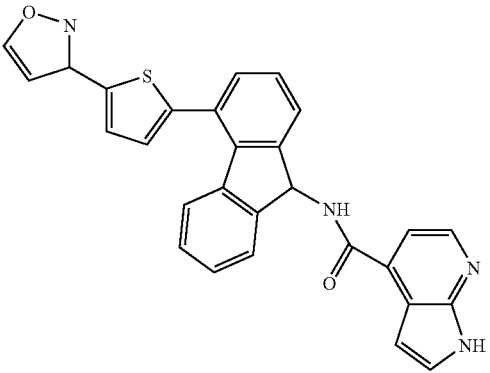 |
| 24-71 | 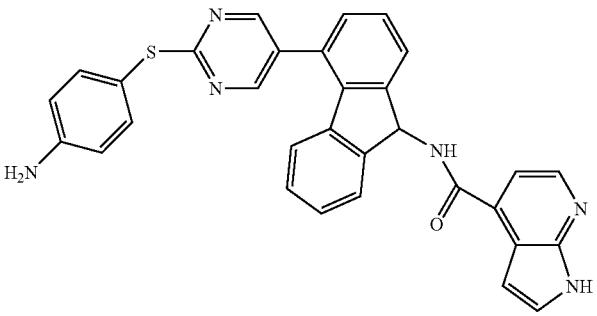 |
| 24-72 | 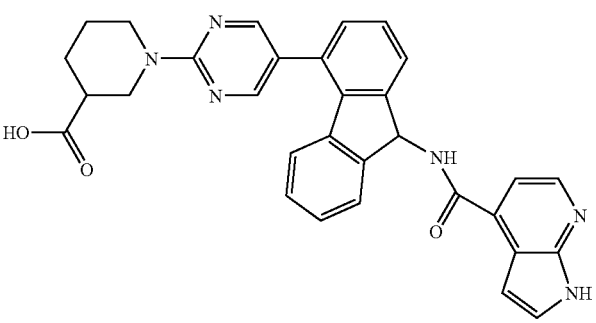 |

TABLE 1-continued
Examples 24-01 to 24-106
| Example | Structure |
|---|---|
| 24-73 | 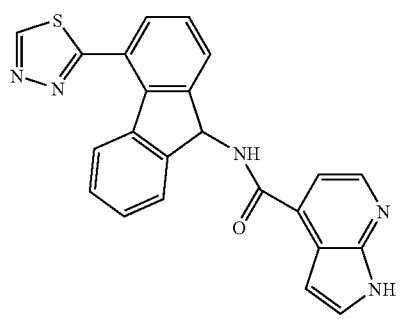 |
| 24-74 | 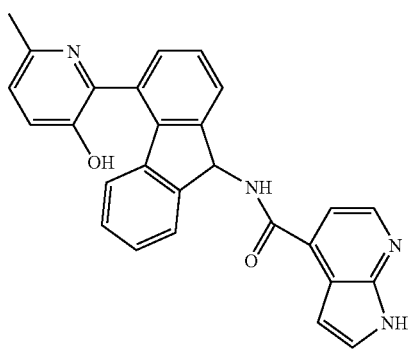 |
| 24-75 | 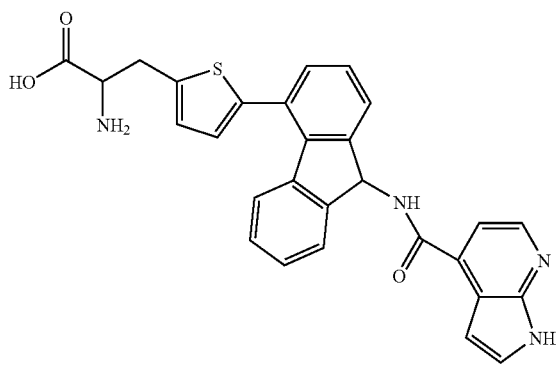 |
| 24-76 | 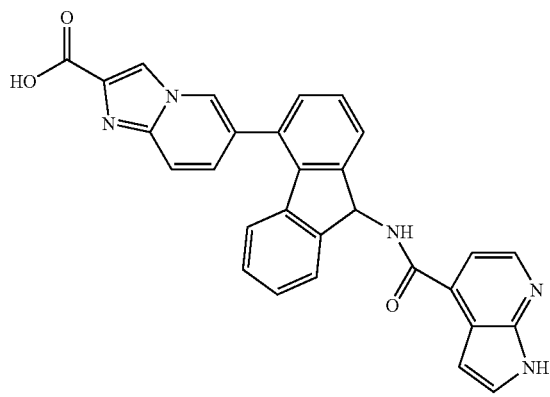 |

TABLE 1-continued
Examples 24-01 to 24-106
| Example | Structure |
|---|---|
| 24-77 | 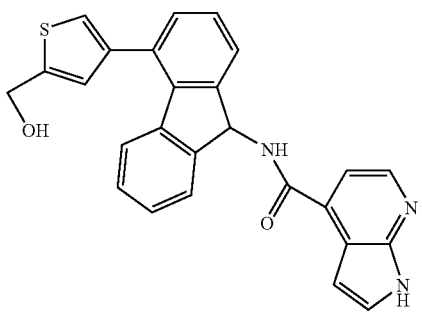 |
| 24-78 | 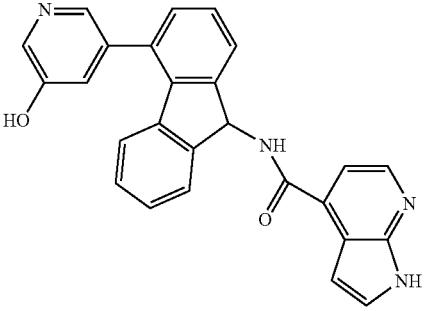 |
| 24-79 | 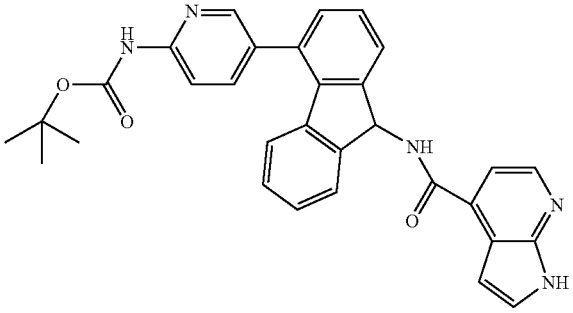 |
| 24-80 | 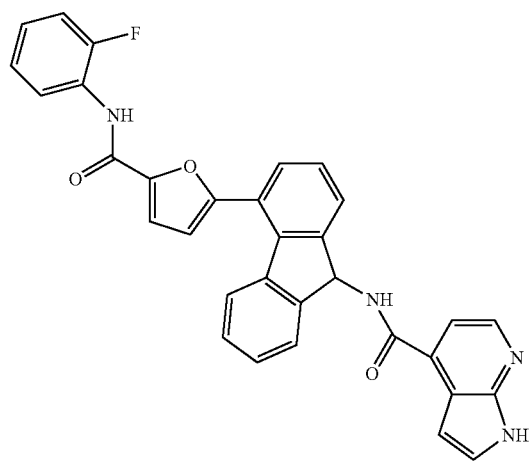 |

TABLE 1-continued
Examples 24-01 to 24-106
| Example | Structure |
|---|---|
| 24-81 | 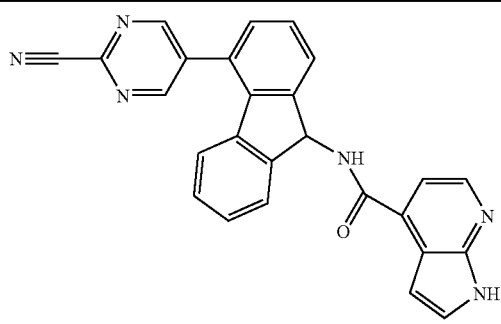 |
| 24-82 | 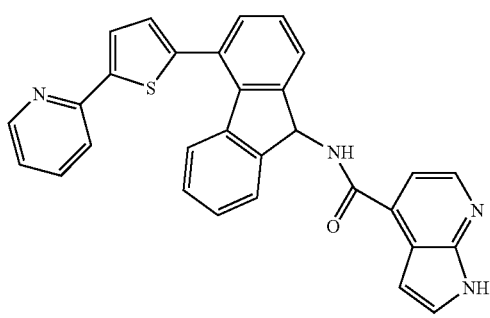 |
| 24-83 | 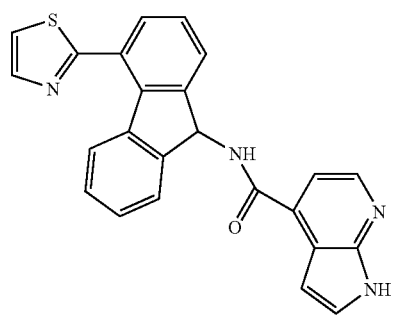 |
| 24-84 | 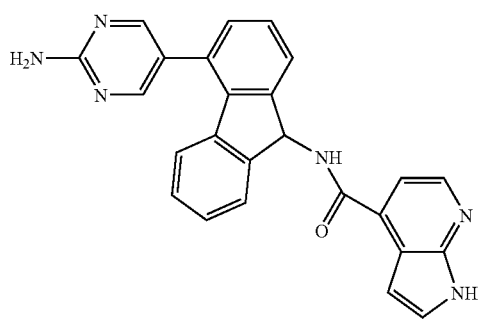 |

TABLE 1-continued

Examples 24-01 to 24-106

| Example | Structure |
|---------|-----------|
| 24-85 | 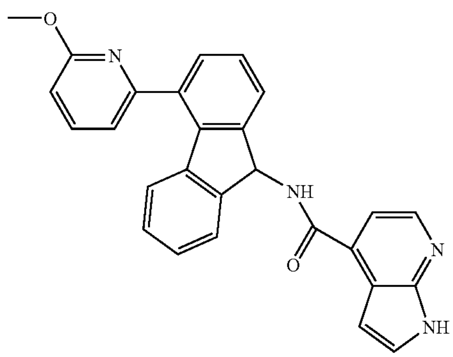 |
| 24-86 | 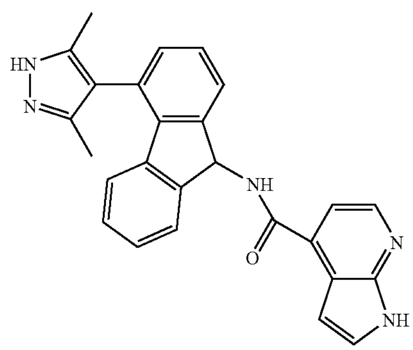 |
| 24-87 | 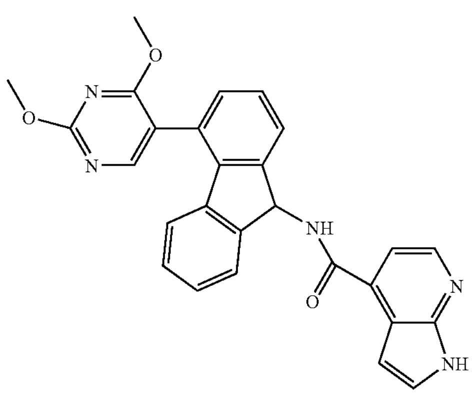 |
| 24-88 | 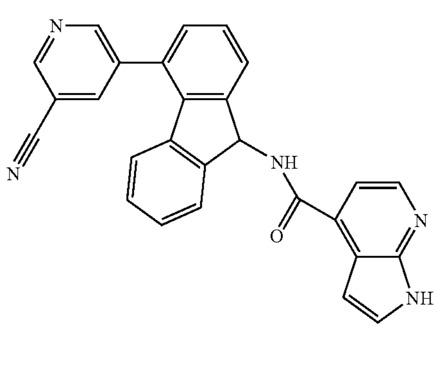 |

TABLE 1-continued

Examples 24-01 to 24-106

| Example | Structure |
|---|---|
| 24-89 | *(structure)* |
| 24-90 | *(structure)* |
| 24-91 | *(structure)* |
| 24-92 | *(structure)* |

TABLE 1-continued
Examples 24-01 to 24-106
| Example | Structure |
|---|---|
| 24-93 | 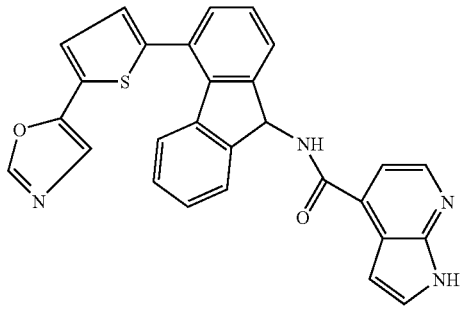 |
| 24-94 | 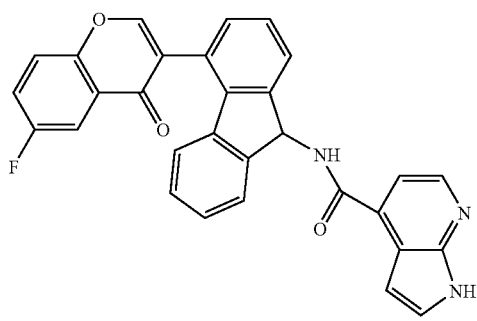 |
| 24-95 | 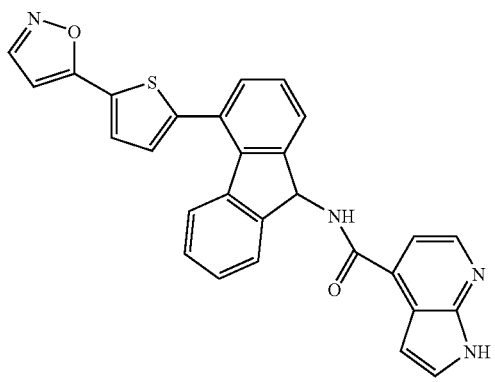 |
| 24-96 | 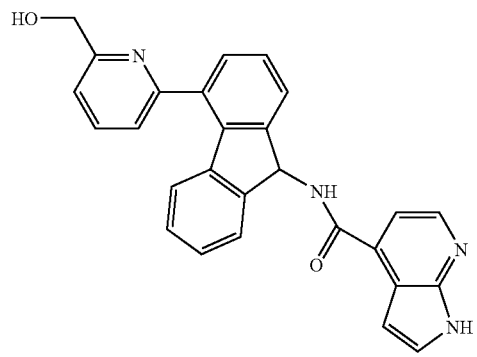 |

TABLE 1-continued
Examples 24-01 to 24-106
| Example | Structure |
|---|---|
| 24-97 | 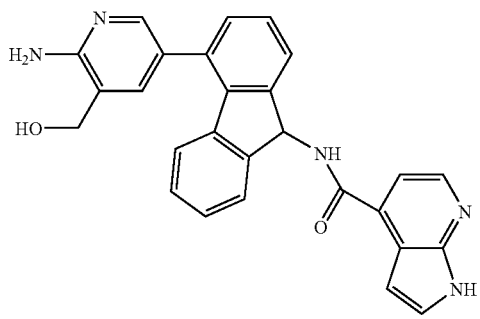 |
| 24-98 | 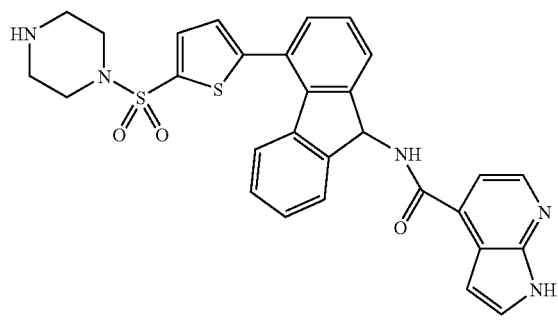 |
| 24-99 | 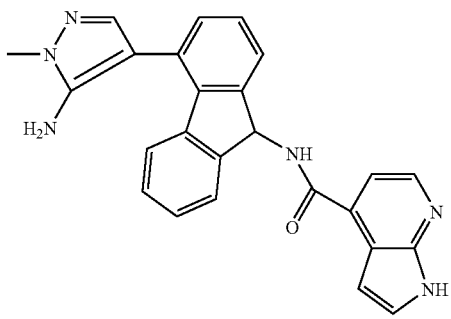 |
| 24-100 | 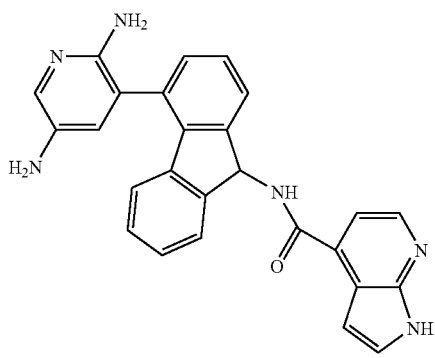 |

TABLE 1-continued
Examples 24-01 to 24-106
| Example | Structure |
|---|---|
| 24-101 | 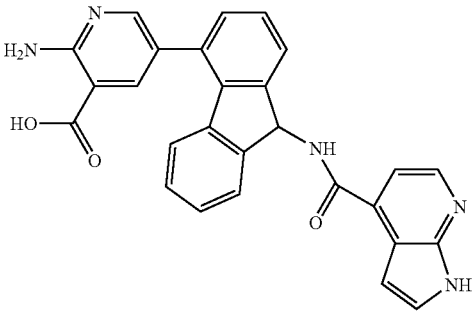 |
| 24-102 | 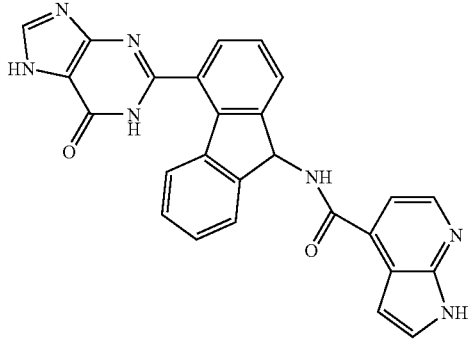 |
| 24-103 | 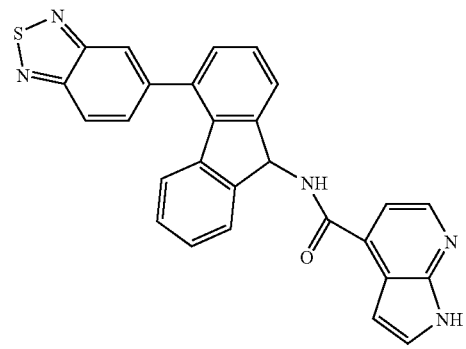 |
| 24-104 | 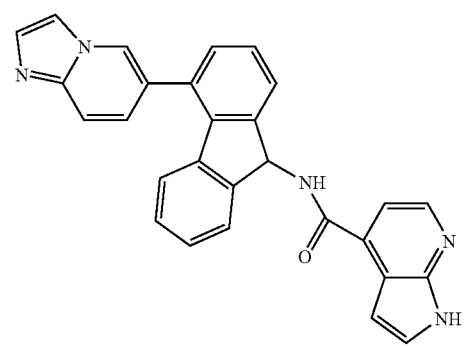 |

TABLE 1-continued

Examples 24-01 to 24-106

| Example | Structure |
|---|---|
| 24-105 | 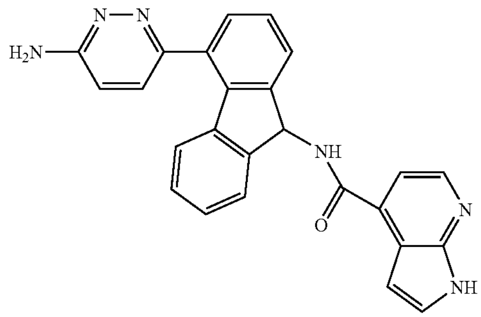 |
| 24-106 | 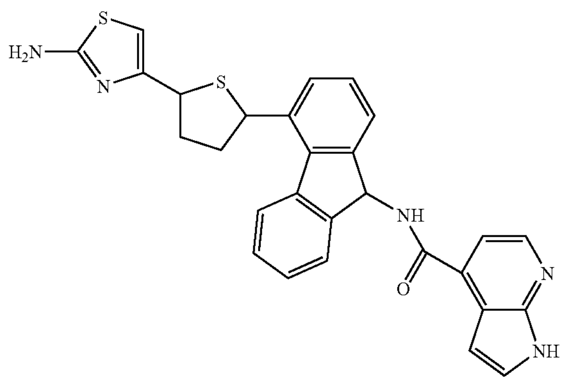 |

Biological tests for biological characterization of the products of the invention: The inorganic phosphate released during hydrolysis of ATP by the ATPase activity of Hsp82 is quantified by the Malachite Green method. In the presence of this reagent, there is formation of the inorganic phosphate-molybdate-malachite green complex, which absorbs at a wavelength of 620 nm.

The test products are incubated in a reaction volume of 30 µl, in the presence of 1 µm Hsp82 and 250 µm of substrate (ATP) in a buffer composed of 50 mM Hepes-NaOH (pH 7.5), 1 mM DTT, 5 mM $MgCl_2$ and 50 mM KCl at 37° C. for 60 min. In parallel, a range of inorganic phosphate between 1 and 40 µm is prepared in the same buffer. The ATPase activity is then revealed by adding 60 µl of the reagent biomol green (Tebu). After incubation for 20 min at room temperature, the absorbance of the different wells is measured by means of a microplate reader at 620 nm. The concentration of inorganic phosphate in each sample is then calculated from the calibration curve. The ATPase activity of Hsp82 is expressed as the concentration of inorganic phosphate produced in 60 min. The effect of the various products tested is expressed as percentage inhibition of ATPase activity.

In the above test, compound A000187458 has a 50% inhibitory concentration ($IC_{50}$) equal to 2.5 µM.

The formation of ADP due to the ATPase activity of Hsp82 was utilized for developing another method of evaluating the enzymatic activity of this enzyme by the application of an enzymatic coupling system involving pyruvate kinase (PK) and lactate dehydrogenase (LDH). In this spectrophotometric method of the kinetic type, PK catalyses the formation of ATP and pyruvate from phosphoenol-pyruvate (PEP) and ADP produced by HSP82. The pyruvate formed, a substrate of LDH, is then converted to lactate in the presence of NADH. In this case, the decrease in the concentration of NADH, measured from the decrease in absorbance at a wavelength of 340 nm, is proportional to the concentration of ADP produced by HSP82. The test products are incubated in a reaction volume of 100 µl of buffer composed of 100 mM Hepes-NaOH (pH 7.5), 5 mM $MgCl_2$, 1 mM DTT, 150 mM KCl, 0.3 mM NADH, 2.5 mM PEP and 250 µM ATP. This mixture is pre-incubated at 37° C. for 30 min before adding 3.77 units of LDH and 3.77 units of PK. The reaction is initiated by adding the product to be evaluated, at various concentrations, and Hsp82, at a concentration of 1 µM. Measurement of the enzymatic activity of Hsp82 is then performed continuously in a microplate reader, at 37° C., at a wavelength of 340 nm. The initial rate of the reaction is found by measuring the gradient of the tangent at the origin of the curve that is recorded. The enzymatic activity is expressed in µM of ADP formed per minute. The effect of the various products tested is expressed as percentage inhibition of ATPase activity according to the following code:

A: $IC_{50}$<1 µM
B: 1 µM<$IC_{50}$<10 µM
C: 10 µM<$IC_{50}$<100 µM

| Ex | Structure | Hsp82 ATPase IC$_{50}$ μM |
|---|---|---|
| | Table of results | |
| 1 | 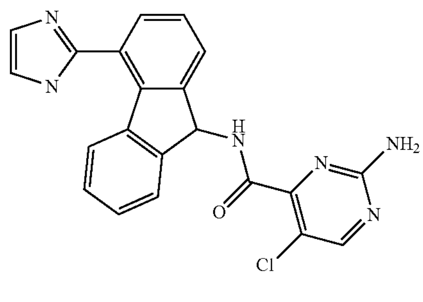 | B |
| 2 | 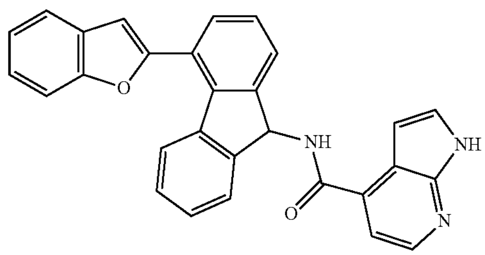 | B |
| 3 | 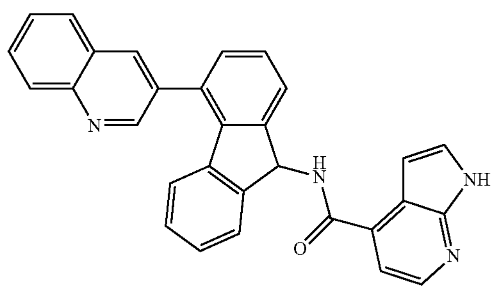 | B |
| 4 | 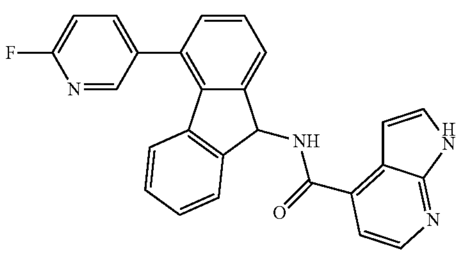 | B |
| 5 | 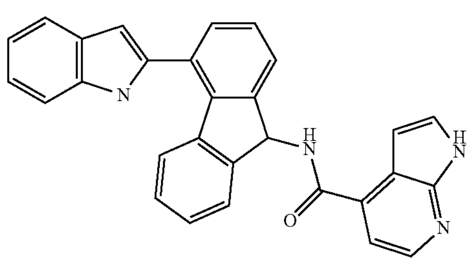 | A |

-continued
Table of results
| Ex | Structure | Hsp82 ATPase IC$_{50}$ μM |
|---|---|---|
| 6 | 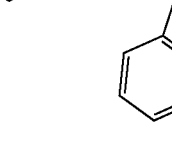 | A |
| 7 | 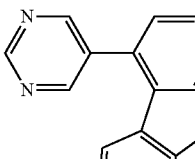 | A |
| 8 | 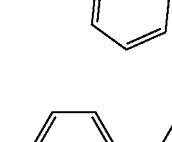 | B |
| 9 | 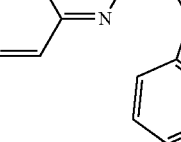 | B |
| 10 | 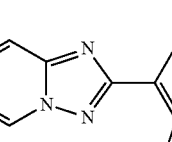 | B |
| 11 | 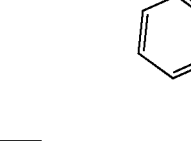 | A |

-continued
| Table of results | | |
|---|---|---|
| Ex | Structure | Hsp82 ATPase IC$_{50}$ μM |
| 12 | 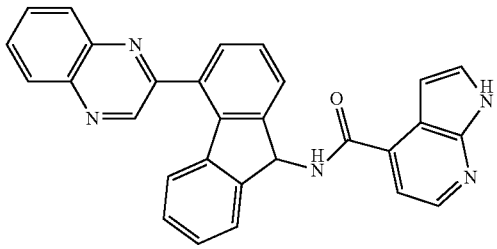 | B |
| 13 | 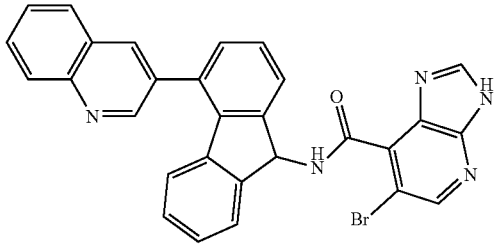 | A |
| 14 | 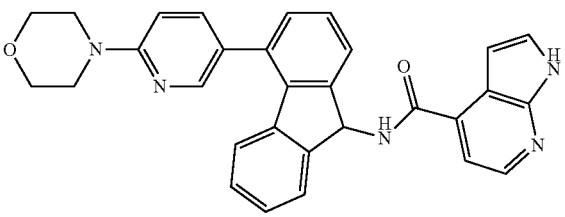 | B |
| 15 | 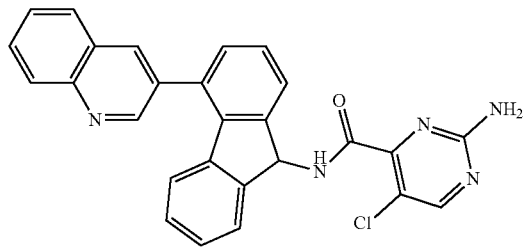 | A |
| 16 | 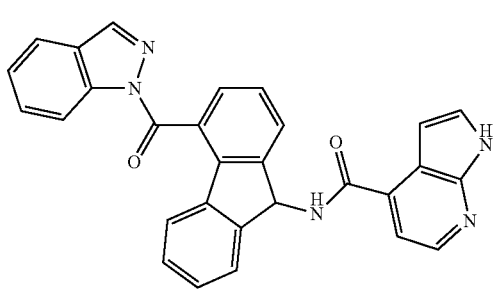 | B |

-continued

Table of results

| Ex | Structure | Hsp82 ATPase IC$_{50}$ μM |
|---|---|---|
| 17 | 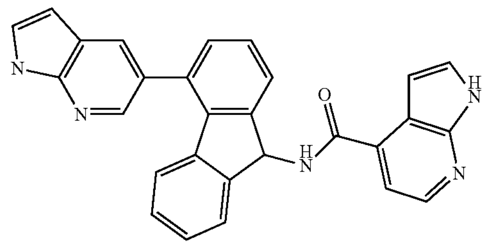 | A |
| 18 | 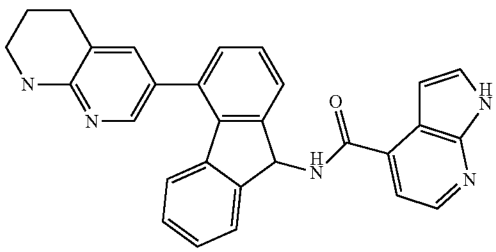 | B |
| 19 | 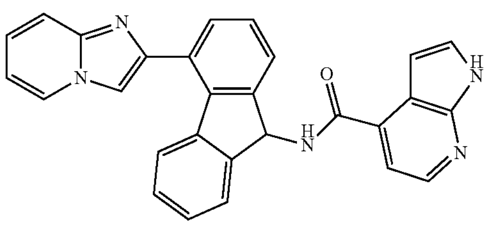 | A |
| 20 | enantiomer (-) | C |
| 21 | Enantiomer (+) | A |

We claim:

1. A compound of formula (I):

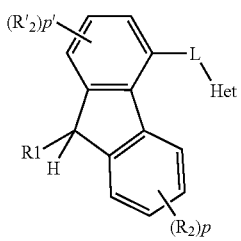

wherein:
Het is imidazolyl, benzofuranyl, quinolinyl, pyridinyl, indolyl, benzoxazolyl, pyrimidinyl, triazolopyridinyl, benzoxazinyl, quinoxalinyl, indazolyl, pyrrolopyridinyl, tetrahydro-1,8-naphthyridinyl, or imidazo[1,2-a]pyridinyl, each of which is optionally substituted independently with one or more times by halogen, cyano or morpholinyl;
R is H, halogen, CF3, nitro, cyano, alkyl, hydroxy, mercapto, amino, alkylamino, dialkylamino, alkoxy, alkylthio, carboxy, COOalkyl, carboxamide, CO—NH(alkyl), CON(alkyl)2, NH—CO-alkyl, NH—S02-alkyl or heterocycloalkyl;
R1 is NH CO-heteroaryl;
X is —O—C(O), —NH—C(O), NH—CS, —NH—CO—CH2-O—, —NH—CO—CH2-S—CH2-CO—NH—, —NH—CO—(CH2)2-SO2-, or —NH—CO—CH2-N(CH3)-CO—;
A and B are, independently, a single bond, CH2, CH-alkyl, or CH-aralkyl;
n is 1 or 2;
m is 0 or 1;
$R_2$ and $R'_2$ are, independently, H, halogen, CF3, nitro, cyano, alkyl, hydroxy, mercapto, amino, alkylamino, dialkylamino, alkoxy, alkylthio (methylthio), carboxy, COOalkyl, carboxamide, CO—NH(alkyl) or NH—CO-alkyl;
P is 1, 2, 3 or 4;
p' is 1, 2 or 3; and
L is a single bond, CH2, C(O), O, S or NH;
or a tautomer, isomer, enantiomer or diastereoisomer thereof, or a salt thereof.

2. The compound according to claim 1, wherein:
Het is imidazolyl, benzofuranyl, quinolinyl, pyridinyl, indolyl, benzoxazolyl, pyrimidinyl, triazolopyridinyl, benzoxazinyl, quinoxalinyl, indazolyl, pyrrolopyridinyl, tetrahydro-1,8-naphthyridinyl, or imidazo[1,2-a]pyridinyl, each of which is optionally substituted independently with one or more times by halogen, cyano or morpholinyl;
R is H, halogen, CF3, nitro, cyano, alkyl, hydroxy, mercapto, amino, alkylamino, dialkylamino, alkoxy, methylthio, carboxy, COOalkyl, carboxamide, CO—NH(alkyl), CON(alkyl)2, NH—CO-alkyl, NH—SO2-alkyl or heterocycloalkyl;
R1 is NH—CO-heteroaryl;
$R_2$ and $R'_2$ are, independently, H, halogen, or amino;
p is 1;
p' is 1; and
L is a single bond or C(O);
or a tautomer, isomer, enantiomer or diastereoisomer thereof, or a salt thereof.

3. The compound according to claim 1, wherein:
R1 is —NH—C(O)-heteroaryl, wherein the heteroaryl is quinolyl, pyridyl, purines, quinoxaline, pyrazole, pyrimidinyl, pyrrolo[2,3-b]pyridine, pyrrolo[2,3-c]pyrimidine, or imidazo[4,5-b]pyridine, and the heteroaryl is optionally substituted independently one or more times by halogen, methyl, ethyl, NH2, or NHalkyl;
R2 and R'2 are H;
L is a single bond or C(O);
or a tautomer, isomer, enantiomer or diastereoisomer thereof, or a salt thereof.

4. The compound according to claim 1, wherein:
R1 is

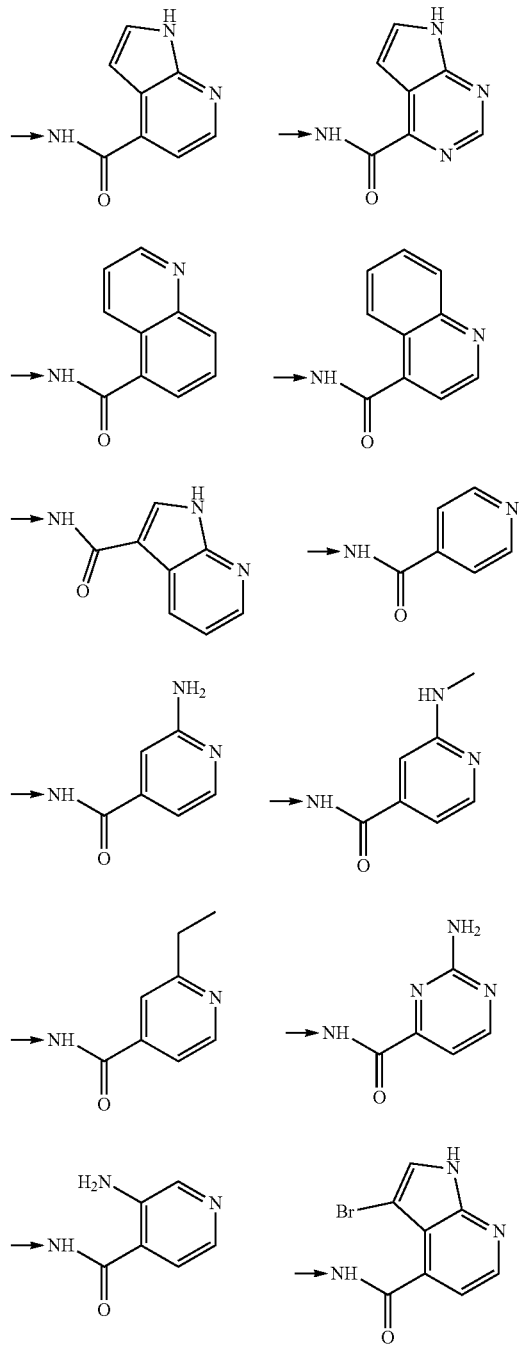

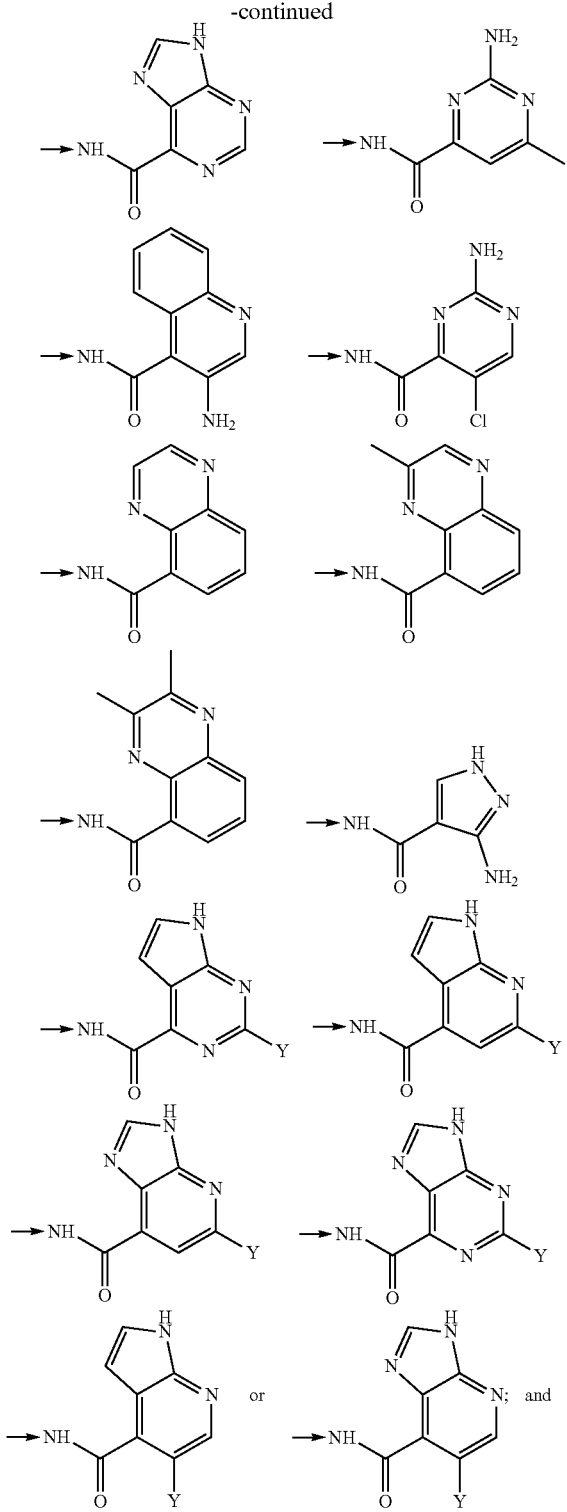

Y is halogen, methyl or ethyl;
or a tautomer, isomer, enantiomer or diastereoisomer thereof, or a salt thereof.

5. A compound which is:
2-Amino-5-chloro-pyrimidine-4-carboxylic acid [4-(1H-imidazol-2-yl)-9H-fluoren-9-yl]-amide;
1H-pyrrolo[2,3-b]pyridine-4-carboxylic acid [4-(benzofuran-2-yl)-9H-fluoren-9-yl)]-amide;
1H-pyrrolo[2,3-b]pyridine-4-carboxylic acid [4-(quinolin-3-yl)-9H-fluoren-9-yl)]-amide;
1H-pyrrolo[2,3-b]pyridine-4-carboxylic acid [4-(6-fluoro-pyridin-3-yl)-9H-fluoren-9-yl]-amide;
1H-pyrrolo[2,3-b]pyridine-4-carboxylic acid [4-(1H-indol-2-yl)-9H-fluoren-9-yl]-amide;
1H-Pyrrolo[2,3-b]pyridine-4-carboxylic acid [4-(benzoxazol-2-yl)-9H-fluoren-9-yl]-amide;
1H-Pyrrolo[2,3-b]pyridine-4-carboxylic acid [4-(pyrimidin-5-yl)-9H-fluoren-9-yl]-amide;
1H-pyrrolo[2,3-b]pyridine-4-carboxylic acid [4-(quinolin-2-yl)-9H-fluoren-9-yl]-amide;
1H-pyrrolo[2,3-b]pyridine-4-carboxylic acid (4-[1.2.4]triazolo[1,5-a]pyridin-2-yl-9H-fluoren-yl)-amide;
1H-pyrrolo[2,3-b]pyridine-4-carboxylic acid [4-(1,4-benzoxazin-2H-3-yl)-9H-fluoren-yl]-amide;
7H-pyrrolo[2,3-c]pyrimidine-4-carboxylic acid [4-(quinolin-3-yl)-9H-fluoren-yl]-amide;
1H-pyrrolo[2,3-b]pyridine-4-carboxylic acid [4-(quinoxalin-2-yl)-9H-fluoren-yl]-amide;
6-bromo-3H-imidazo[4,5-b]pyridine-7-carboxylic acid [4-(quinolin-3-yl)-9H-fluoren-yl]-amide;
1H-pyrrolo[2,3-b]pyridine-4-carboxylic acid [4-(2-morpholino-pyridin-5-yl)-9H-fluoren-yl]-amide;
2-amino-5-chloro-pyrimidine-4-carboxylic acid [4-(quinolin-3-yl)-9H-fluoren-yl]-amide;
1H-pyrrolo[2,3-b]pyridine-4-carboxylic acid [4-(indazole-1-carbonyl)-9H-fluoren-yl]-amide;
1H-pyrrolo[2,3-b]pyridine-4-carboxylic acid [4-(1H-pyrrolo[2,3-b]pyridin-5-yl)-9H-fluoren-yl]-amide;
1H-pyrrolo[2,3-b]pyridine-4-carboxylic acid 4-(5,6,7,8-tetrahydro-1,8-naphthyridin-3-yl)-9H-fluoren-yl]-amide;
1H-pyrrolo[2,3-b]pyridine-4-carboxylic acid 4-{imidazo[1,2-a]pyridin-2-yl}-9H-fluoren-9-yl-amide; or
dextrorotatory enantiomer of 6-bromo-3H-imidazo[4,5-b]pyridine-7-carboxylic acid [4-(quinolin-3-yl)-9H-fluoren-9-yl]-amide;
or a tautomer, isomer, enantiomer or diastereoisomer thereof, or a salt thereof.

6. A pharmaceutical composition comprising the compound according to claim 1, or a tautomer, isomer, enantiomer or diastereoisomer thereof, or a pharmaceutically acceptable salt thereof, in combination with at least one pharmaceutically acceptable excipient.

7. The pharmaceutical composition according to claim 6, further comprising one additional active ingredient, wherein the additional active ingredient is used for cancer chemotherapy.

8. A pharmaceutical composition comprising the compound according to claim 2, or a tautomer, isomer, enantiomer or diastereoisomer thereof, or a pharmaceutically acceptable salt thereof, in combination with at least one pharmaceutically acceptable excipient.

9. A pharmaceutical composition comprising the compound according to claim 3, or a tautomer, isomer, enantiomer or diastereoisomer thereof, or a pharmaceutically acceptable salt thereof, in combination with at least one pharmaceutically acceptable excipient.

10. A pharmaceutical composition comprising the compound according to claim 4, or a tautomer, isomer, enantiomer or diastereoisomer thereof, or a pharmaceutically acceptable salt thereof, in combination with at least one pharmaceutically acceptable excipient.

11. A pharmaceutical composition comprising the compound according to claim 5, or a tautomer, isomer, enantiomer or diastereoisomer thereof, or a pharmaceutically acceptable acceptable salt thereof, in combination with at least one pharmaceutically acceptable excipient.

12. A method for treating a patient having a disease selected from Huntington's disease, Parkinson's disease, focal cerebral ischaemia, multiple sclerosis, amyotrophic lateral sclerosis, malaria, brugian and bancroftian filarioses, toxoplasmosis, mycoses resistant to treatments, hepatitis B infection, hepatitis C infection, herpes virus, dengue, breakbone fever, spinal or bulbar muscular atrophy, proliferation of mesangial cell, thrombosis, retinopathy, psoriasis, and muscular degeneration which

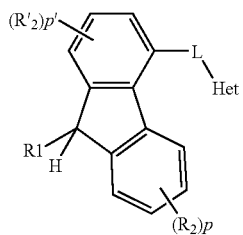

(I)

wherein:

Het is an aromatic or partially unsaturated dihyro or tetrahydro, mono or bicyclic heterocycle having 5 to 11 ring members, containing from 1 to 4 heteroatoms selected from N, 0 and S, which is optionally substituted independently with one or more radicals R;

R is H, halogen, CF3, nitro, cyano, alkyl, hydroxy, mercapto, amino, alkylamino, dialkylamino, alkoxy, alkylthio, carboxy, COOalkyl, carboxamide, CO—NH(alkyl), CON(alkyl)2, NH—CO-alkyl, NH—SO2-alkyl or heterocycloalkyl;

R1 is NH—CO-heteroaryl;

X is —O—C(O), —NH—C(O), NH—CS, —NH—CO—CH2-O—, —NH—CO—CH2-S—CH2-CO—NH—, —NH—CO—(CH2)2-SO2-, or —NH—CO—CH2-N(CH3)-CO—;

A and B are, independently, a single bond, CH2, CH-alkyl, or CH-aralkyl;

n is 1 or 2;

m is 0 or 1;

$R_2$ and $R'_2$ are, independently, H, halogen, CF3, nitro, cyano, alkyl, hydroxy, mercapto, amino, alkylamino, dialkylamino, alkoxy, alkylthio (methylthio), carboxy, COOalkyl, carboxamide, CO—NH(alkyl) or NH—CO-alkyl;

P is 1,2,3 or 4;

P' is 1,2 or 3; and

L is a single bond, CH2, C(O), O, S or NH;

or a tautomer, isomer, enantiomer or diastereoisomer thereof, or a salt thereof.

* * * * *